US012677593B2

(12) United States Patent
Li et al.

(10) Patent No.: US 12,677,593 B2
(45) Date of Patent: Jul. 7, 2026

(54) NITROGEN-CONTAINING FUSED HETEROCYCLIC COMPOUND AND APPLICATIONS THEREOF

(71) Applicant: Ningbo Lumilan Advanced Materials Co., Ltd., Ningbo City (CN)

(72) Inventors: Xiangzhi Li, Ningbo City (CN); Ye Cai, Ningbo City (CN); Ting-Wei Wei, Ningbo City (CN); Huanda Ding, Ningbo City (CN); Zhi-Kuan Chen, Ningbo City (CN)

(73) Assignee: Ningbo Lumilan Advanced Materials Co., Ltd., Ningbo City (CN)

( * ) Notice: Subject to any disclaimer, the term of this patent is extended or adjusted under 35 U.S.C. 154(b) by 1003 days.

(21) Appl. No.: 17/884,199

(22) Filed: Aug. 9, 2022

(65) Prior Publication Data

US 2023/0111454 A1 Apr. 13, 2023

(30) Foreign Application Priority Data

Aug. 10, 2021 (CN) ........................ 202110915286.6

(51) Int. Cl.

| | |
|---|---|
| ***C07D 471/04*** | (2006.01) |
| ***C07D 471/14*** | (2006.01) |
| ***C07D 487/04*** | (2006.01) |
| ***C07D 491/147*** | (2006.01) |
| ***C07D 495/14*** | (2006.01) |
| ***C07D 519/00*** | (2006.01) |
| ***C09K 11/06*** | (2006.01) |
| ***H01L 51/00*** | (2006.01) |
| ***H01L 51/50*** | (2006.01) |
| ***H10K 85/60*** | (2023.01) |
| *H10K 50/11* | (2023.01) |

(52) U.S. Cl.

CPC ....... *H10K 85/6572* (2023.02); *C07D 487/04* (2013.01); *C07D 519/00* (2013.01); *C09K 11/06* (2013.01); *H10K 85/615* (2023.02); *H10K 85/622* (2023.02); *H10K 85/624* (2023.02); *H10K 85/654* (2023.02); *H10K 85/657* (2023.02); *H10K 85/6574* (2023.02); *C09K 2211/1018* (2013.01); *H10K 50/11* (2023.02)

(58) Field of Classification Search

None

See application file for complete search history.

(56) References Cited

U.S. PATENT DOCUMENTS

2019/0263806 A1 * 8/2019 Lee ...................... C07D 495/14

FOREIGN PATENT DOCUMENTS

KR 10-2018-0046152 * 5/2018
WO WO-2018/080068 A1 * 5/2018

* cited by examiner

*Primary Examiner* — Jay Yang
(74) *Attorney, Agent, or Firm* — MUNCY, GEISSLER, OLDS & LOWE, P.C.

(57) ABSTRACT

The present invention provides a nitrogen-containing fused heterocyclic compound and applications thereof. When the nitrogen-containing fused heterocyclic compound of the present invention is used as a host material of an emitting layer of an organic light-emitting element, the organic light-emitting element has a lower driving voltage (3.8 V to 4.1 V), a higher current efficiency (15 Cd/A to 23 Cd/A or higher) and a longer service life (273 h or higher).

7 Claims, No Drawings

NITROGEN-CONTAINING FUSED HETEROCYCLIC COMPOUND AND APPLICATIONS THEREOF

CROSS-REFERENCE TO RELATED APPLICATION

Pursuant to 35 U.S.C. § 119(a), this application claims the benefit of the priority to Chinese Patent Application No. 202110915286.6, filed on Aug. 10, 2021. The content of the prior application is incorporated herein by its entirety.

BACKGROUND OF THE INVENTION

1. Field of the Invention

The present invention belongs to the field of organic electroluminescence materials, and relates to a nitrogen-containing fused heterocyclic compound and applications thereof.

2. Description of the Prior Arts

Recently, the development of organic electroluminescence displays, which are used as an image display device, is actively promoted. Different from liquid crystal display device, the organic electroluminescence display is a self-luminous display, in which the holes and electrons injected from the first electrode and the second electrode are combined with each other in an emissive layer, so as that the luminescence material such as organic compounds comprised in the emissive layer emits light to achieve image display.

Until this moment, luminescence material systems based on fluorescence and phosphorescence have been developed. Organic light-emitting diodes using a fluorescence material are highly reliable, but their internal electroluminescence quantum efficiency under electrical excitation is limited at 25% because the branching ratio of singlet excited state and triplet excited state of excitons is 1:3. On the contrary, organic light-emitting diodes using a phosphorescence material have an internal electroluminescence quantum efficiency of almost 100%. However, the stability of phosphorescence OLEDs still needs to be improved. Beside the luminophor itself, the key material regarding the stability of OLEDs is the host material.

For red and green phosphorescent light-emitting elements, the properties of the host material decide the efficiency and service life of the red and green phosphorescent light-emitting elements. The generally used host material is a series of organic compounds having a carbazolyl group, but such material has disadvantages such as imbalance of charge transport. In addition, such material has a limited stability, which results in a reduced service life of the element.

Thus, in the field of the present invention, it is important to develop a novel high-performance host material

SUMMARY OF THE INVENTION

To overcome the shortcomings of the existing technology, the objective of the present invention is to provide a nitrogen-containing fused heterocyclic compound and applications thereof.

To achieve the above objective, the present invention uses the following technical approaches:

In one aspect, the present invention provides a nitrogen-containing fused heterocyclic compound, in which the nitrogen-containing fused heterocyclic compound has a structure represented by Formula (1):

Formula (1)

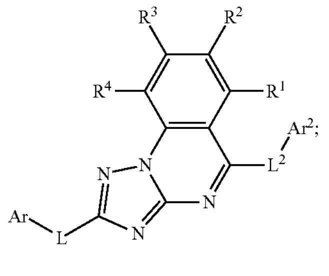

wherein,

Ar and $Ar^2$ are each independently selected from a substituted or unsubstituted C6-C60 aryl group, and a substituted or unsubstituted C3-C60 heteroaryl group;

L and $L^2$ are each independently selected from a bond, a substituted or unsubstituted C6-C30 arylene group, and a substituted or unsubstituted C3-C30 heteroarylene group;

$R^1$ to $R^4$ are each independently selected from hydrogen, deuterium, a halo group, a cyano group, a substituted or unsubstituted C1-C30 alkyl group, a substituted or unsubstituted C7-C30 arylalkyl group, a substituted or unsubstituted C6-C30 aryl group, a substituted or unsubstituted C3-C30 heteroaryl group, a substituted or unsubstituted C4-C30 heteroarylalkyl group, a substituted or unsubstituted C3-C30 cycloalkyl group, a substituted or unsubstituted C3-C30 heterocycloalkyl group, a substituted or unsubstituted C3-C30 cycloalkenyl group, a substituted or unsubstituted C1-C30 alkoxy group and a substituted or unsubstituted C6-C30 aryloxy group; $R^1$ to $R^4$ are present individually without forming a ring, or any adjacent two of $R^1$ to $R^4$ joined to form a ring A, and the ring A is a C6-C30 aromatic ring.

Preferably, the ring A is a benzene ring.

Preferably, Ar is selected from

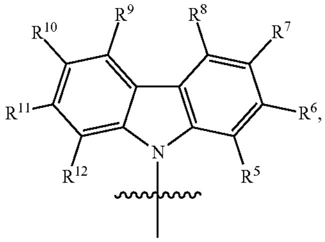

,

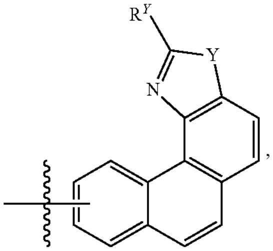

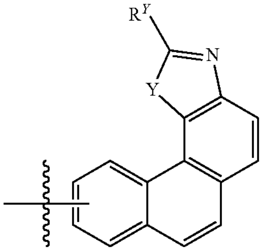

and a substituted or unsubstituted C6-C60 aryl group;

Y is selected from O and S;

$R^Y$ is selected from a substituted or unsubstituted C6-C30 arylene group, and a substituted or unsubstituted C3-C30 heteroarylene group;

$R^5$ to $R^{12}$ are each independently selected from hydrogen, deuterium, a halo group, a cyano group, a substituted or unsubstituted C1-C30 alkyl group, a C1-C30 alkyl group in which one or more methylene groups are independently substituted by —O— and/or —S— in a manner that O atom and/or S atom are not adjacent to each other, a substituted or unsubstituted C2-C30 alkenyl group, a C2-C30 alkenyl group in which one or more methylene groups are independently substituted by —O— and/or —S— in a manner that O atom and/or S atom are not adjacent to each other, a substituted or unsubstituted C2-C30 alkynyl group, a substituted or unsubstituted C7-C30 arylalkyl group, a substituted or unsubstituted C6-C30 aryl group, a substituted or unsubstituted C3-C30 heteroaryl group, a substituted or unsubstituted C4-C30 heteroarylalkyl group, a substituted or unsubstituted C3-C30 cycloalkyl group, a substituted or unsubstituted C3-C30 heterocycloalkyl group, a substituted or unsubstituted C3-C30 cycloalkenyl group, a substituted or unsubstituted C1-C30 alkoxy group, and a substituted or unsubstituted C6-C30 aryloxy group;

$R^5$ to $R^{12}$ are present individually without forming a ring, or any adjacent two to four of $R^5$ to $R^{12}$ joined to form a ring B, the ring B is a substituted or unsubstituted C6-C30 aromatic ring, or a substituted or unsubstituted C3-C30 heteroaromatic ring.

Preferably, the ring B is a substituted or unsubstituted benzene ring, a substituted or unsubstituted naphthalene ring, a substituted or unsubstituted indole ring, a substituted or unsubstituted indene ring, a substituted or unsubstituted benzofuran ring, a substituted or unsubstituted benzothiophene ring, a substituted or unsubstituted benzoindole ring, or a substituted or unsubstituted naphthoindole ring.

Preferably, Ar is selected from

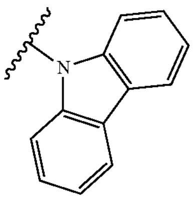
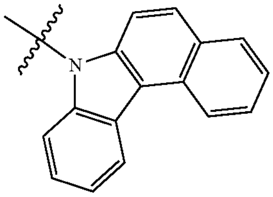
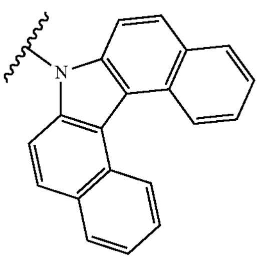
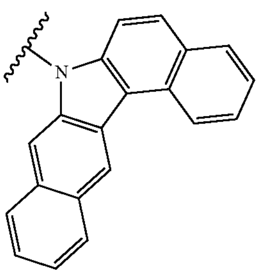

-continued

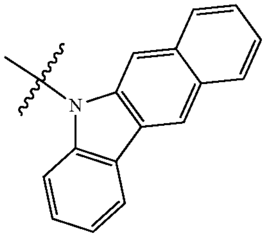
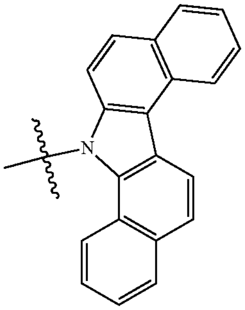
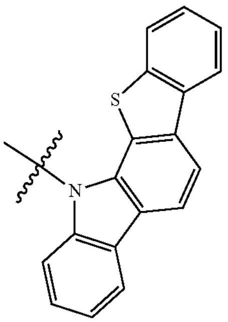
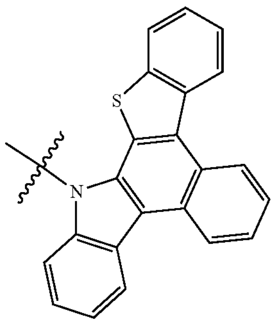
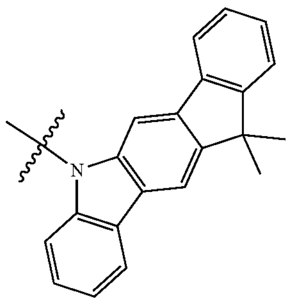
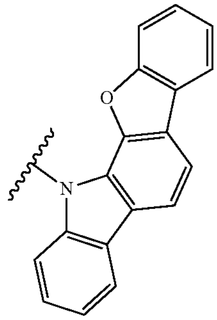
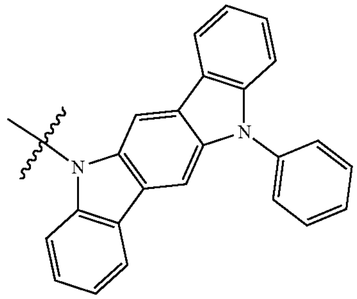
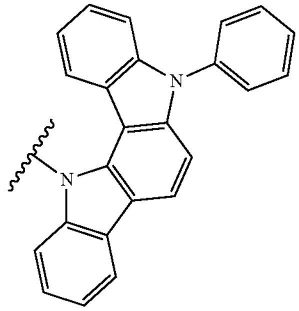

-continued
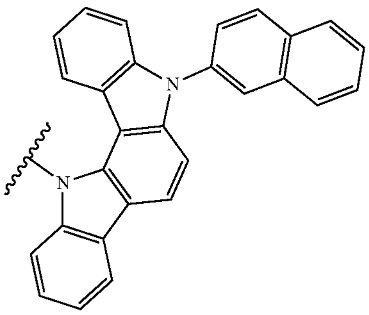
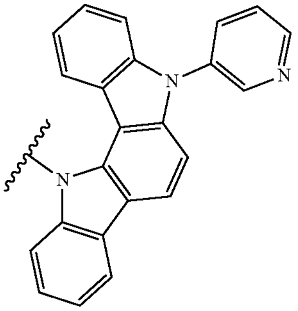
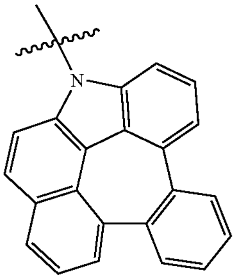
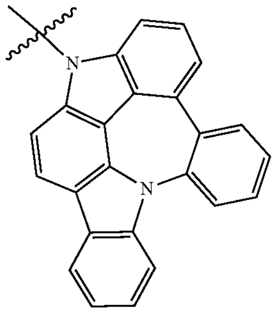
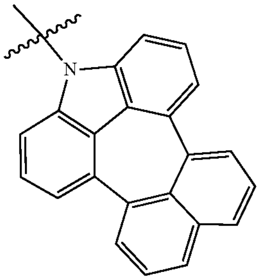
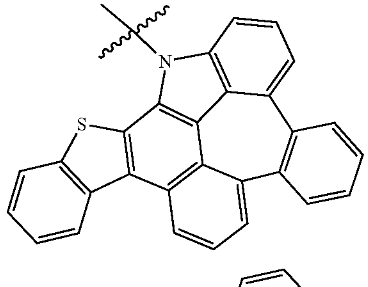
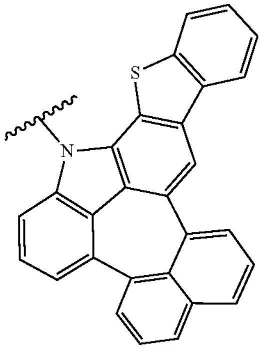
-continued
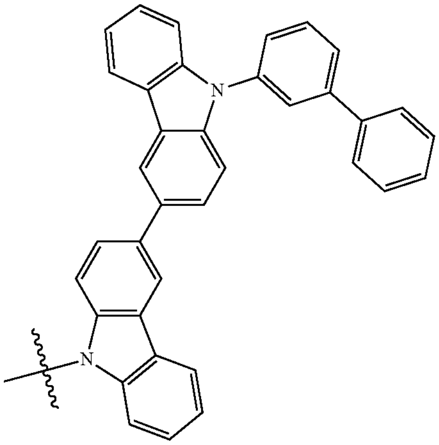
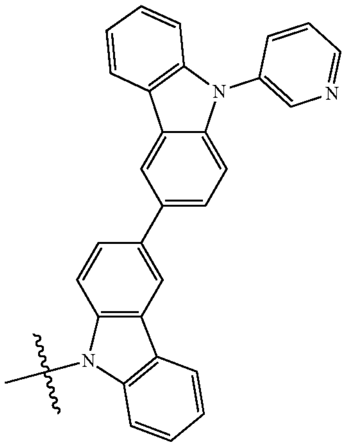
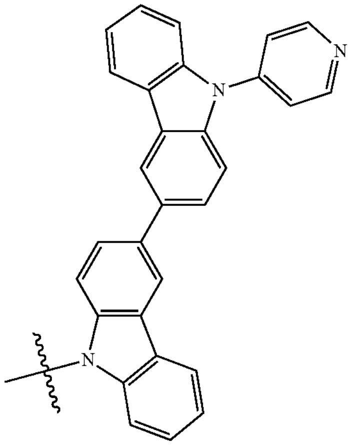

-continued
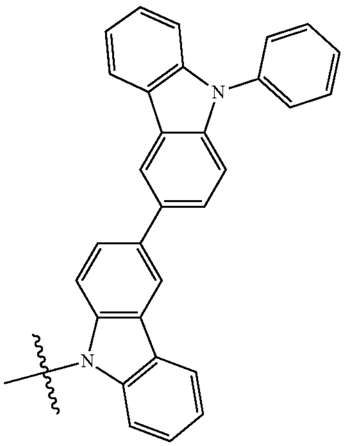
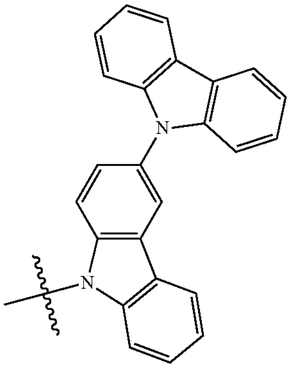
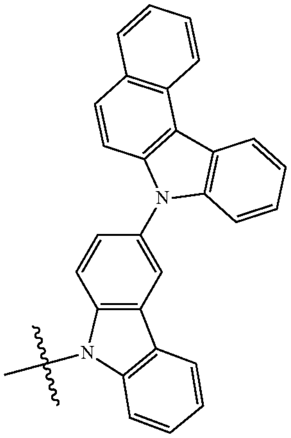
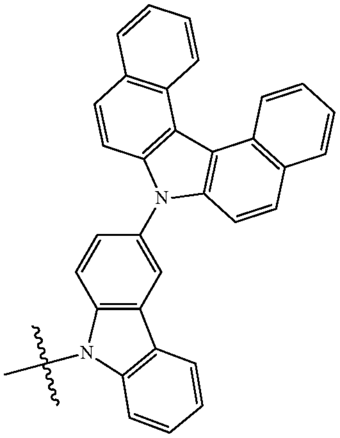
-continued
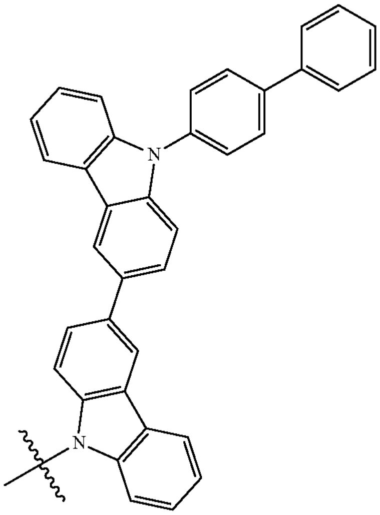
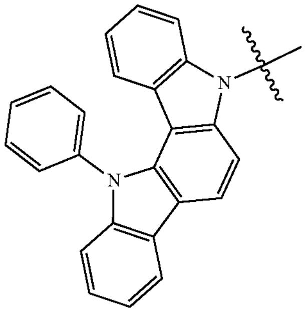
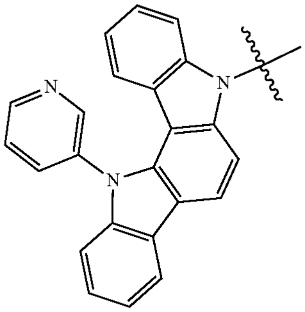
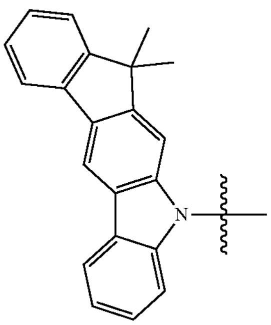
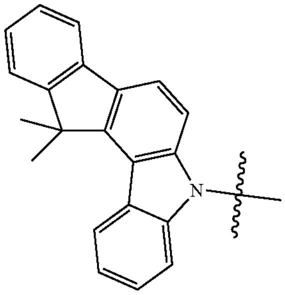

-continued
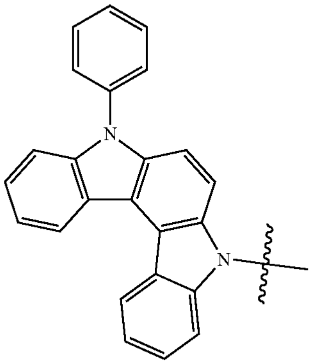
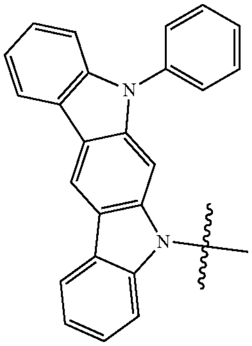
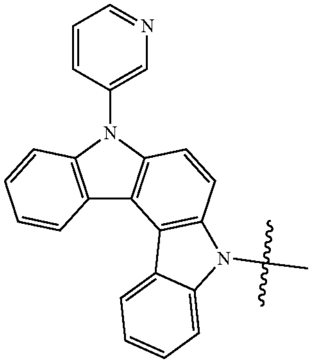
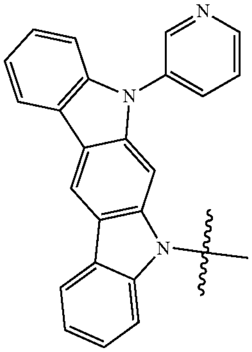
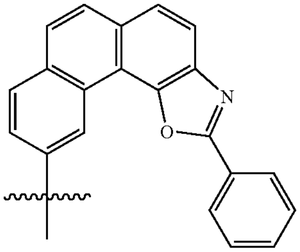
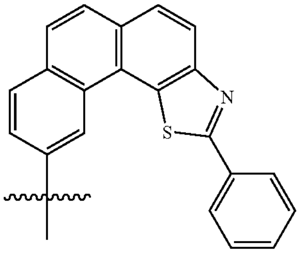
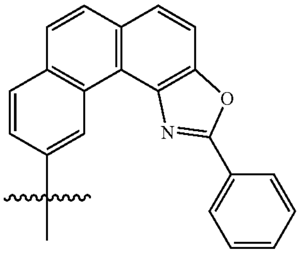
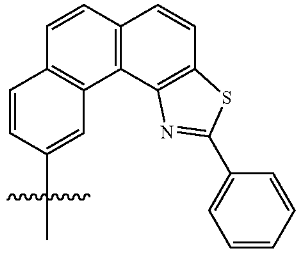
-continued
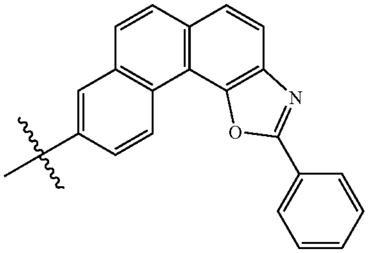
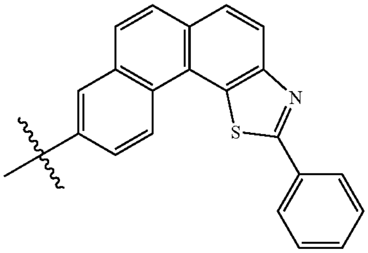
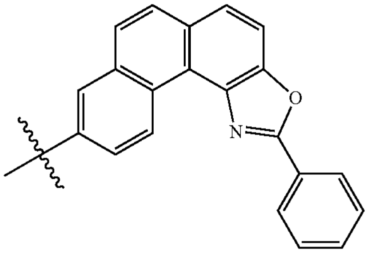
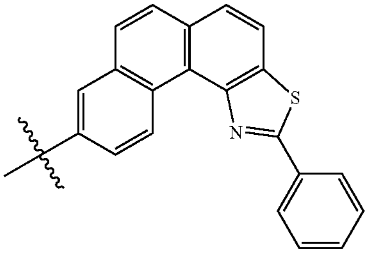
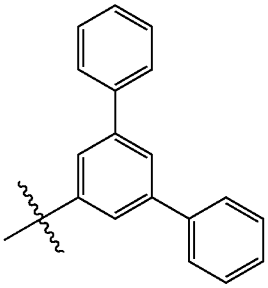
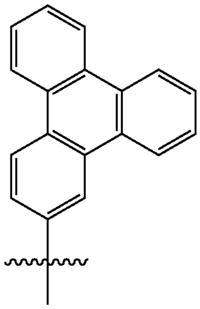
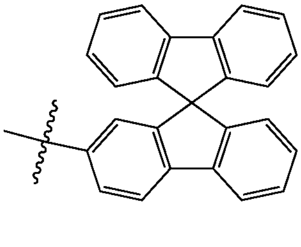
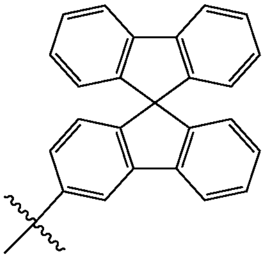

-continued
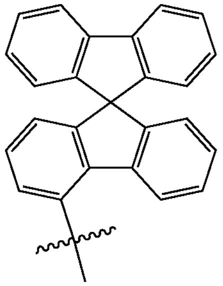
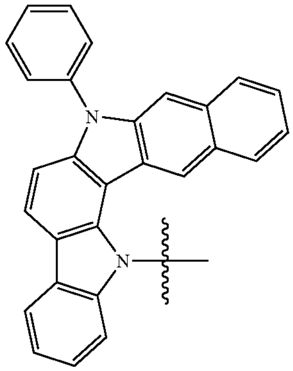
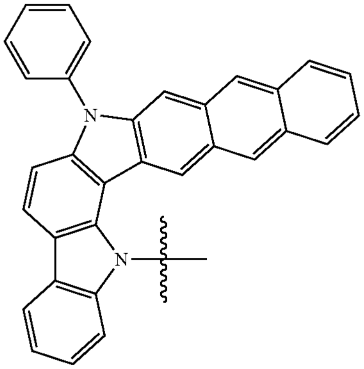
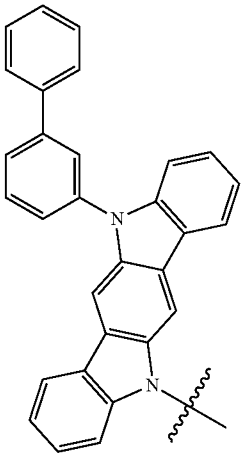
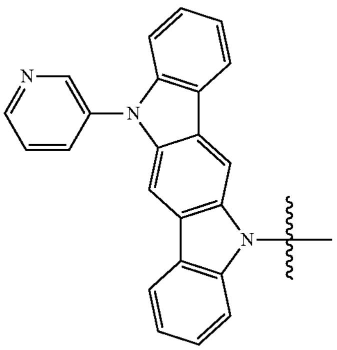
-continued
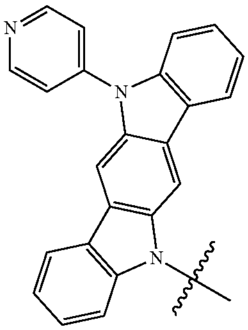
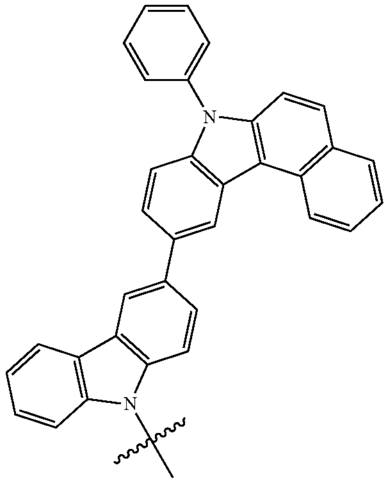
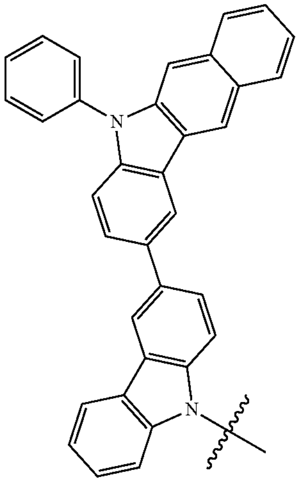
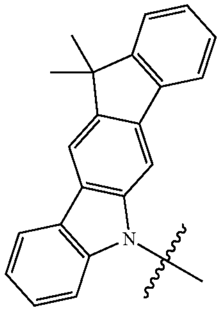
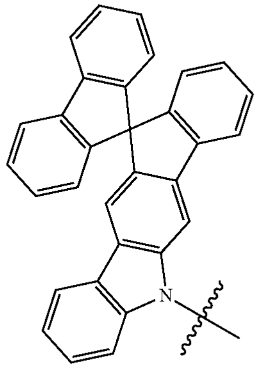
and -continued

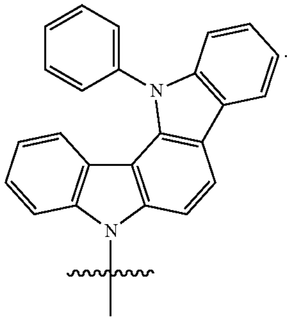

Preferably, Are is selected from a phenyl group, a biphenylyl group, a terphenylyl group, a naphthyl group, a phenylnaphthyl group, a naphthylphenyl group, an anthryl group, a phenanthryl group, a benzophenanthryl group, a pyridyl group, a dibenzofuryl group, a dibenzothiophenyl group, a carbazolyl group, a phenylcarbazolyl group, a pyridylcarbazolyl group, a naphthylcarbazolyl group, a biphenylylcarbazolyl group, a dibenzofurylphenyl group, a dibenzothiophenylphenyl group, a dimethylfluorenyl group, a diphenylfluorenyl group, a spiro-bifluorenyl group, a benzonaphthofuryl group, a benzonaphthothiophenyl group, a benzocarbazolyl group, and a dibenzocarbazolyl group, each of which is substituted or unsubstituted.

Preferably, $L^2$ is selected from a bond, and a group selected from a phenylene group, a biphenylene group, and a naphthylene group, each of which is substituted or unsubstituted.

Preferably, L is selected from a phenylene group, a biphenylene group, and a naphthylene group, each of which is substituted or unsubstituted.

Preferably, the nitrogen-containing fused heterocyclic compound is any one of the following compounds:

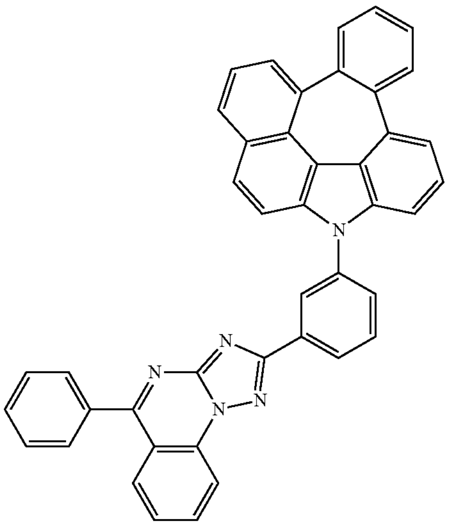

-continued

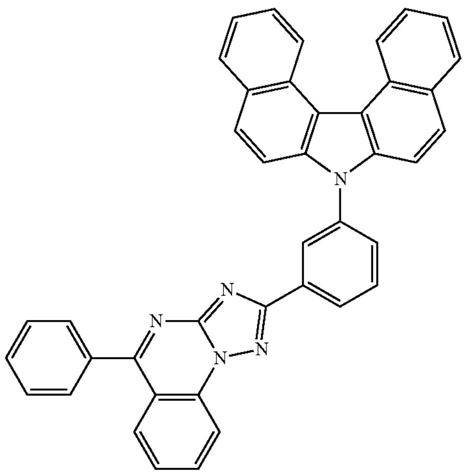

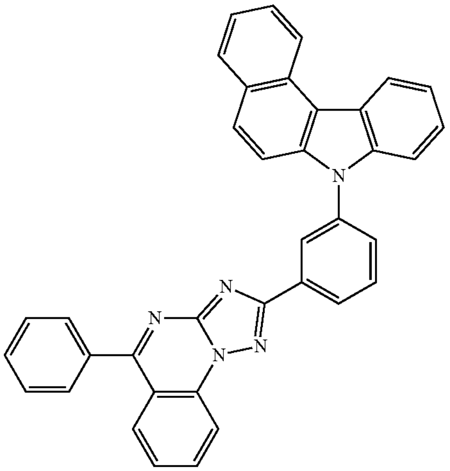

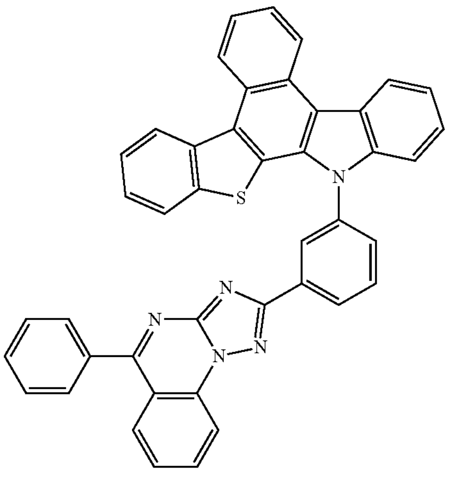

-continued
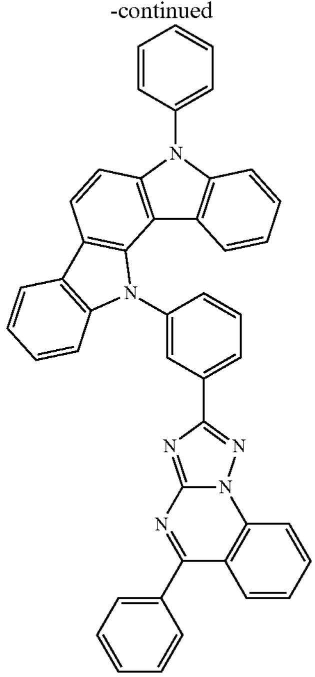
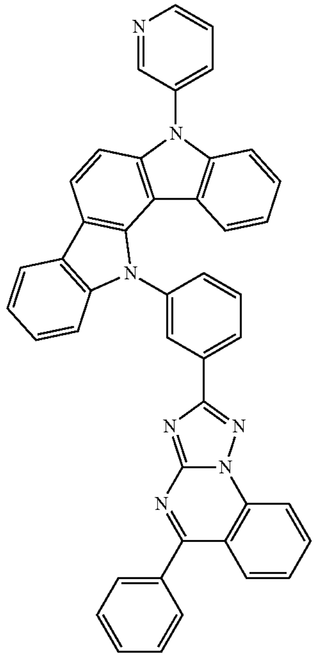
-continued
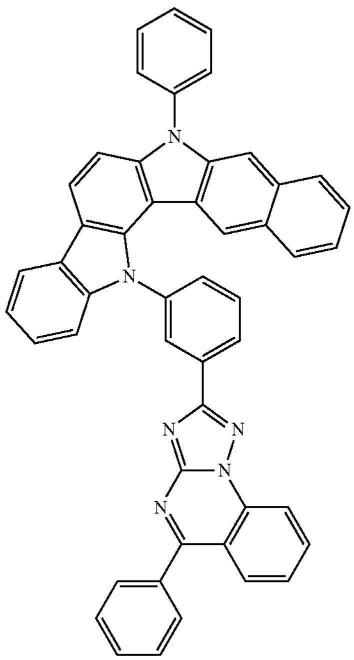
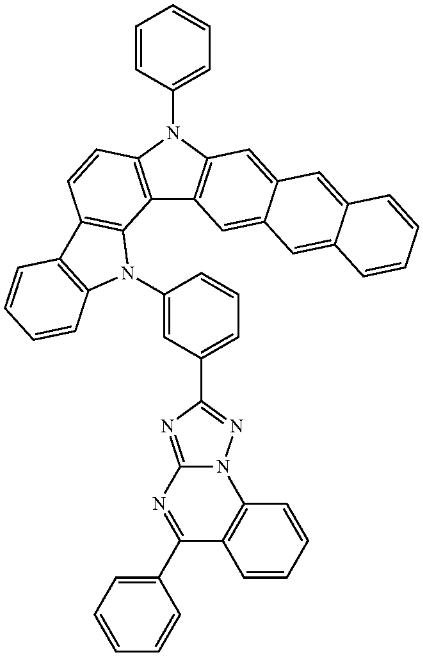

-continued
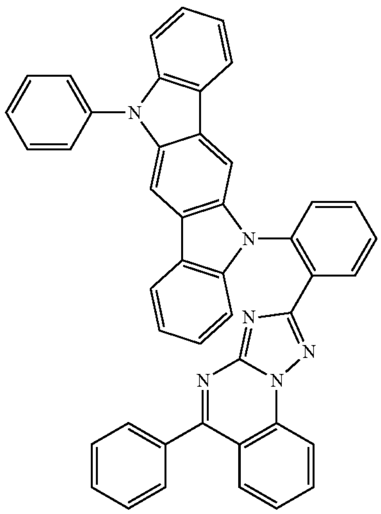
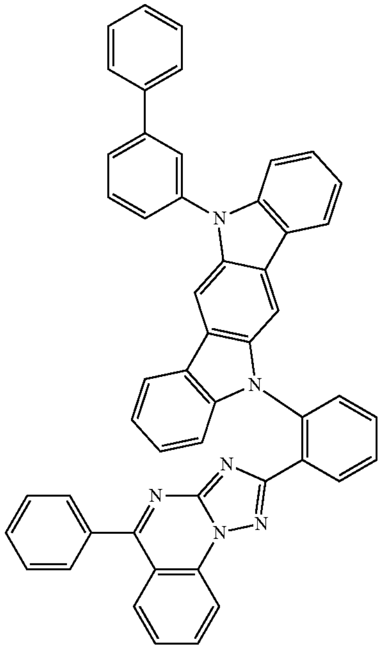
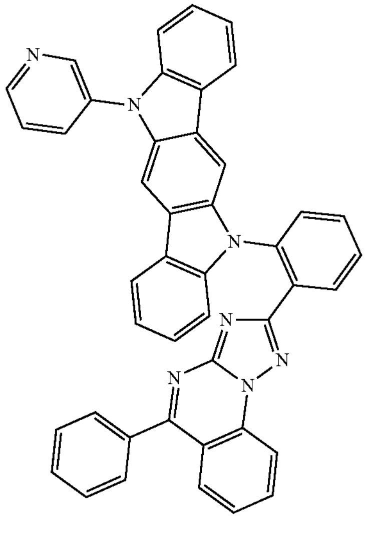
-continued
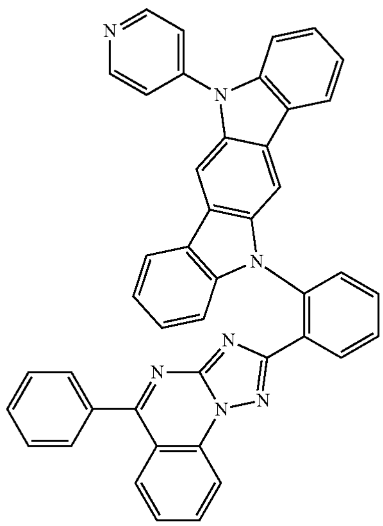
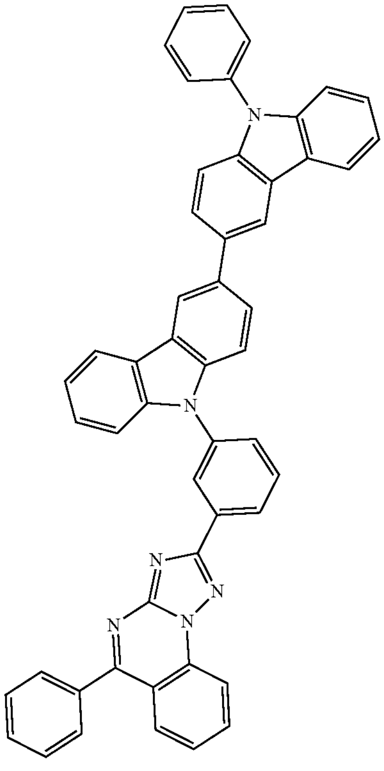

-continued
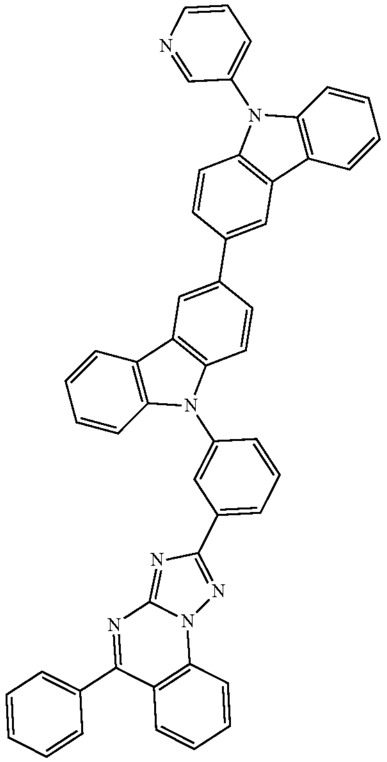
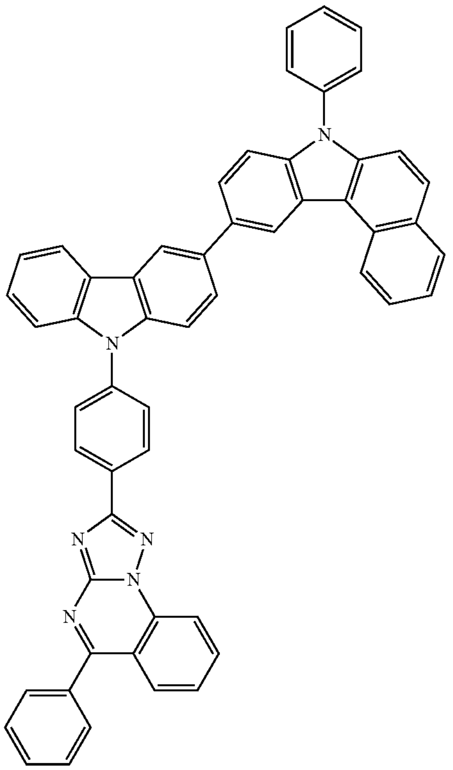
-continued
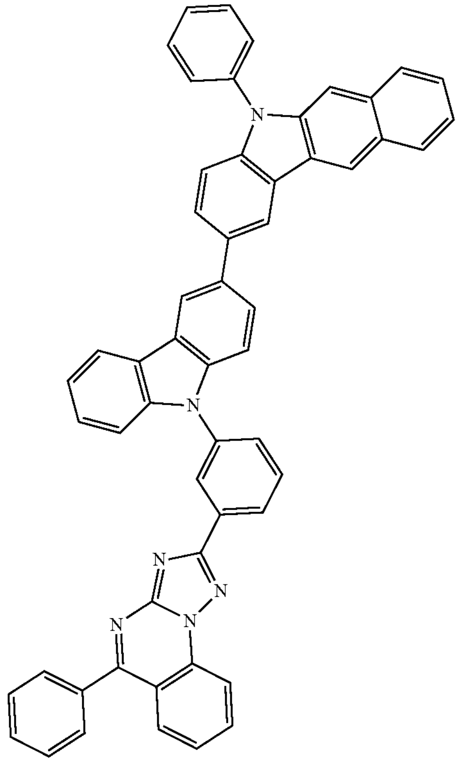
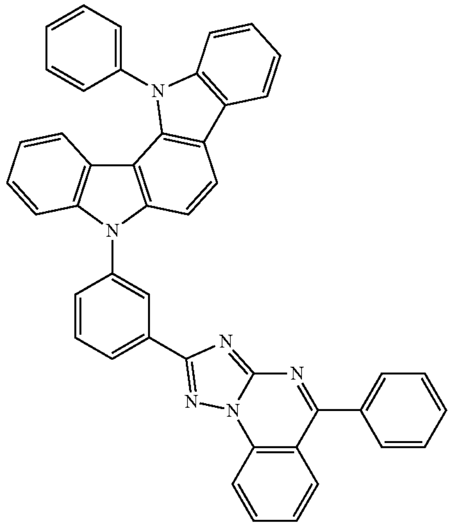

-continued
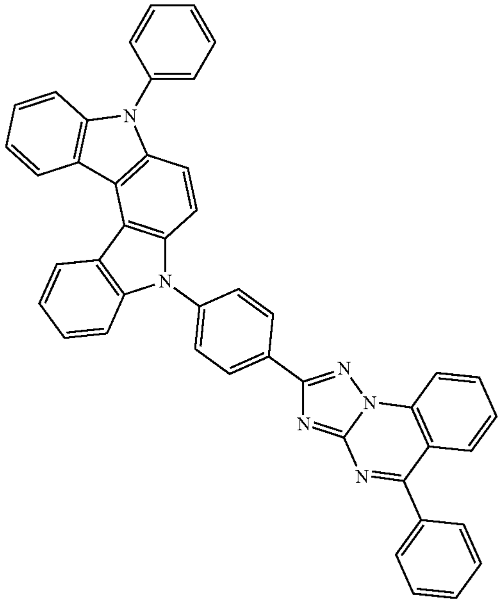
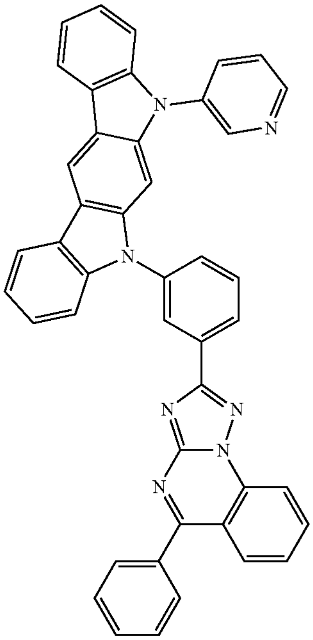
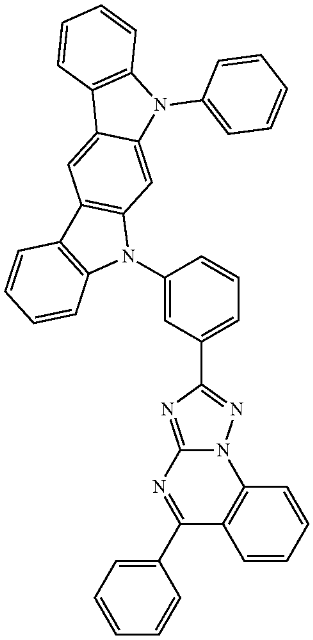
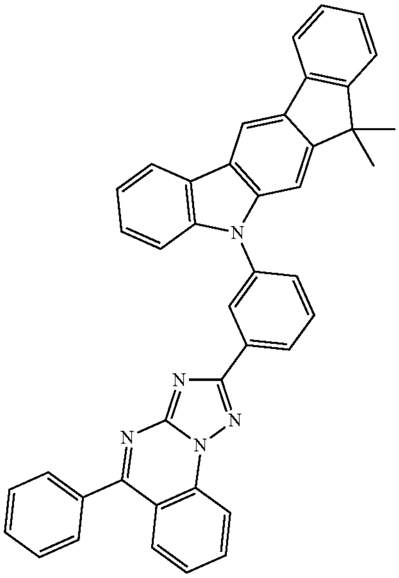
-continued

-continued
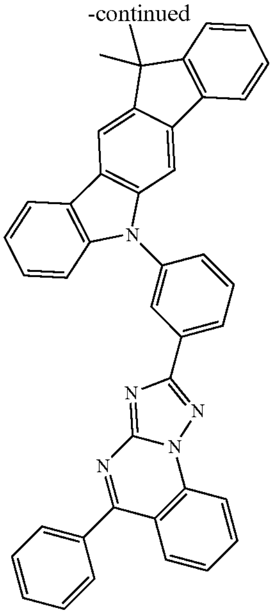
-continued
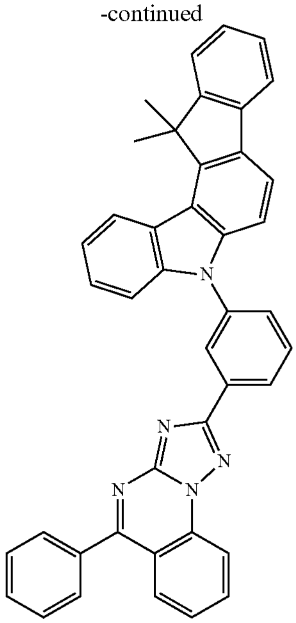
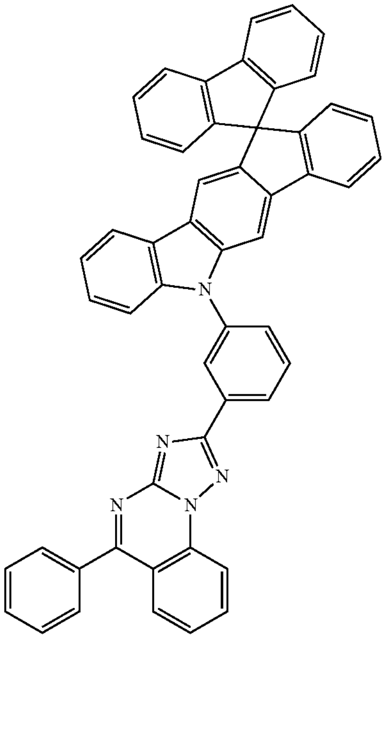
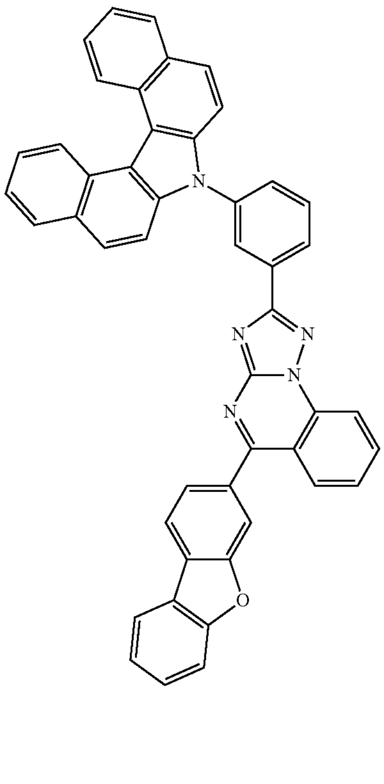

-continued
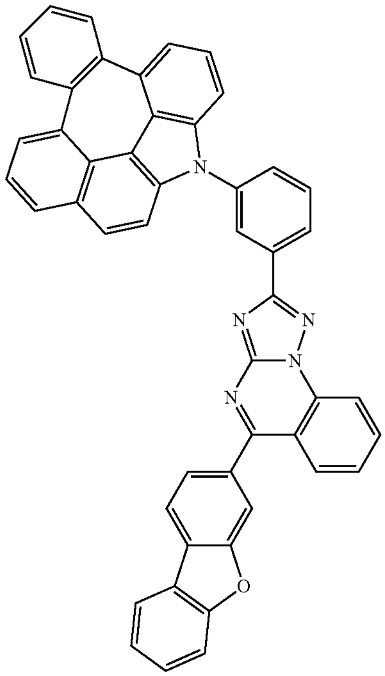
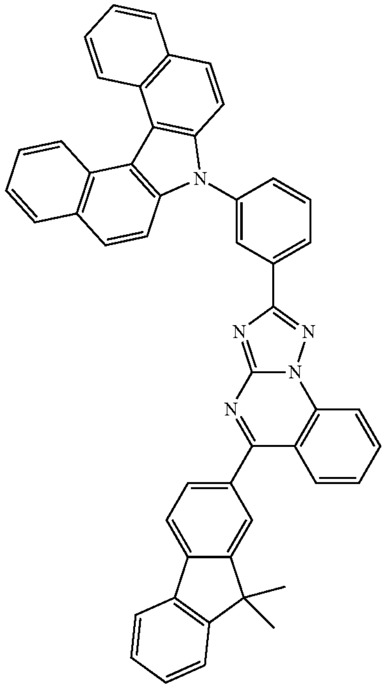
-continued
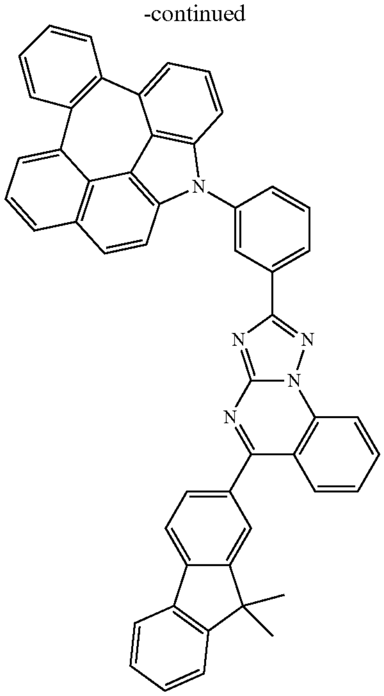
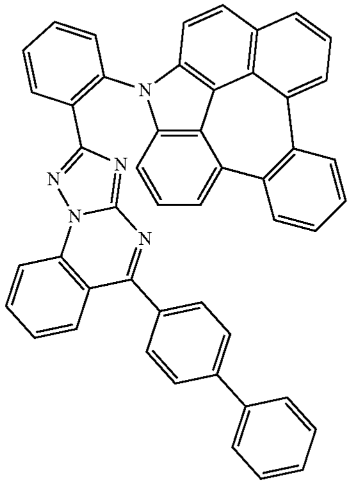
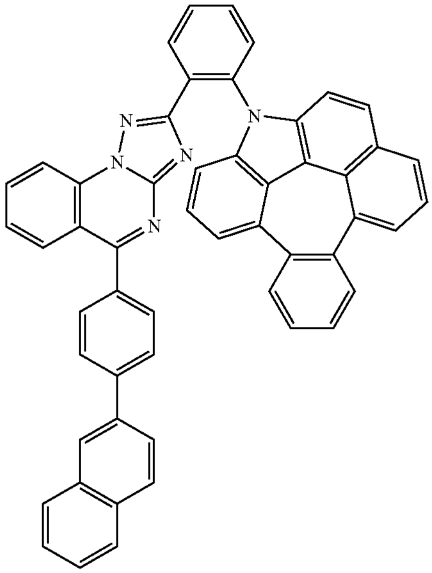

-continued
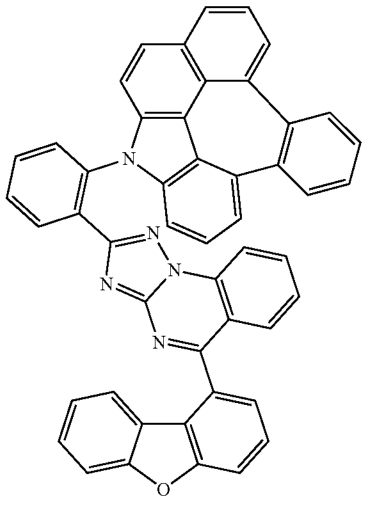
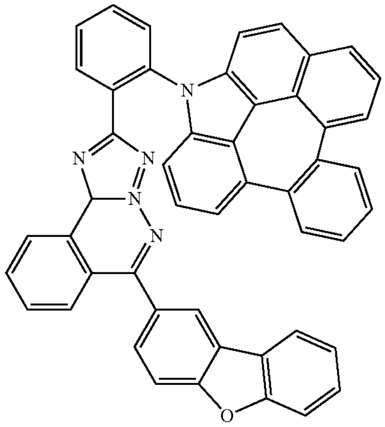
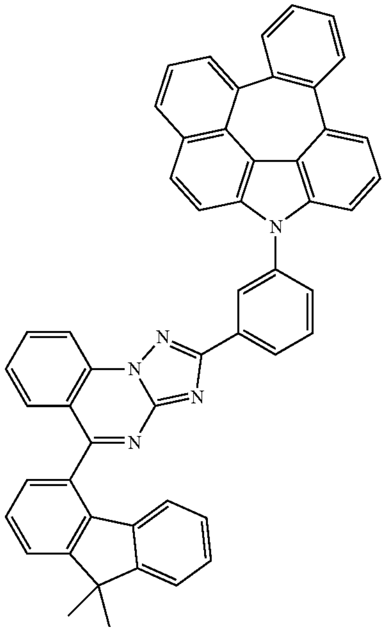
-continued
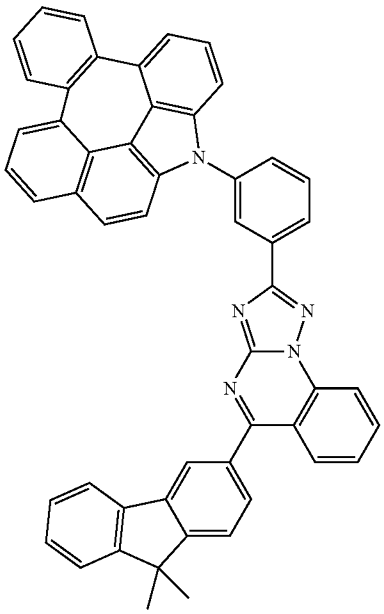
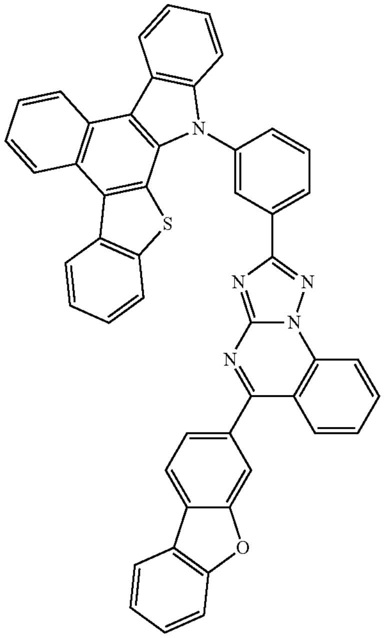

-continued
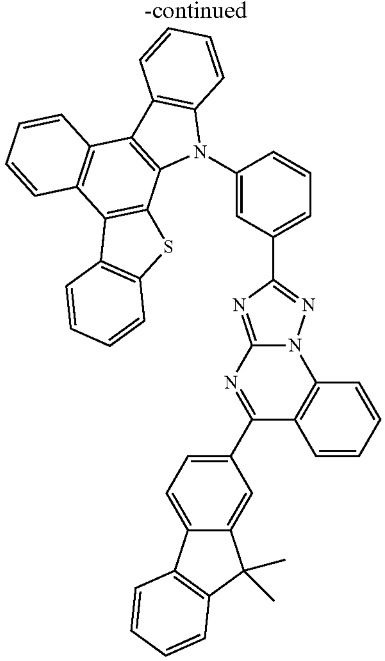
-continued
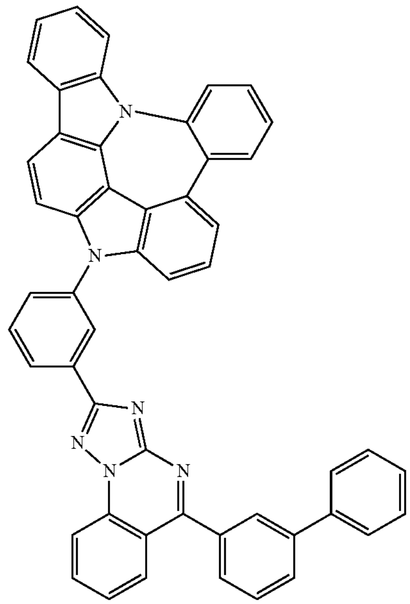
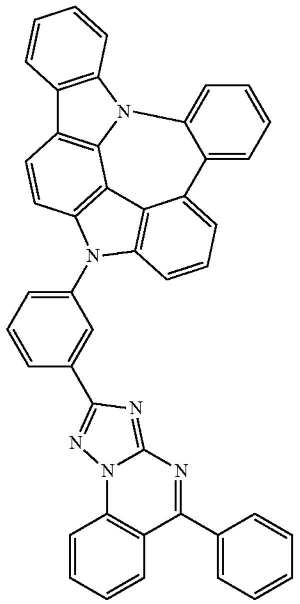
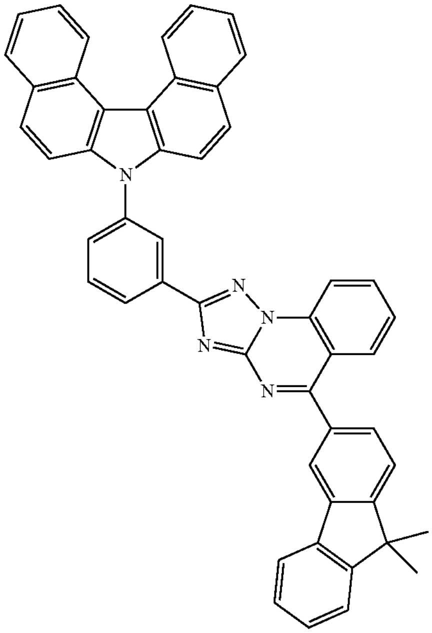

-continued
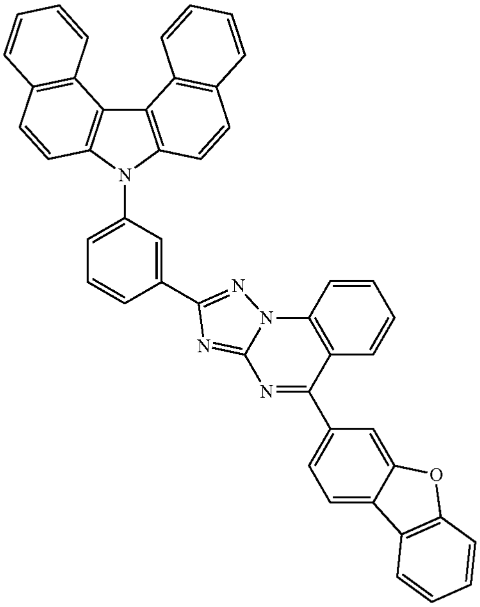
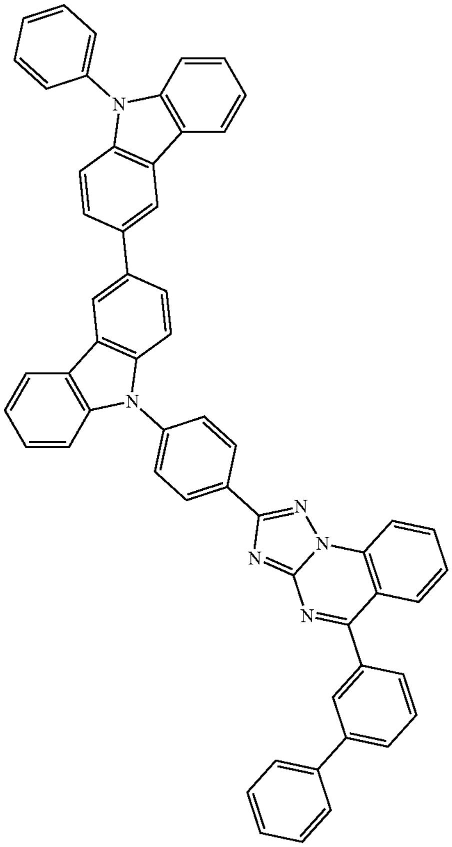
-continued
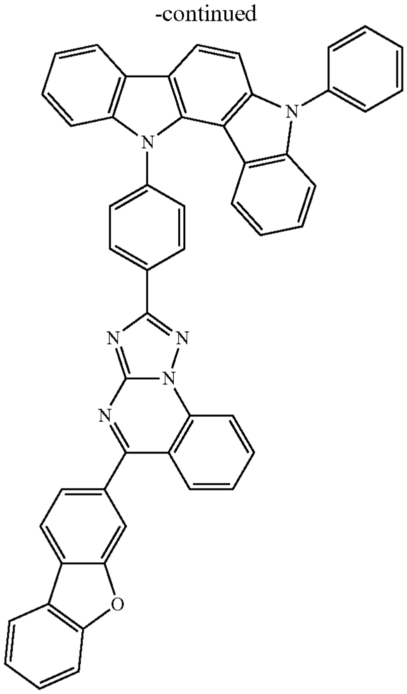
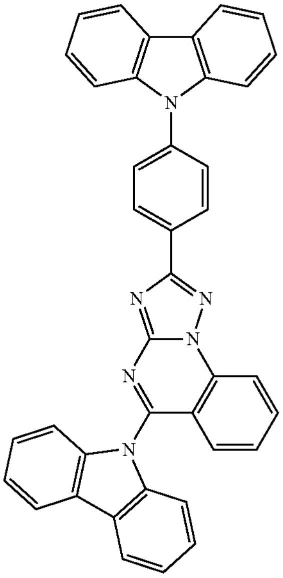

-continued
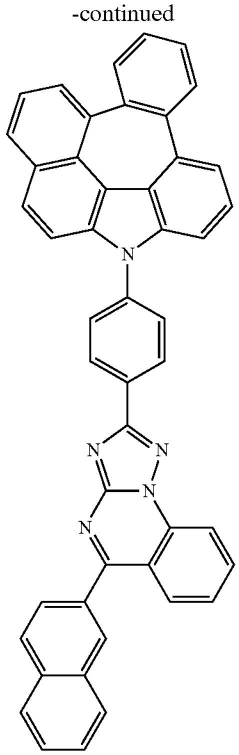
-continued
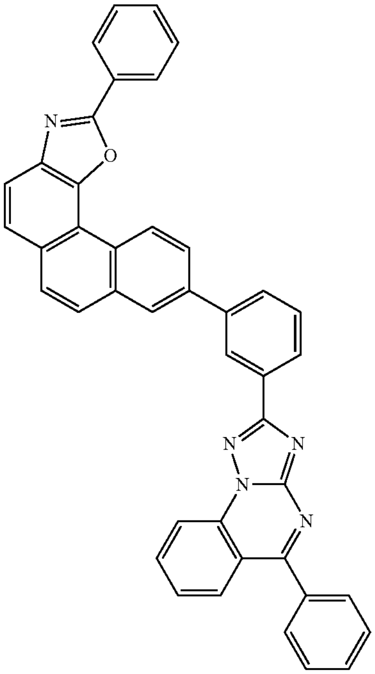
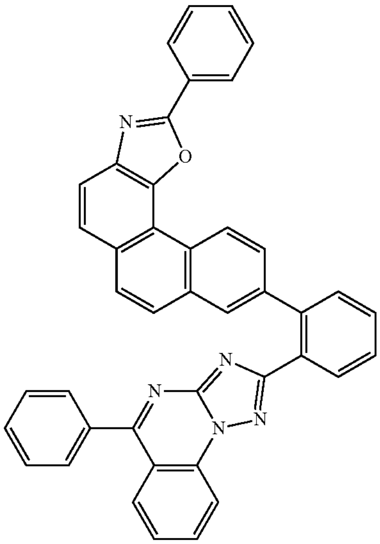
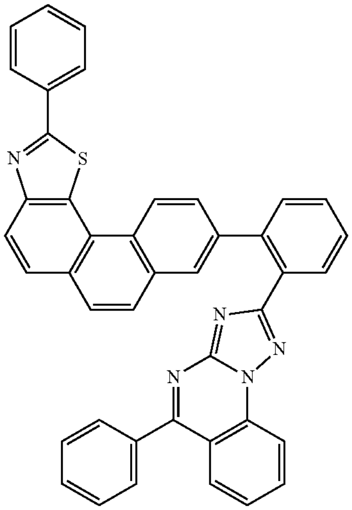

-continued
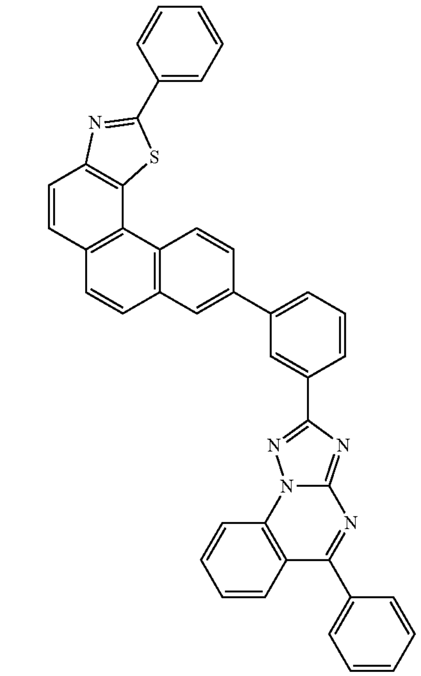
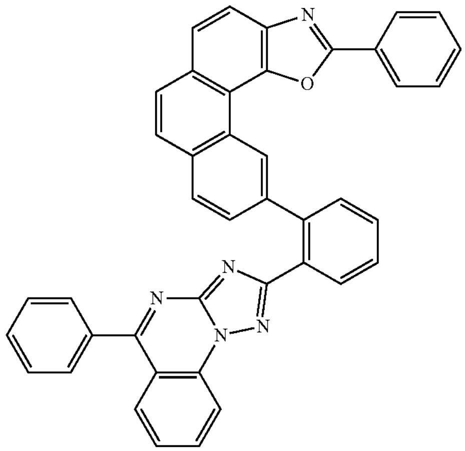
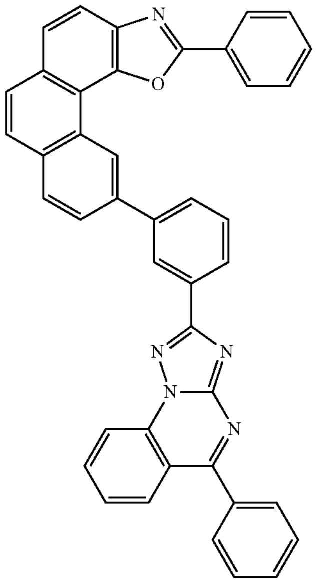
-continued
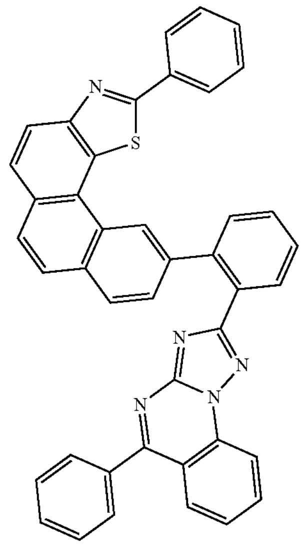
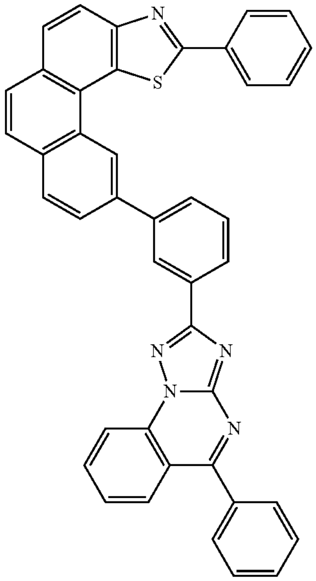

-continued
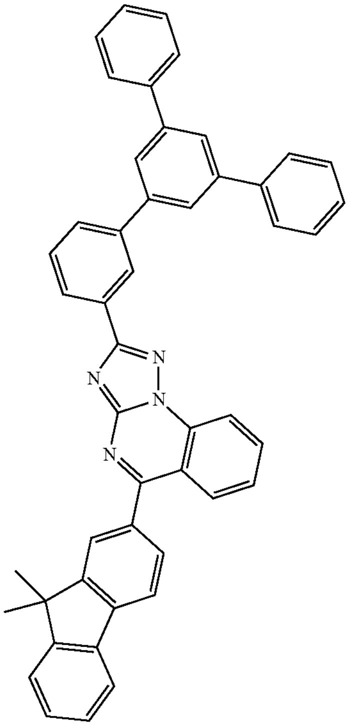
-continued
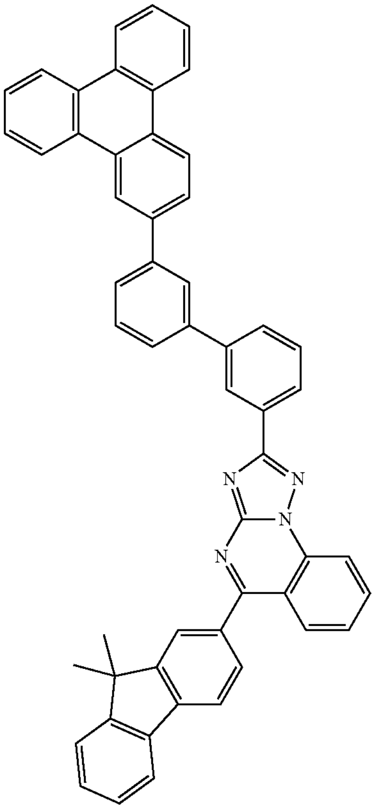
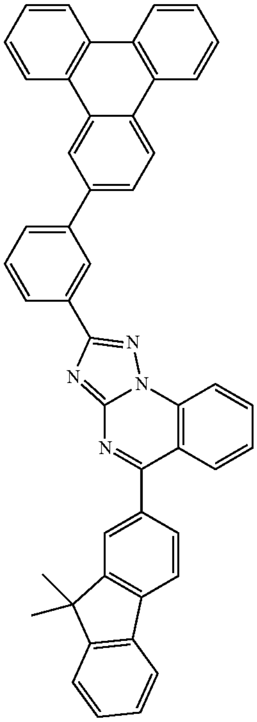
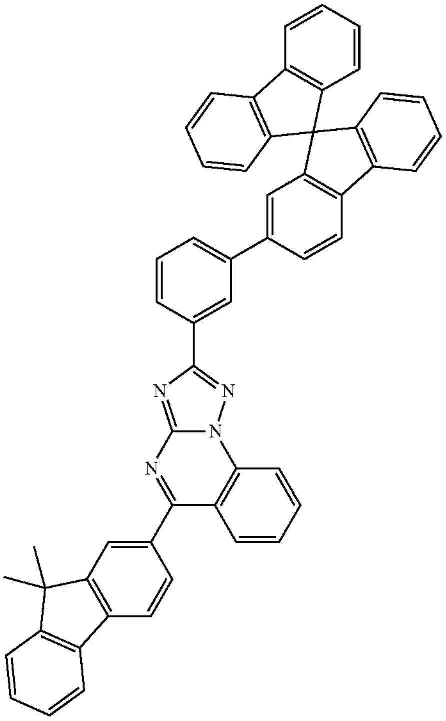

-continued
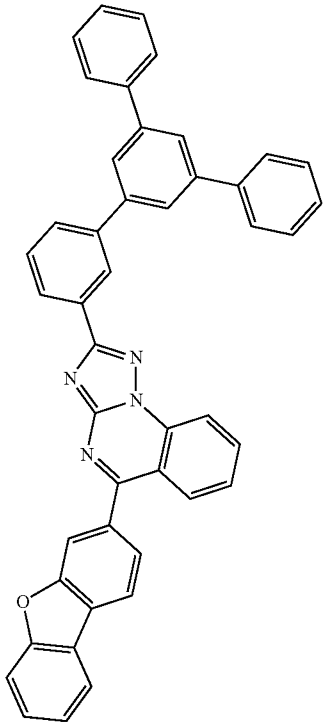
-continued
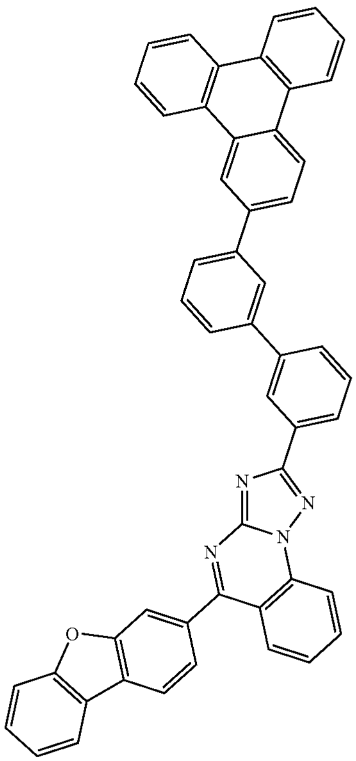
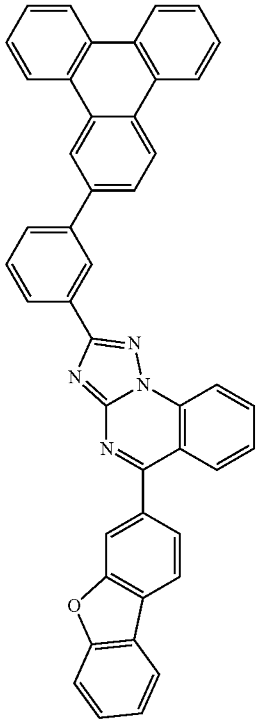
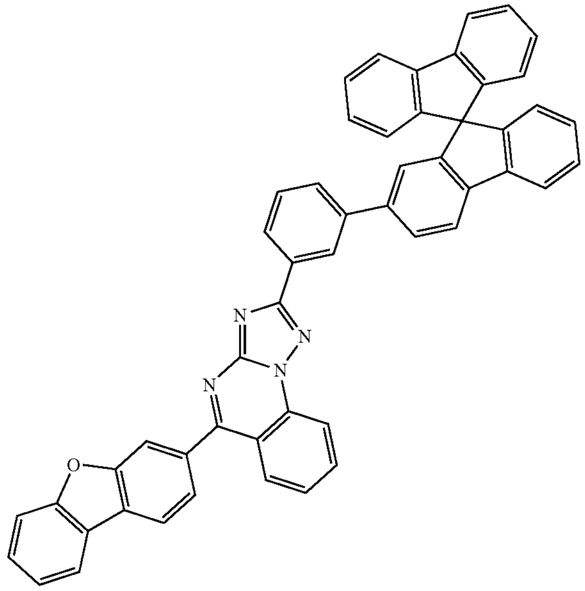

-continued
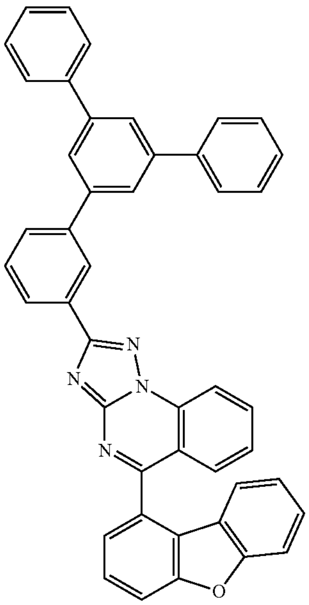
-continued
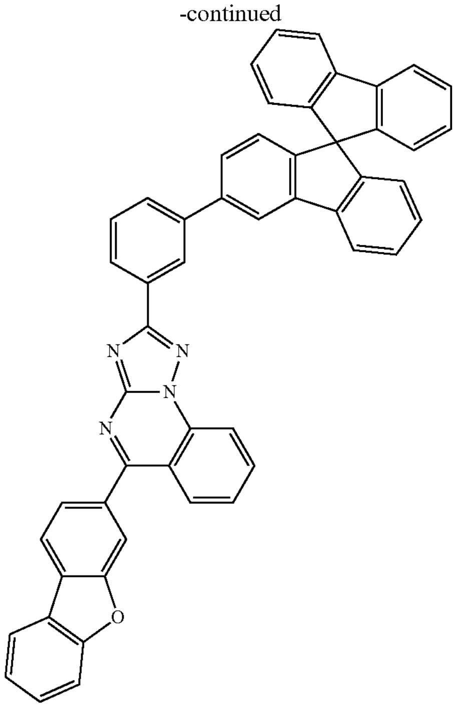
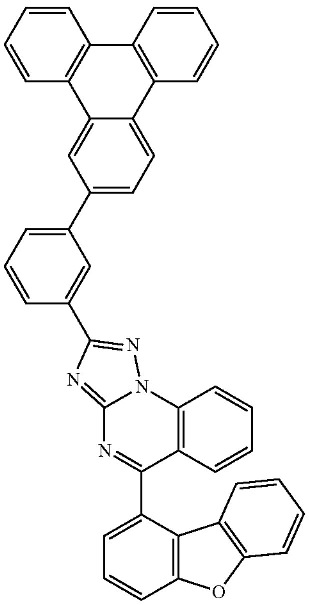
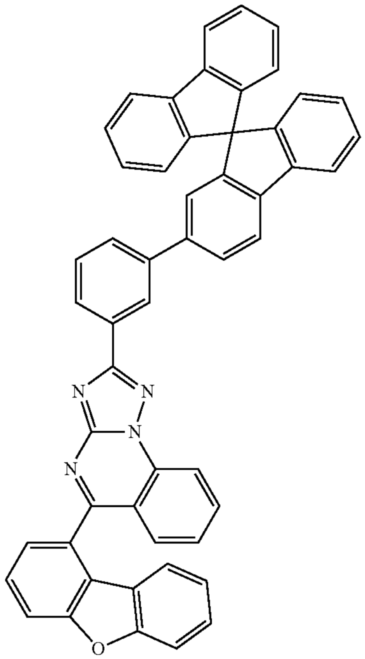

-continued
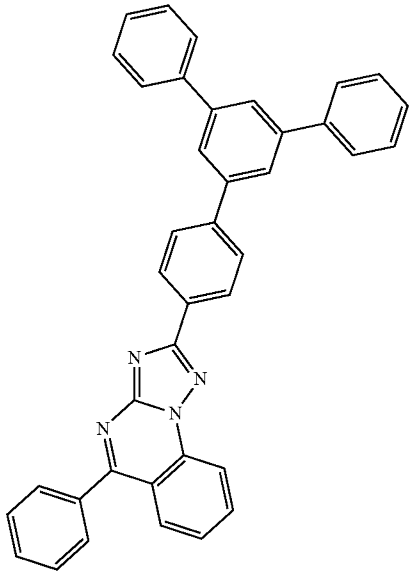
-continued
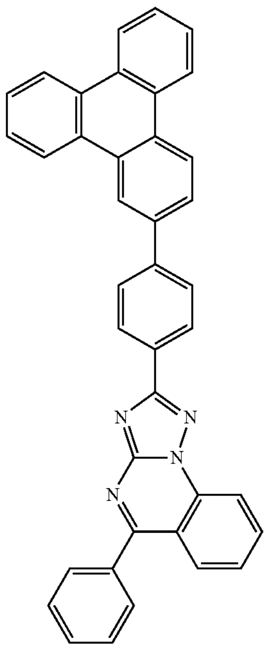
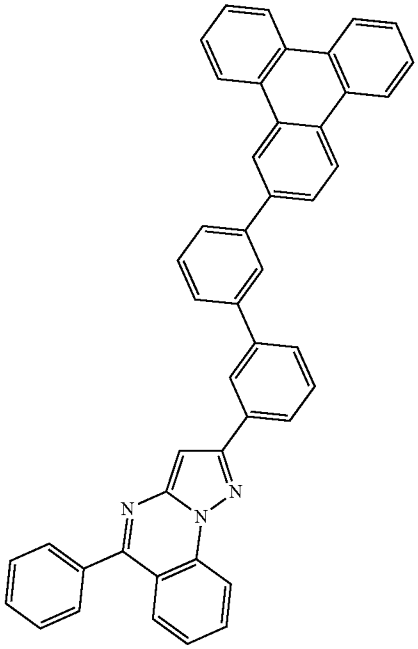
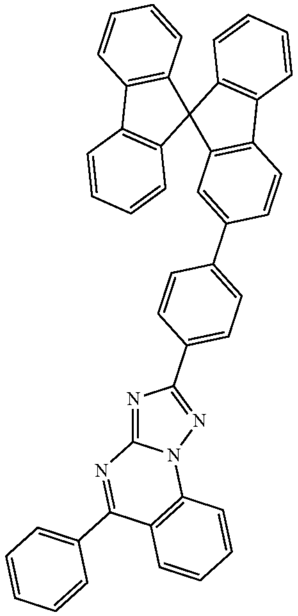

-continued
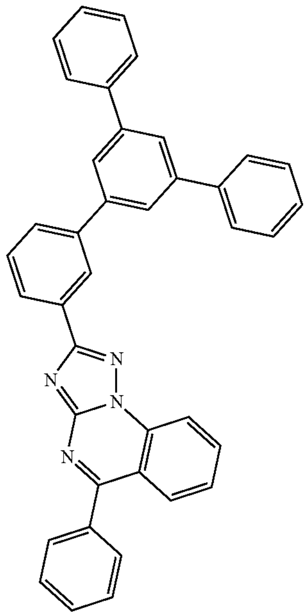
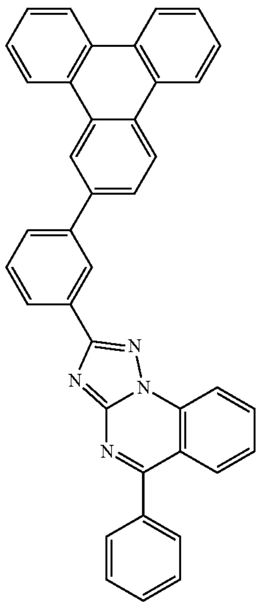
-continued
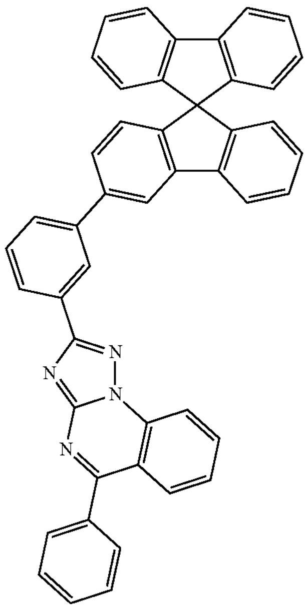
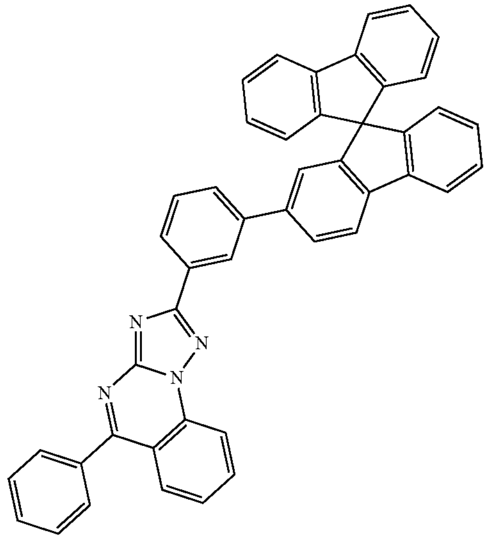
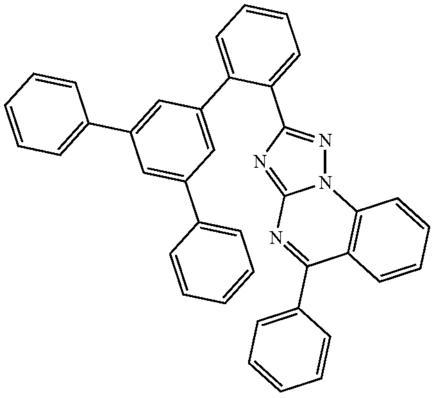

-continued
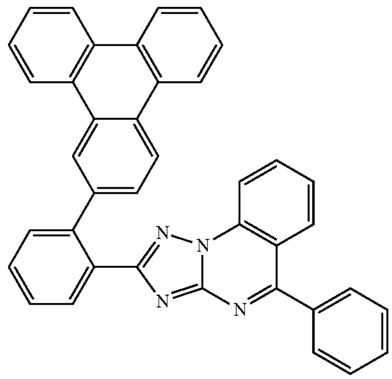
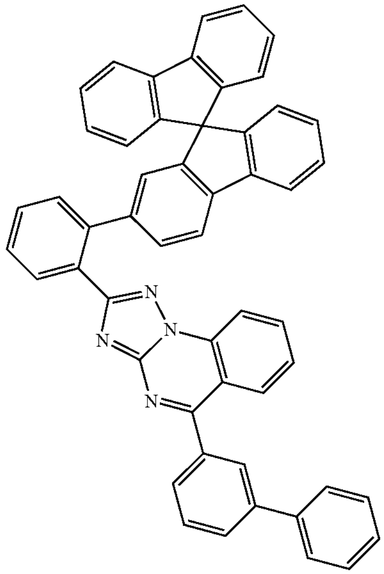
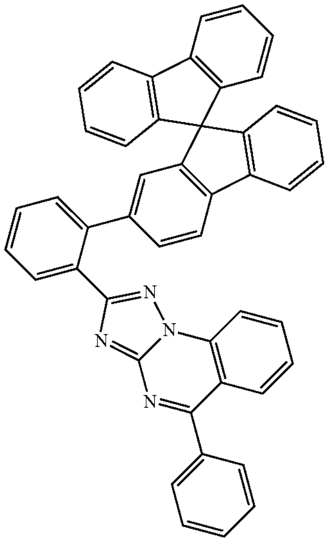
-continued
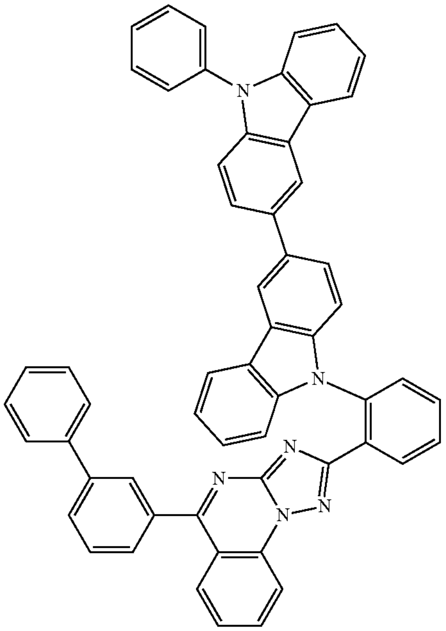
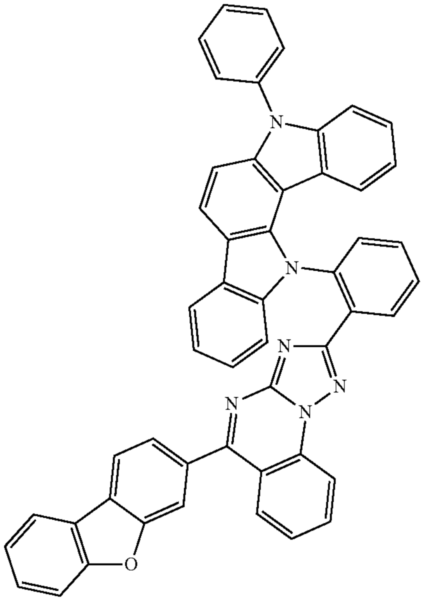
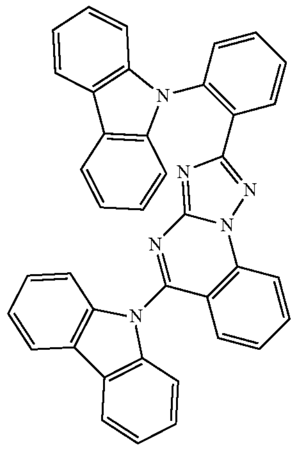

-continued
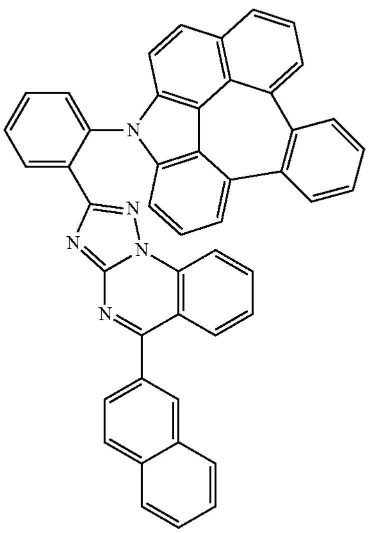
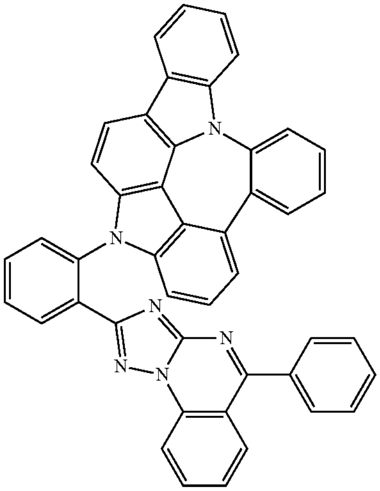
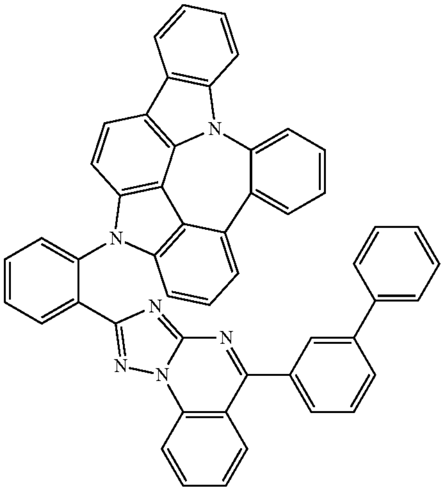
-continued
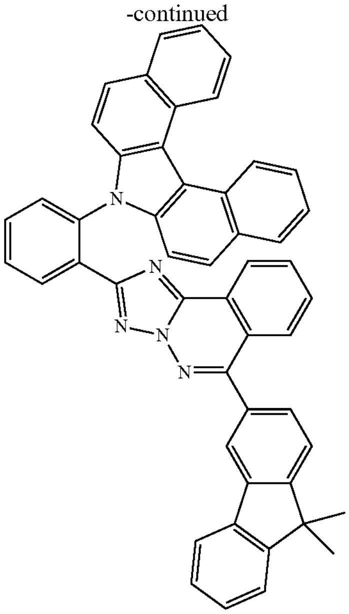
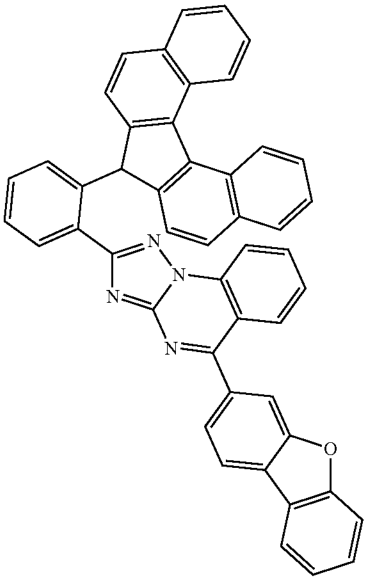

-continued
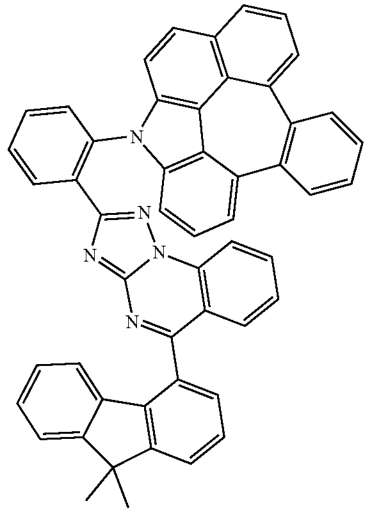
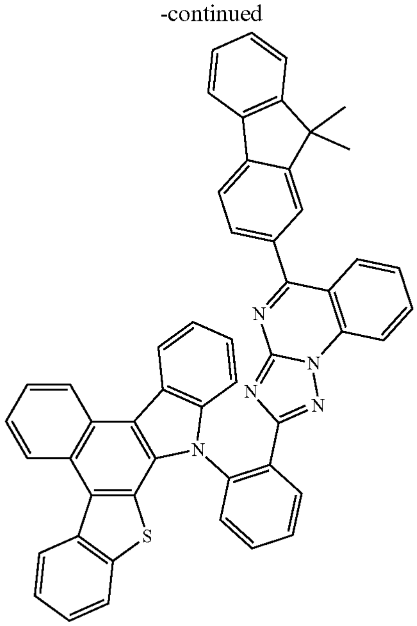
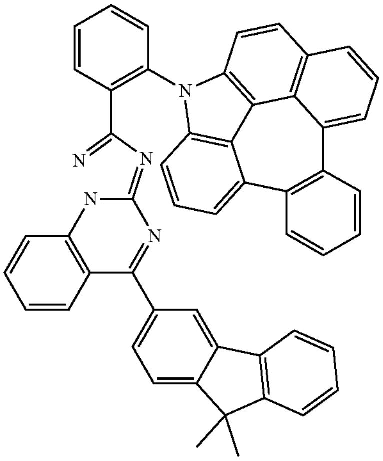
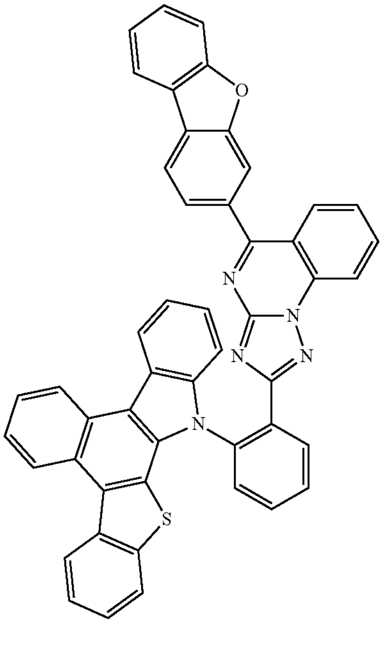
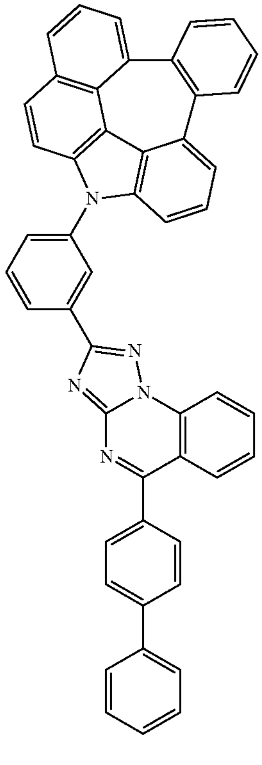

-continued
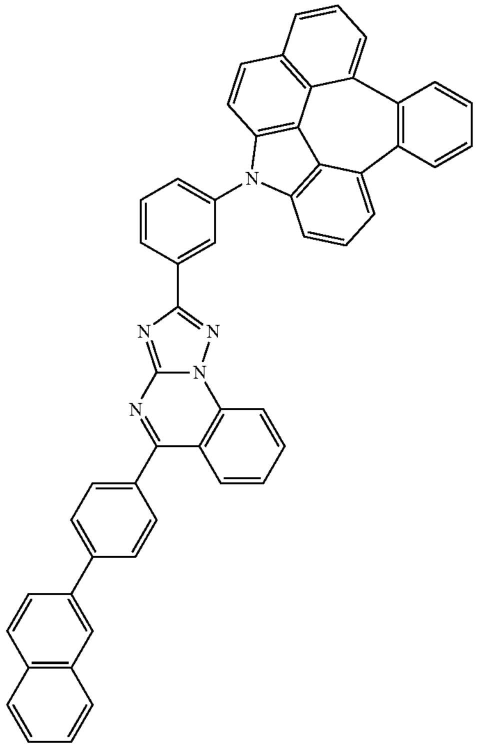
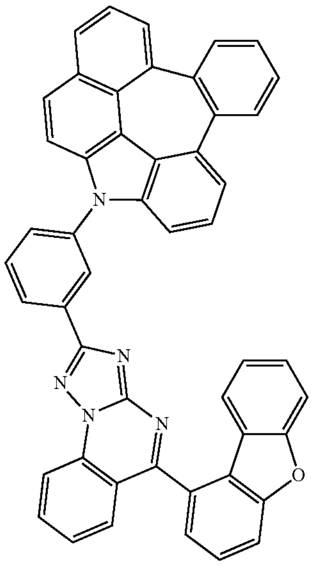
-continued
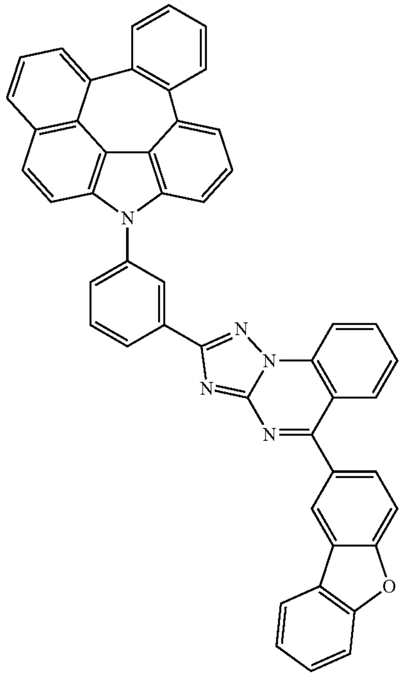
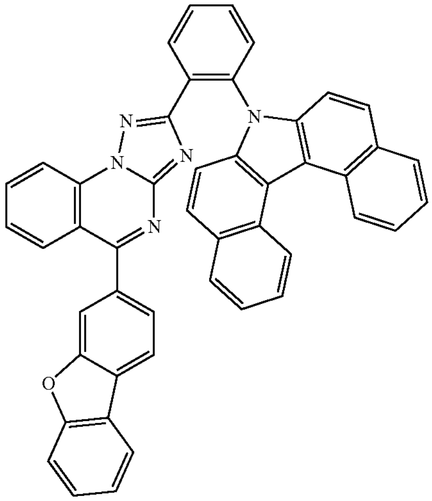
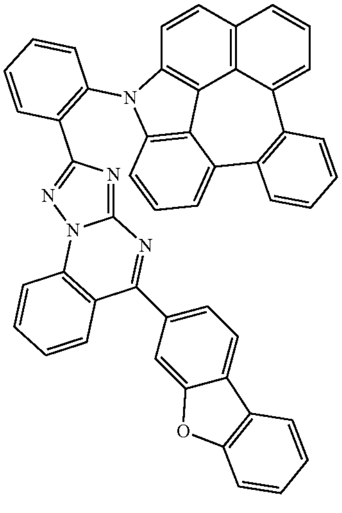

-continued
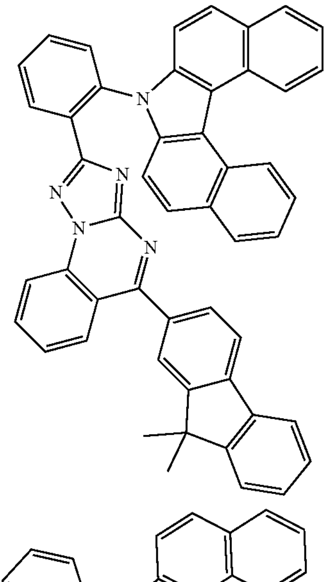
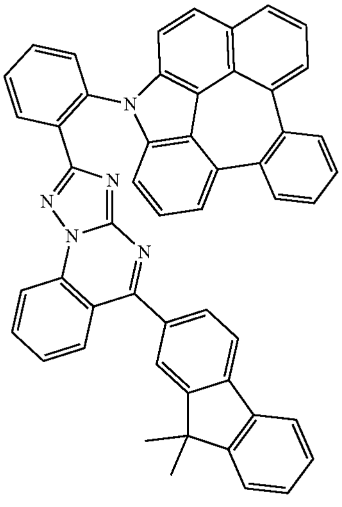
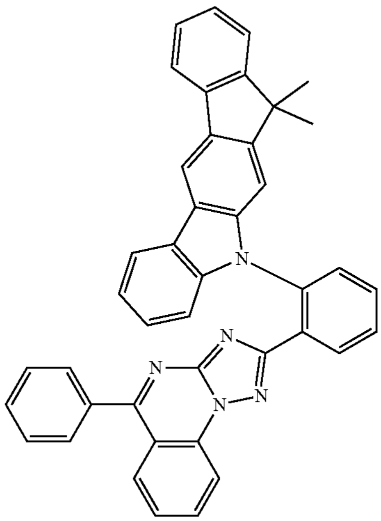
-continued
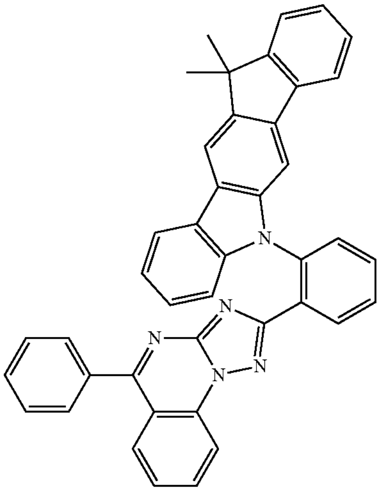
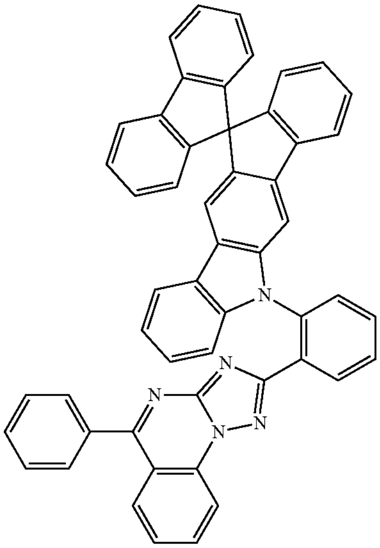
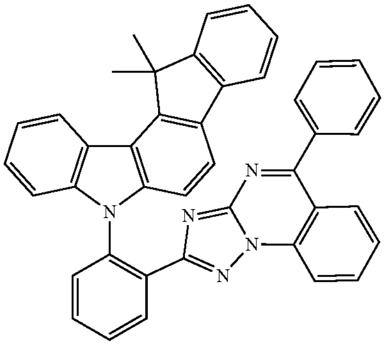

-continued
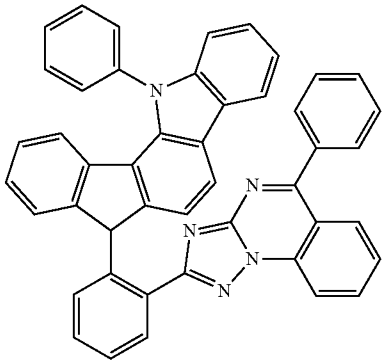
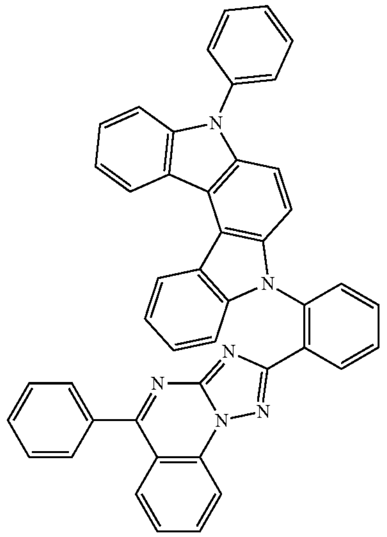
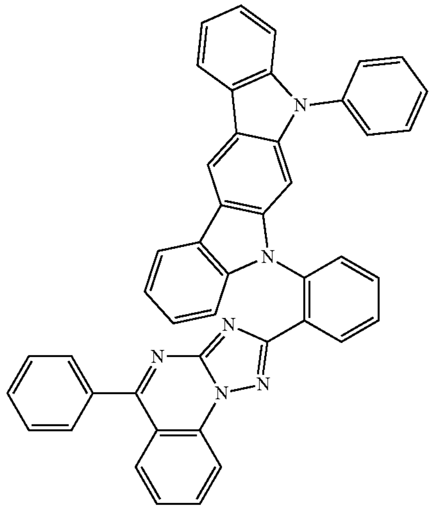
-continued
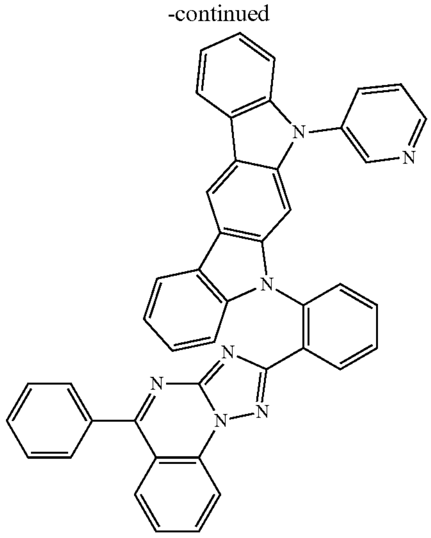
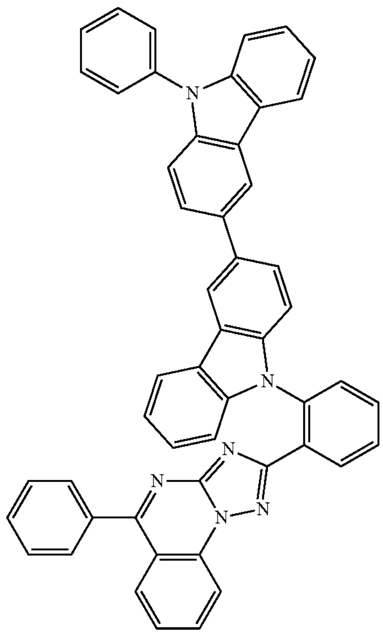

-continued
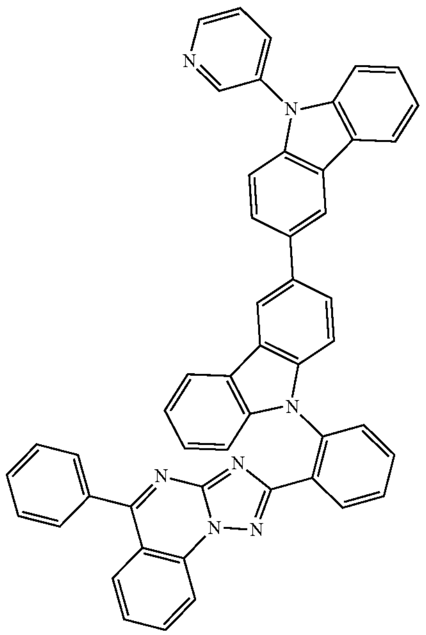
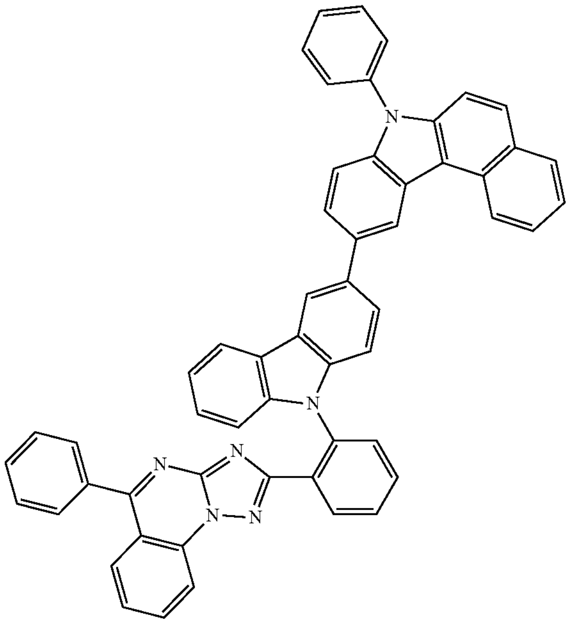
-continued
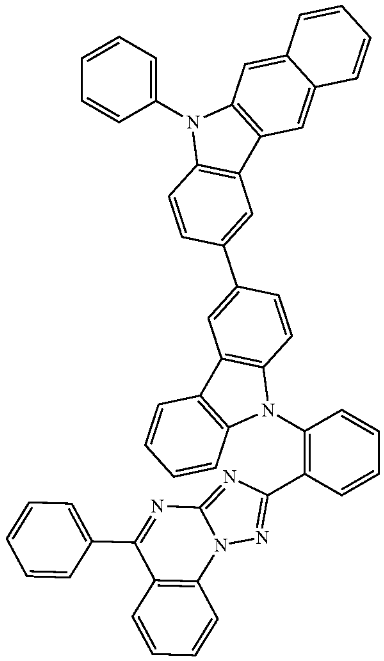
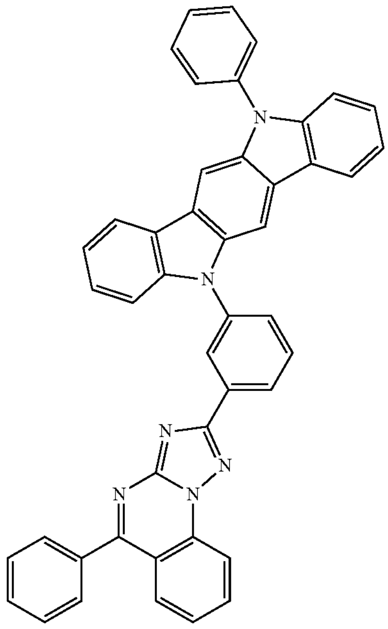

-continued
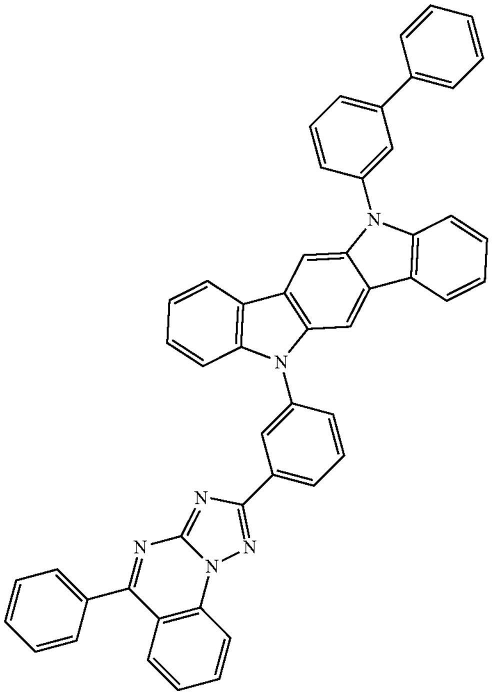
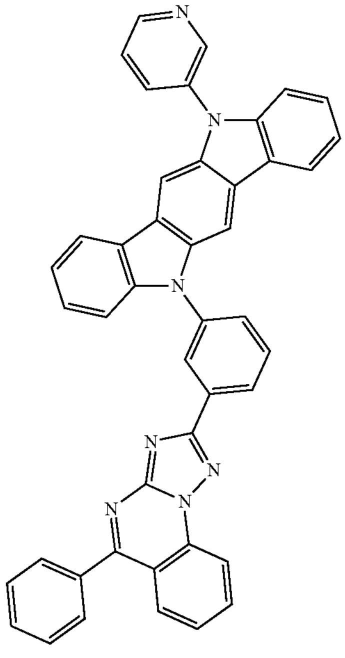
-continued
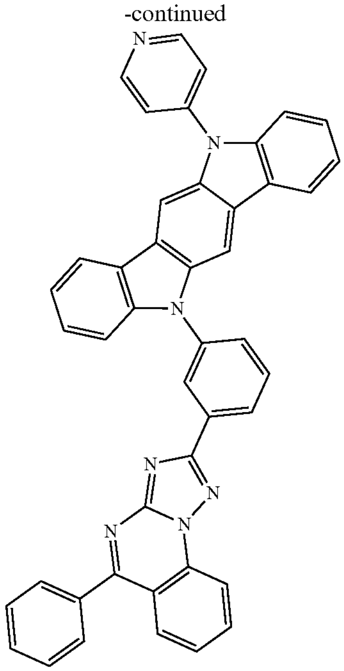
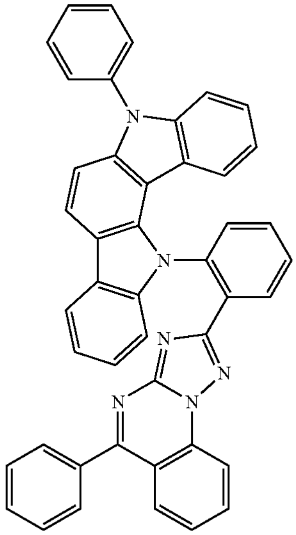
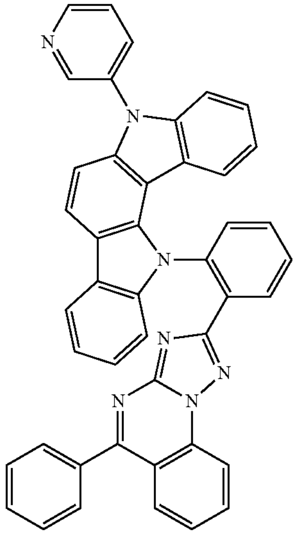

-continued
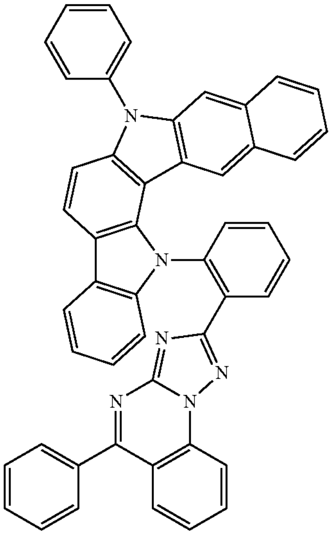
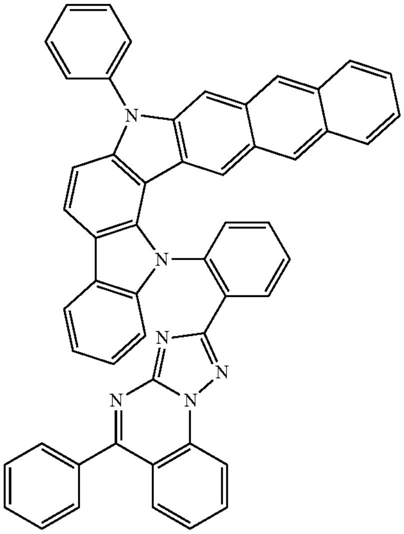
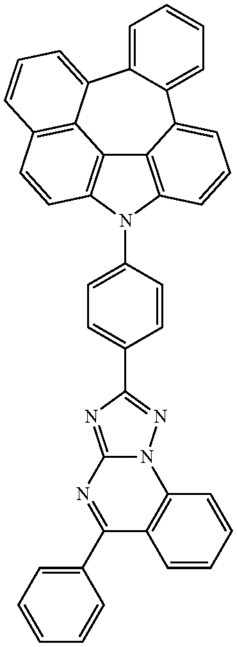
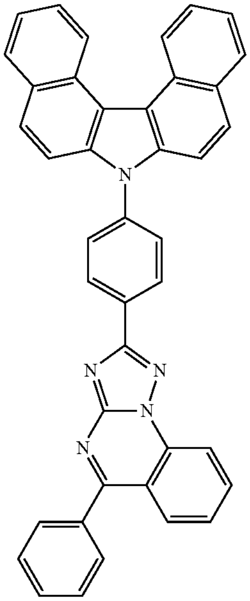
-continued
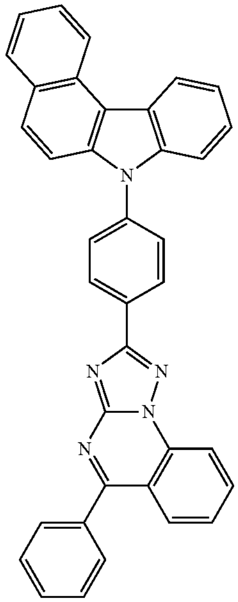
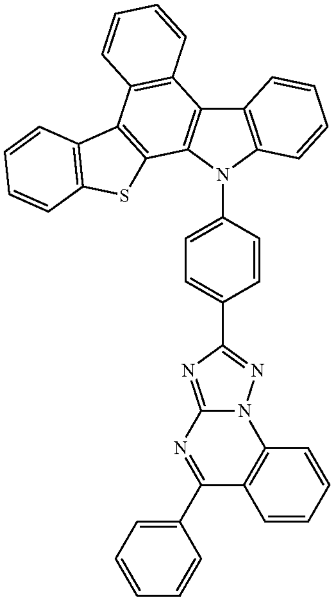
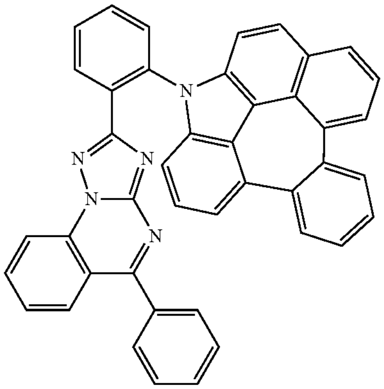

-continued
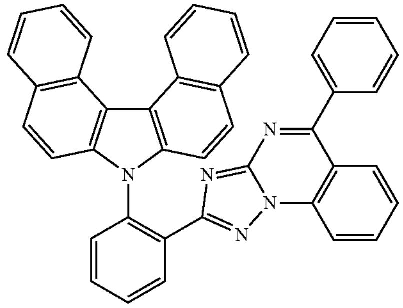
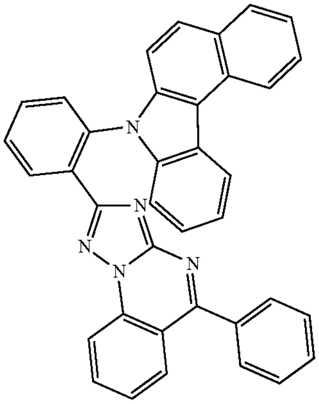
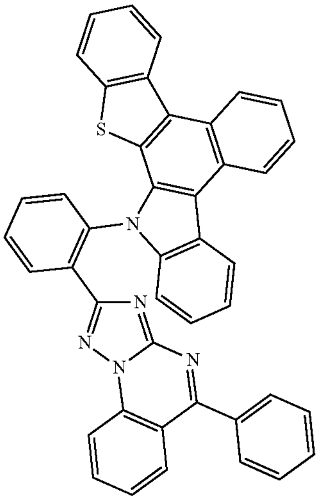
-continued
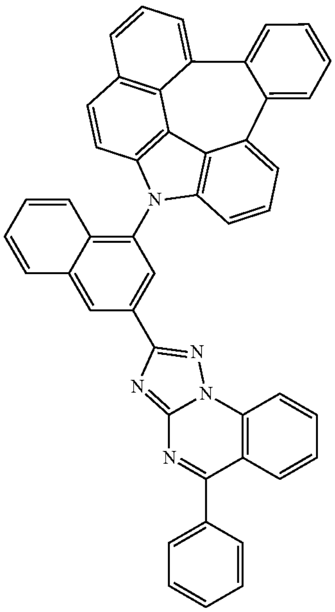
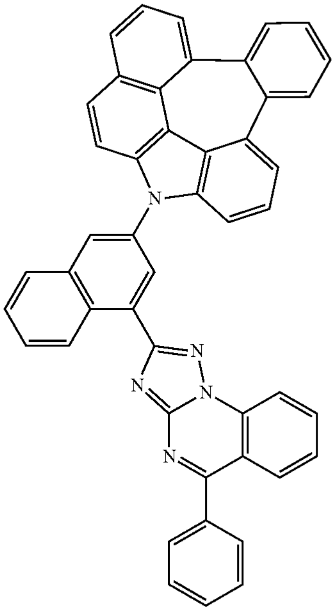

-continued
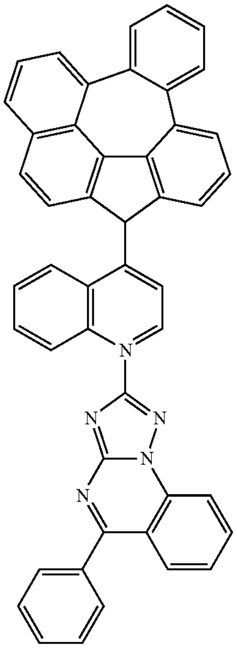
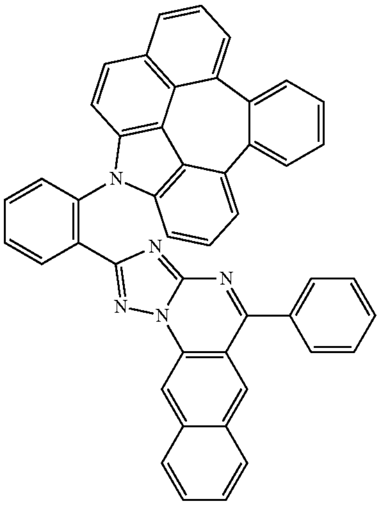
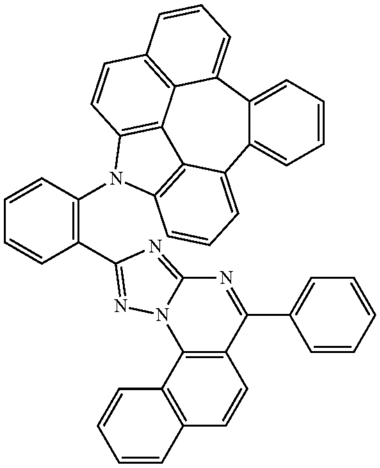
-continued
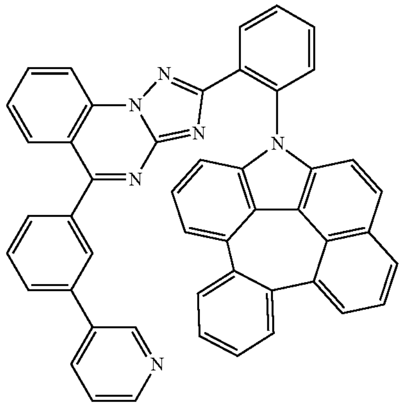
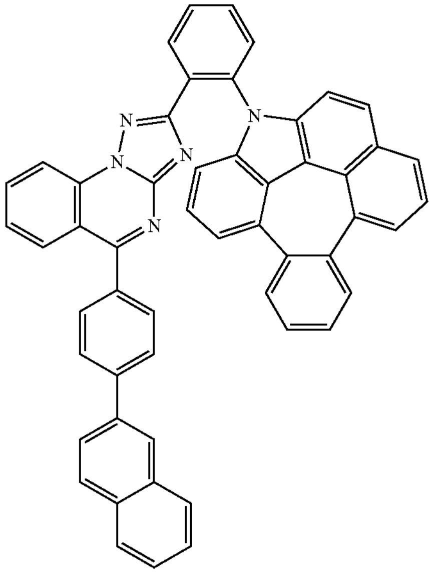
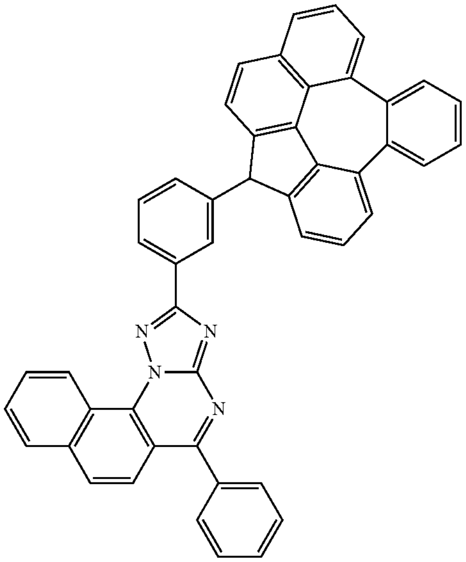

-continued
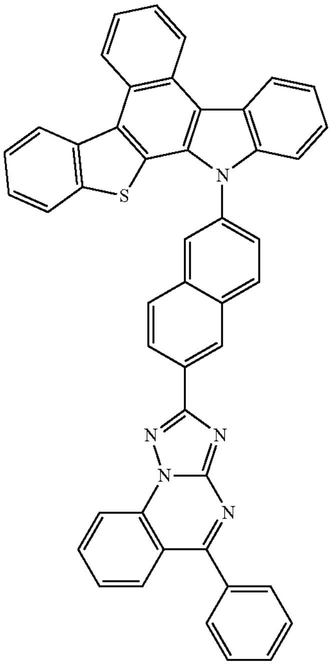
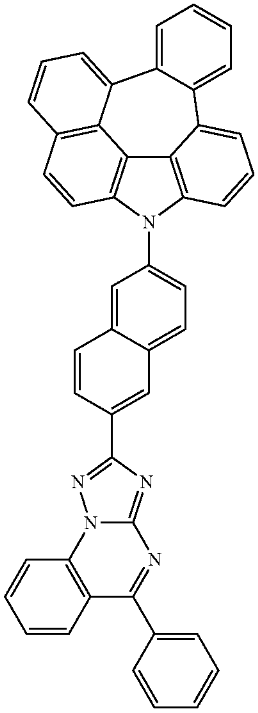
-continued
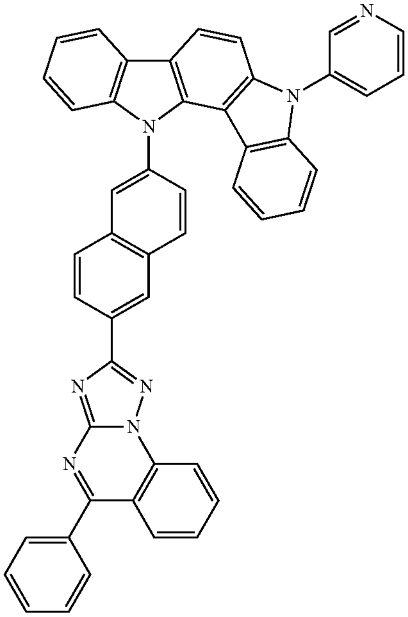
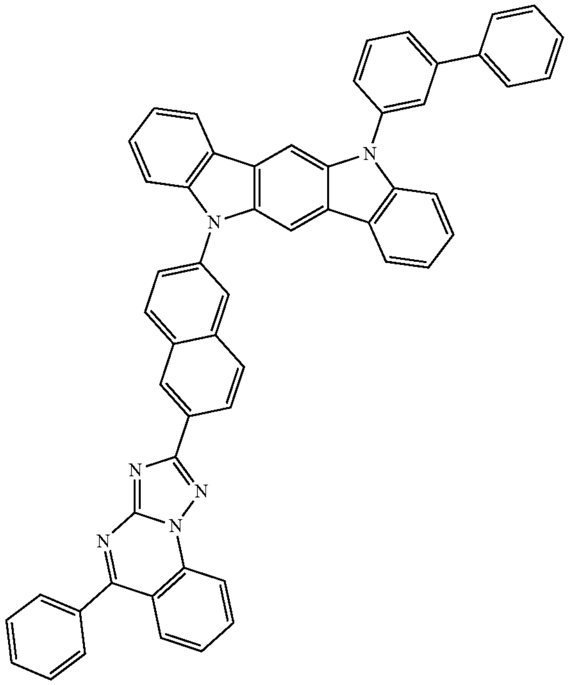

-continued
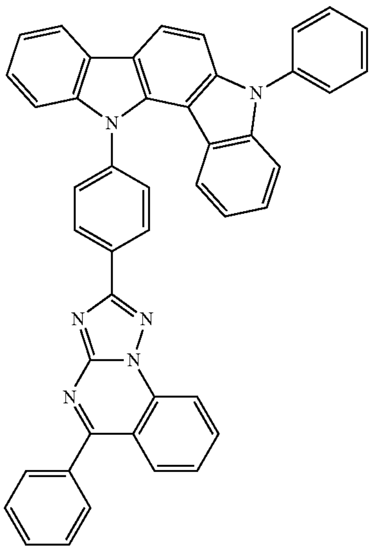
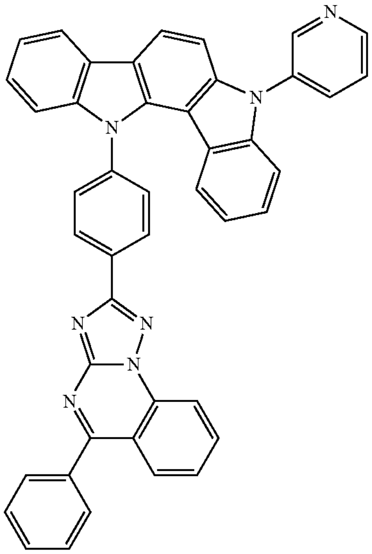
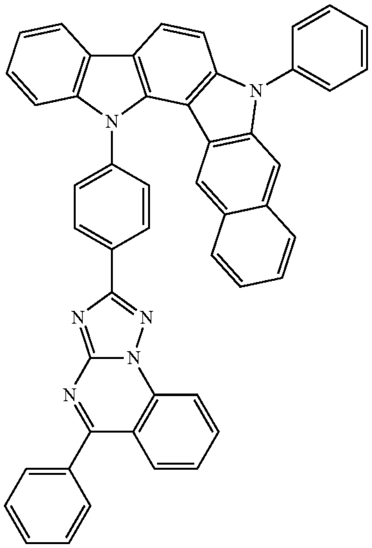
-continued
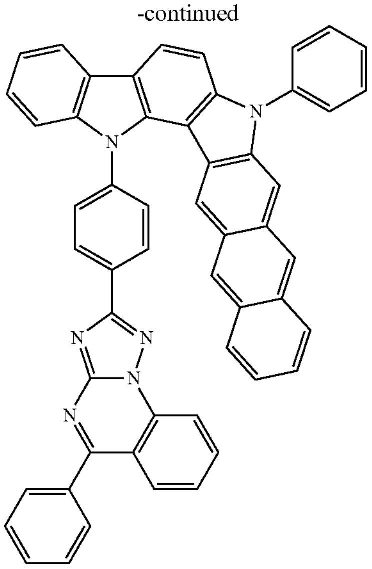
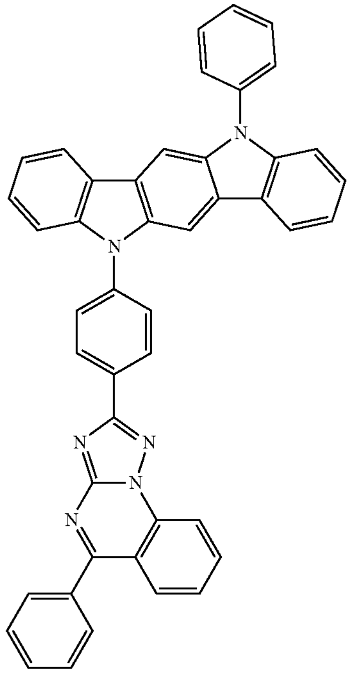

-continued
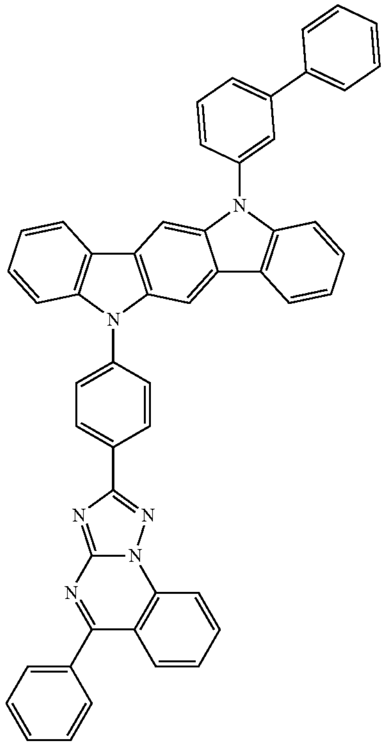
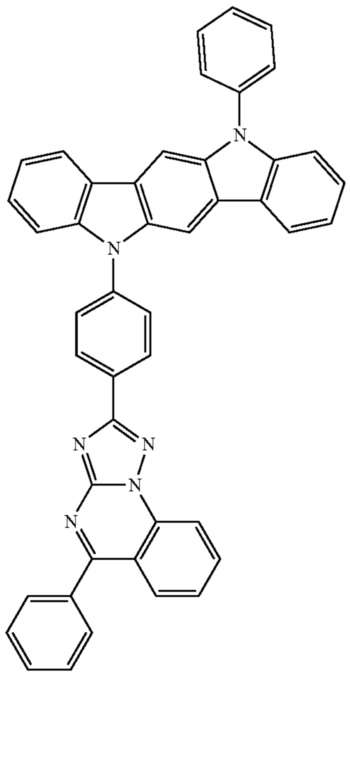
-continued
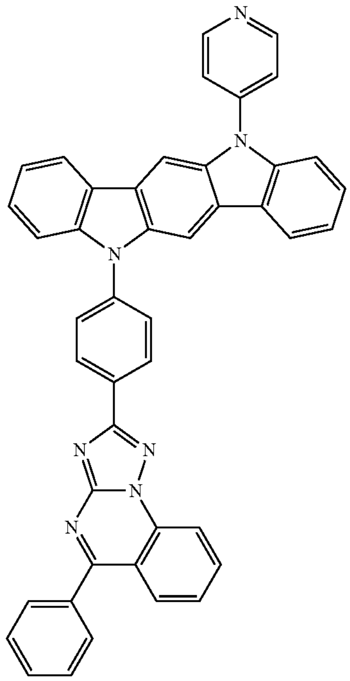
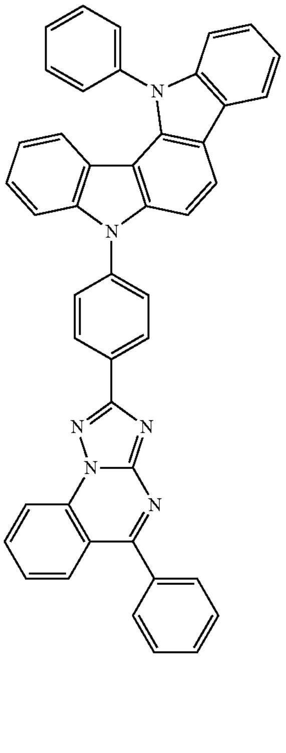

-continued
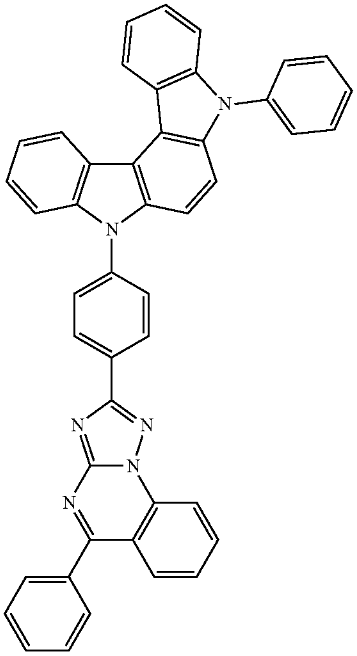
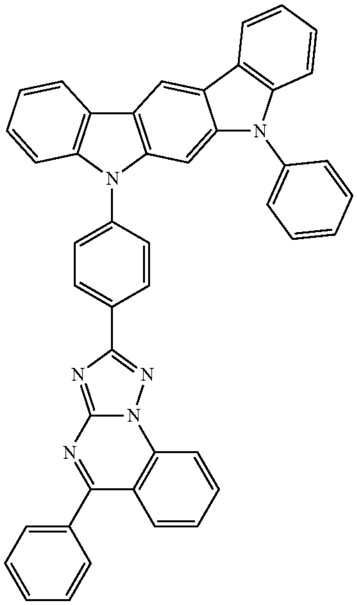
-continued
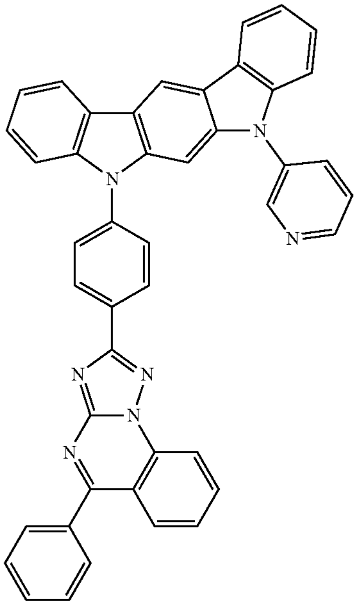
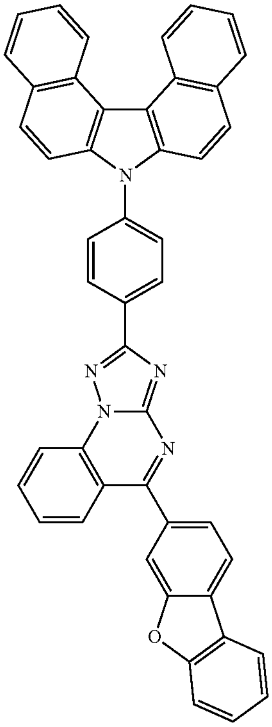

-continued
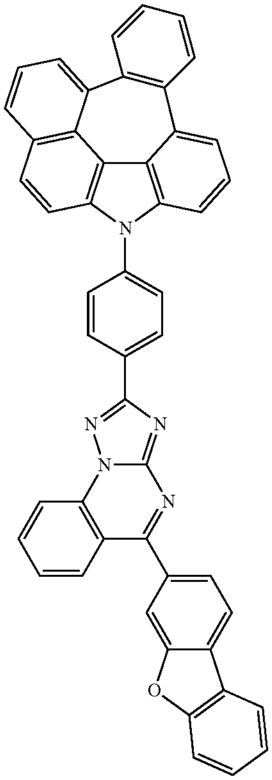
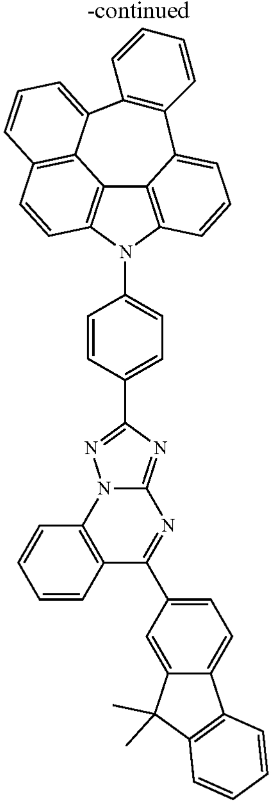
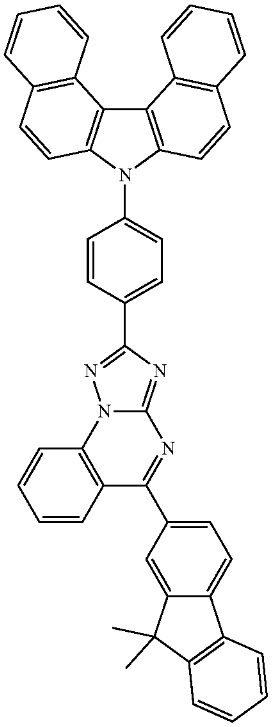
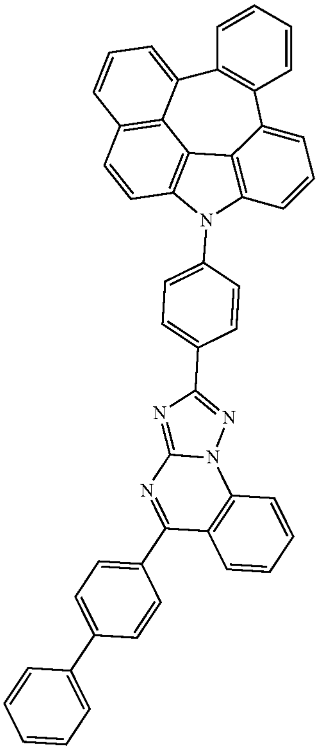

-continued
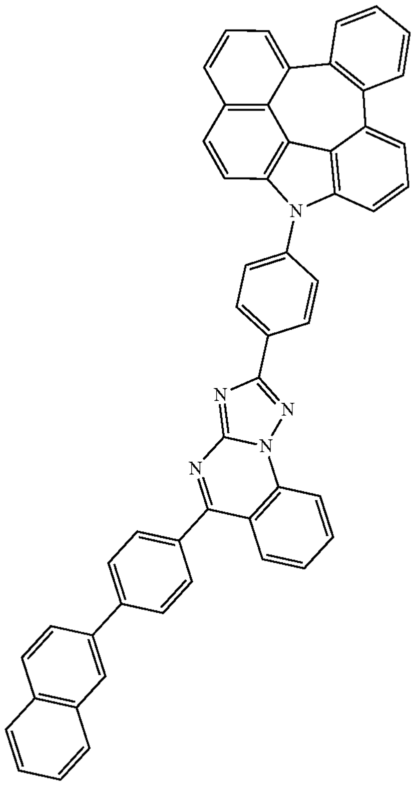
-continued
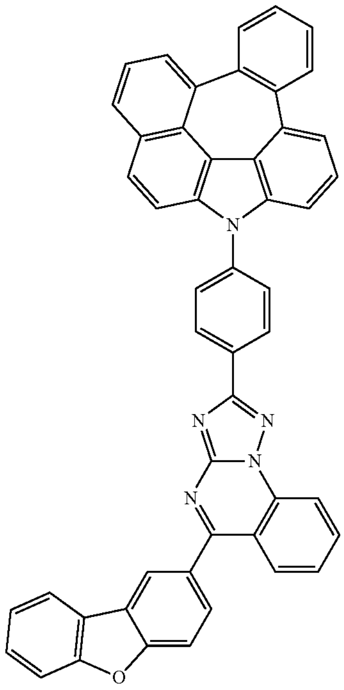
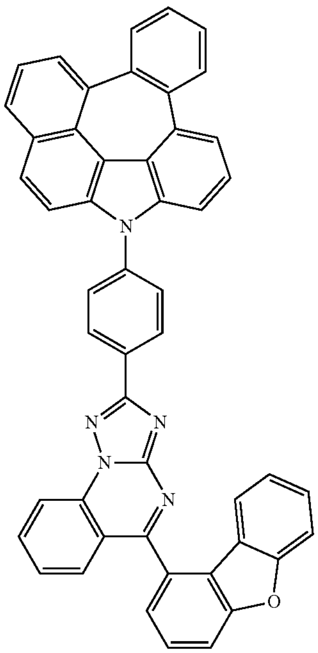
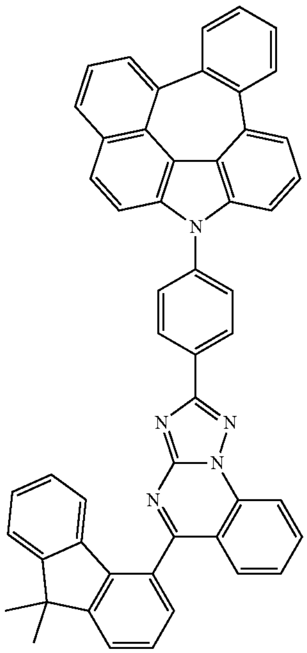

-continued
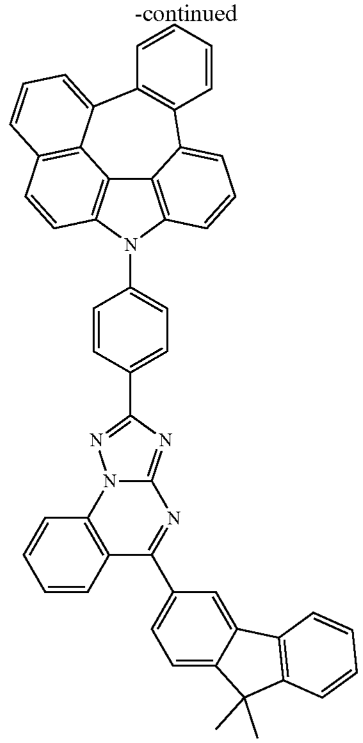
-continued
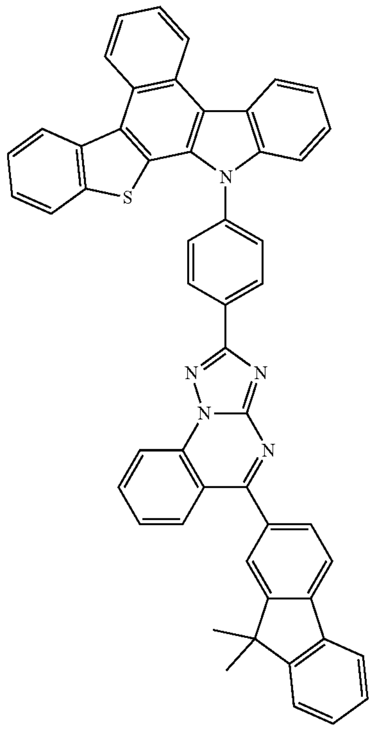
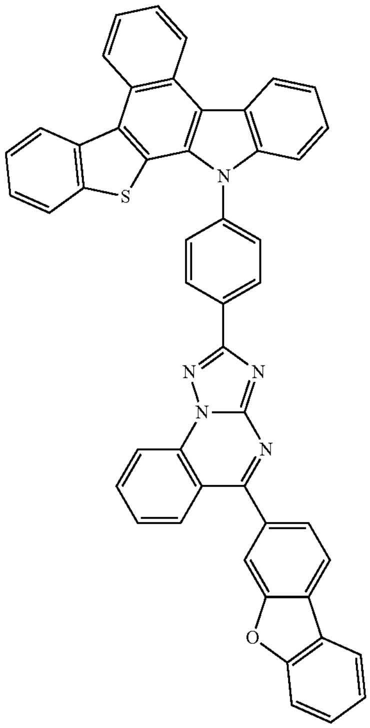
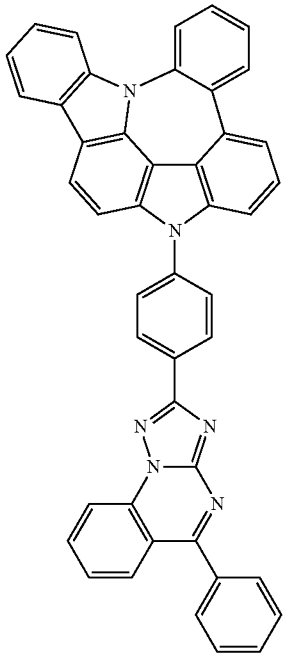

-continued
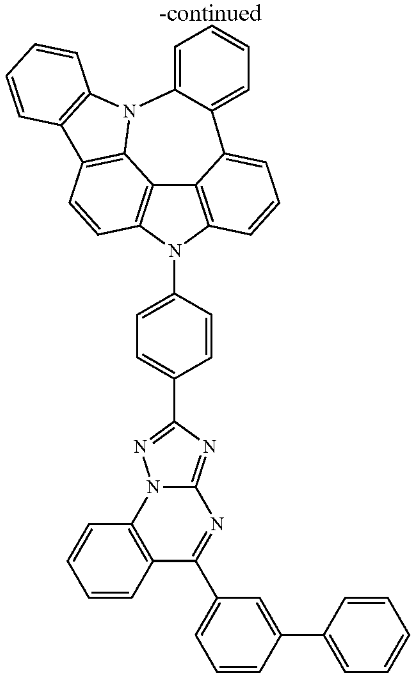
-continued
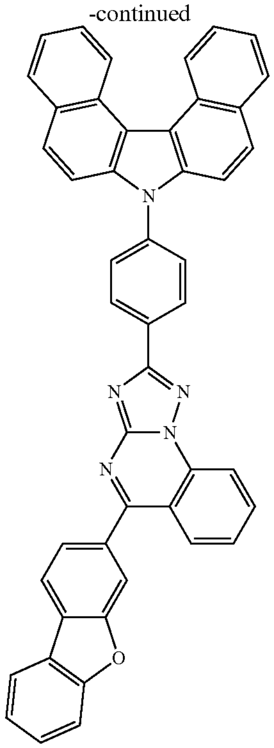
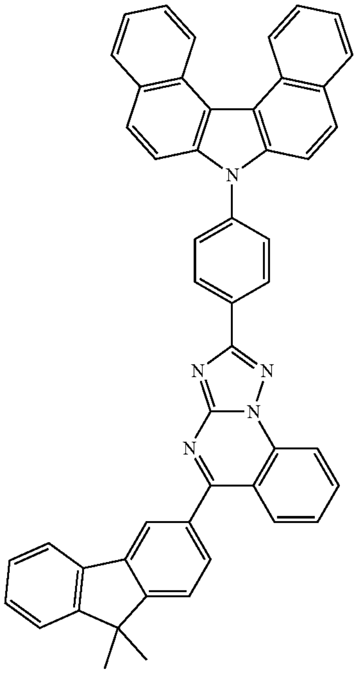
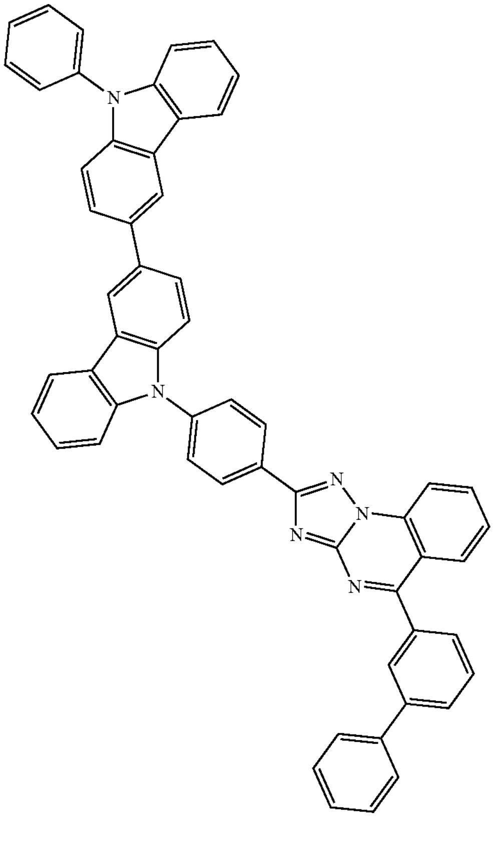

-continued

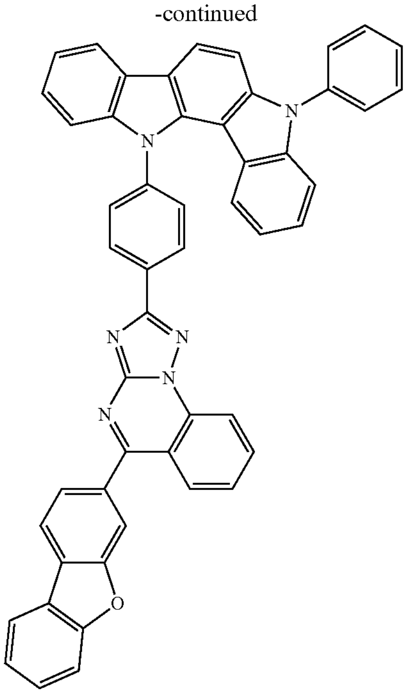

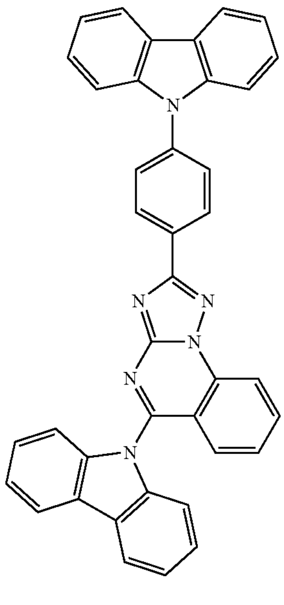

and

-continued

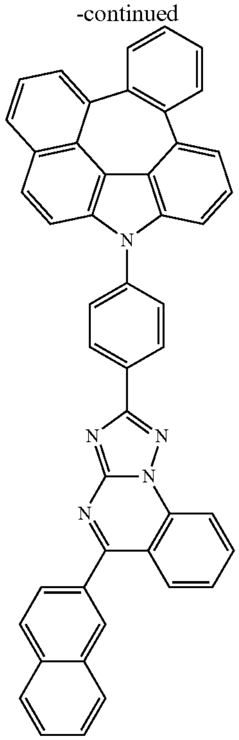

.

The alkyl group described in the present invention may be any one of straight and branched alkyl groups. Optionally, the alkyl group comprises, but is not limited to, methyl ethyl, propyl, isopropyl, butyl, 2-butyl, isobutyl or tert-butyl.

The cycloalkyl group described in the present invention comprises, but is not limited to, cyclopropyl, cyclobutyl, cyclohexyl.

The alkenyl group described in the present invention indicates a monovalent substituent derived from a straight or branched unsaturated hydrocarbon having one or more C—C double bonds and a carbon number of 2 to 40, which comprises, but is not limited to, for example, an ethenyl group, an allyl group, an isopropenyl group, a 2-butenyl group, or the like.

The aryl group described in the present invention comprises monocyclic, multicyclic, fused cyclic aryl groups, and the rings may be interrupted by a short non-aromatic unit (such as a methylene group). The aryl group is selected from a phenyl group, a biphenylyl group, a terphenylyl group, a naphthyl group, a binaphthylyl group, a phenylnaphthyl group, a naphthylphenyl group, a fluorenyl group, a phenylfluorenyl group, a benzofluorenyl group, a dibenzofluorenyl group, a phenanthryl group, a phenylphenanthryl group, an anthryl group, an indenyl, a terphenylenyl group, a pyrenyl group, a tetracenyl group, a perylenyl group, a chrysenyl group, a naphthacenyl group, a fluoranthenyl group, and a spiro-bifluorenyl group.

The heteroaryl group described in the present invention comprises monocyclic, multicyclic, fused cyclic heteroaryl groups, and the rings may be interrupted by a short non-aromatic unit (such as a methylene group, O, S, N). The heteroaryl group is selected from a furyl group, a thiophenyl group, a pyrrolyl group, a imidazolyl group, a pyrazolyl group, a thiazolyl group, a thiadiazolyl group, an isothiazolyl group, an isoxazolyl group, an oxazolyl group, an oxadizolyl group, a triazinyl group, a tetrazinyl group, a triazolyl group, a tetrazolyl group, a furazanyl group, a pyridyl group, a pyrazinyl group, a pyrimidinyl group, a pyridazinyl group, a benzofuryl group, a benzothiophenyl group, an isobenzofuryl group, a dibenzofuryl group, a dibenzothiophenyl group, a benzimidazolyl group, a benzothiazolyl group, a benzisothiazolyl group, a benzisoxazolyl group, a benzoxazolyl group, an isoindolyl group, an indolyl group, an indazolyl group, a benzothiadiazolyl group, a quinolyl group, an isoquinolyl group, a cinnolinyl group, a quinazolinyl group, a quinoxalinyl group, a carbazolyl group, a phenoxazinyl group, a phenothiazinyl group, a phenanthridinyl group, a 1,3-benzodioxolyl group, and a dihydroacridinyl group.

The term "substituted" indicates a hydrogen atom comprised in a compound is replaced by another substituent. The position of substitution is not specifically limited, provided that the hydrogen at the position can be replaced by the substituent. When two or more substituents are simultaneously present, the two or more substituents can be the same or different. The above-mentioned substituent may comprise an alkyl group, a phenyl group, an aryl group, a heteroaryl group, or the like.

In the present invention, when the range of carbon number is limited in the definition of a functional group, the functional group may have a carbon number of any integer in the limited range. For example, a C6-C60 aryl group represents an aryl group that may give a carbon number of any one integer comprised in the range of 6 to 60, such as 6, 8, 10, 15, 20, 30, 35, 40, 45, 50, 55 or 60, etc.

In the present invention, the nitrogen-containing fused heterocyclic compound having a structure represented by Formula (1) can be prepared by a route shown as below:

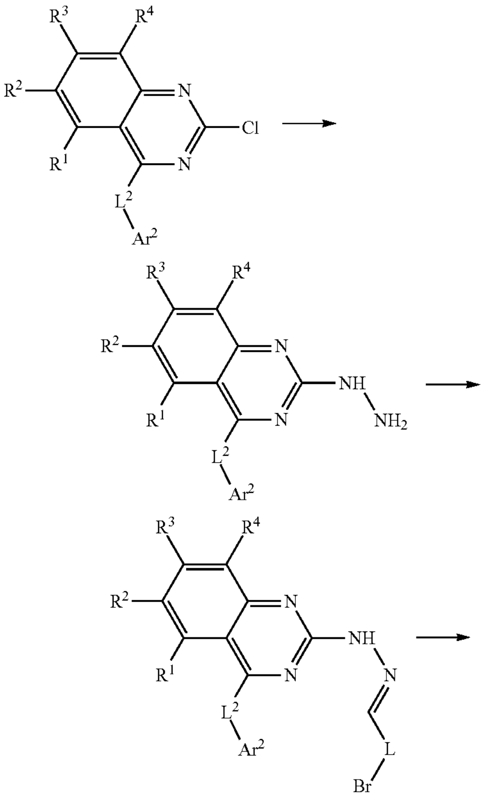

-continued

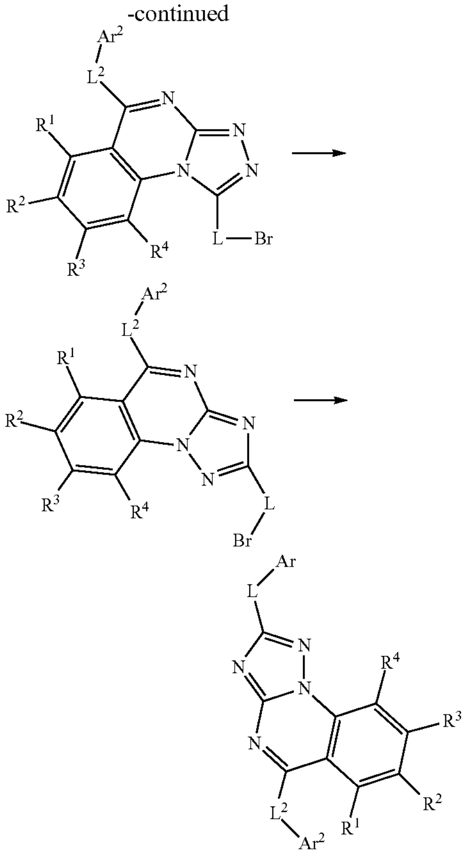

In another aspect, the present invention provides an application of the above-mentioned nitrogen-containing fused heterocyclic compound in preparation of an optical element.

Preferably, the optical element comprises any one of an organic electroluminescence element, an organic field-effect transistor, an organic thin film transistor, an organic light-emitting transistor, an organic integrated circuit, an organic solar cell, an organic field quenching element, a light-emitting electrochemical cell, an organic laser diode, and an organic photoreceptor.

In another aspect, the present invention provides an organic electroluminescence element, the organic electroluminescence element comprises an anode, a cathode, and an organic layer disposed between the anode and the cathode, the organic layer comprises any of the above-mentioned nitrogen-containing fused heterocyclic compounds or any of the combinations thereof.

Preferably, the organic layer comprises a hole injection layer, a hole transport layer, an emitting layer, an electron transport layer and an electron injection layer, which are sequentially layered from a side of the anode to a side of the cathode.

Preferably, the emitting layer is made of a material comprising a host material and a guest material, wherein the host material comprises any of the above-mentioned nitrogen-containing fused heterocyclic compounds or any of the combinations thereof.

Preferably, the guest material comprises a phosphorescence dopant, and the phosphorescence dopant comprises a coordination complex containing Ir, Os or Pt.

In another aspect, the present invention provides an organic electroluminescence device, characterized in that the organic electroluminescence device comprises the above-mentioned organic electroluminescence element. The organic electroluminescence device is a device using an organic electroluminescence element, such as a cell phone, a television, a watch or the like.

Compared to the existing technology, the present invention has the following advantages:

When the nitrogen-containing fused heterocyclic compound of the present invention is used as a host material of an emitting layer, it makes the organic light-emitting element have a lower driving voltage (3.8 V to 4.1 V), a higher current efficiency (15 Cd/A to 23 Cd/A or higher) and a longer service life (273 h or higher).

DETAILED DESCRIPTION OF THE PREFERRED EMBODIMENTS

Specific embodiments are further illustrated by the following examples to demonstrate the technical approaches of the present invention. Those skilled in the art should understand that the illustrative examples are helpful to understand the present invention; however, they should not be construed as being limiting to the scope of the present invention.

Synthesis Example 1

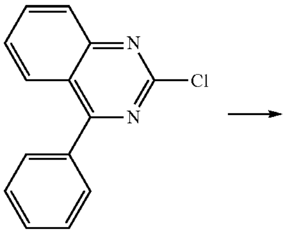

1-A

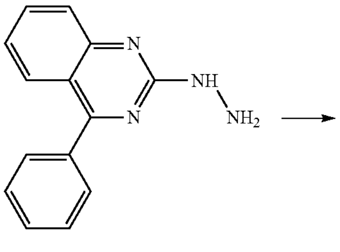

1-B

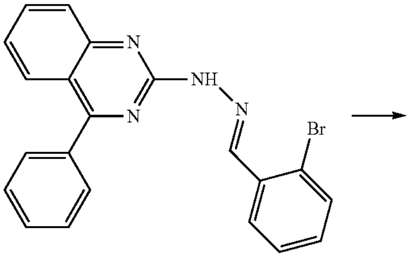

1-C

-continued

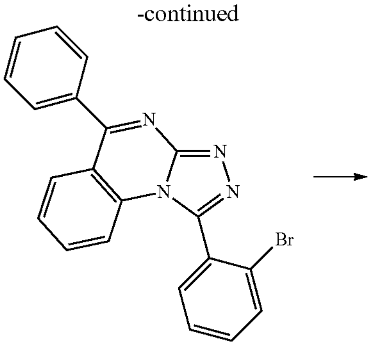

1-D

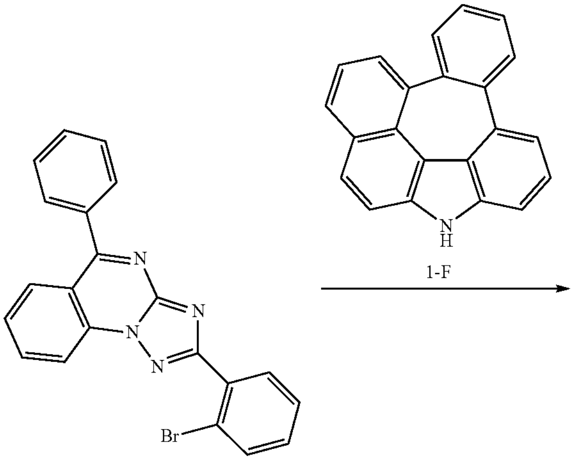

1-F

1-E

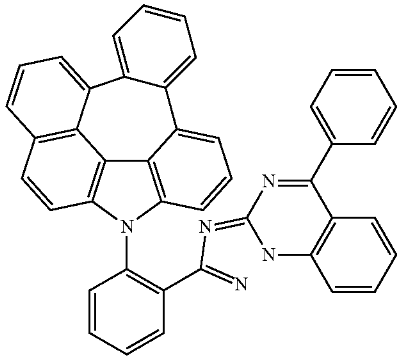

1

(1) Synthesis of 1-B: In a three-necked bottle of 50 milliliters (mL), 1-A (1 millimole (mmol)) and hydrazine hydrate (20 mL) were added, and stirred at 60° C. to react for 2 hours (h). After the reaction ended, the reaction mixture was quenched by water, extracted by methylene dichloride, and solvent was removed by rotary evaporation, to obtain 1-B.

(2) Synthesis of 1-C: In a three-necked bottle of 50 mL, the product obtained from the step (1), 2-bromobenzaldehyde (1 mmol), ethanol (20 mL) were added, and stirred at 90° C. to react for 5 h. After the reaction ended, the reaction mixture was quenched by water, extracted by methylene dichloride, dried by anhydrous magnesium sulfate, and filtered to obtain an organic phase, and then solvent was removed by rotary evaporation to give a crude product. The crude product was separated by column chromatography (ethyl acetate: n-hexane=1:10 (volume ratio)) to obtain 1-C (0.27 g, 67% yield).

(3) Synthesis of 1-D: In a three-necked bottle of 50 mL, 1-C (1 mmol), iodobenzene diacetate (2 mmol) and methylene dichloride (20 mL) were added, stirred at room temperature to react for 6 h. After the reaction ended, solvent was removed to give a crude product, and the crude product was separated by column chromatography (ethyl acetate: n-hexane=1:10 (volume ratio)), to obtain 1-D (0.25 g, 62% yield).

(4) Synthesis of 1-E: In a three-necked bottle of 50 mL, 1-D (1 mmol), potassium carbonate (2 mmol) and 1,2-dichlorobenzene (20 mL) were added, and stirred at 190° C. to react for 3 h. After the reaction ended, solvent was removed to give a crude product, and the crude product was separated by column chromatography (ethyl acetate: n-hexane=1:10 (volume ratio)), to obtain 1-E (0.28 g, 70% yield).

(5) Synthesis of Compound 1: In a two-necked round-bottom flask of 50 mL, which was dried and purged with nitrogen gas, 1-E (1 mmol), 1-F (1 mmol), caesium carbonate (0.012 mol), tris(dibenzylideneacetone)dipalladium ($Pd_2(dba)_3$, 0.05 mmol) and 2-dicyclohexylphosphino-2',4',6'-triisopropylbiphenyl (X-Phos, 0.055 mmol) were added, then toluene was added, and the mixture was refluxed for 24 h. After reaction, the mixture was cooled to room temperature, the reaction system was filtered for concentration to give a crude product, and the crude product was purified by column chromatography (methylene dichloride: n-hexane=1:10 (volume ratio)), to obtain Compound 1 (0.49 g, 80% yield).

HRMS-ESI m/z [M+H]+: 612.17.

Anal. Calcd. for $C_{43}H_{25}N_5$: C, 84.43; H, 4.12; N, 11.45. Found: C, 84.50; H, 4.10; N, 11.40.

Synthesis Example 2

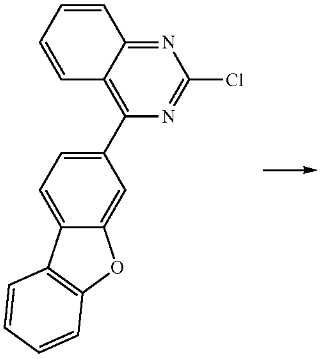

2-A

-continued

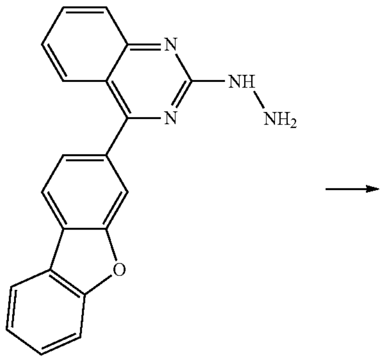

2-B

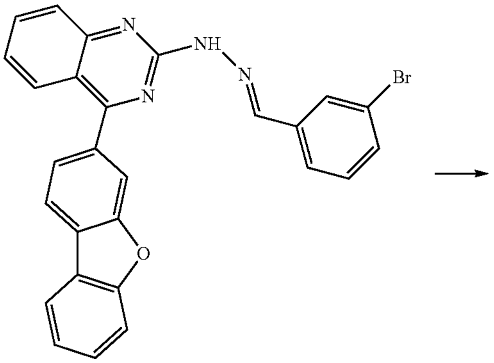

2-C

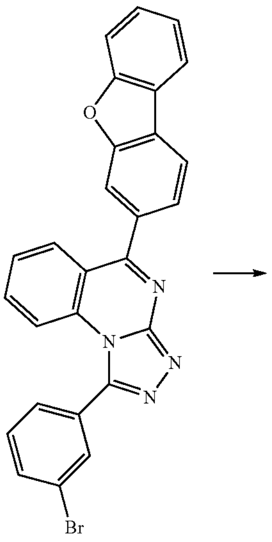

2-D

-continued

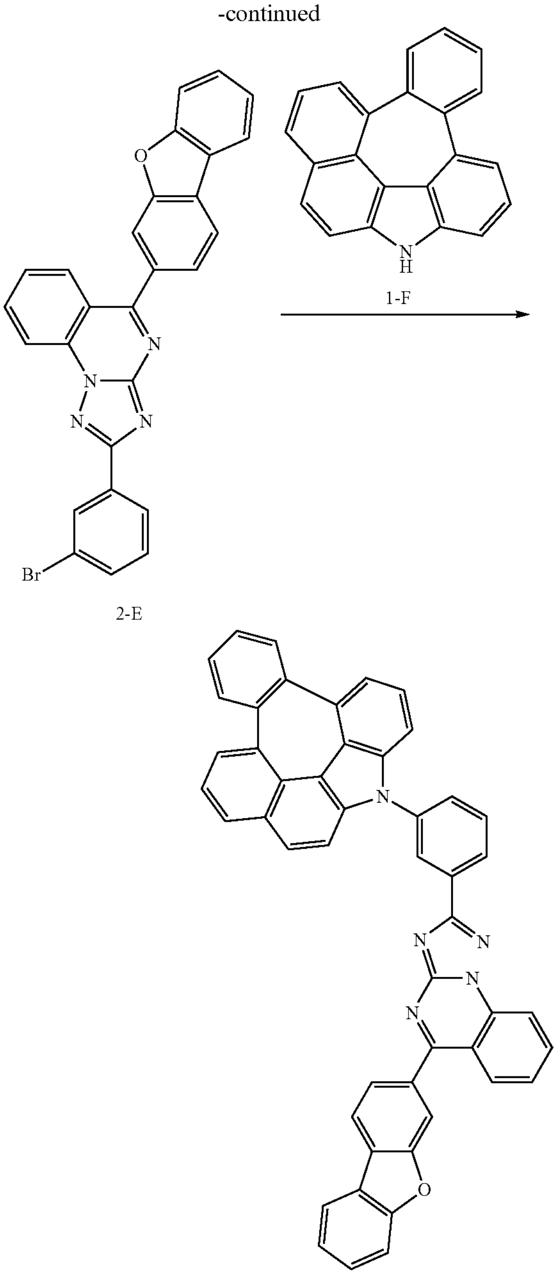

2-E

1-F

2

(1) Synthesis of 2-B: Similar to the synthesis of 1-B, with the difference that 2-A is used to replace 1-A, to obtain 2-B.

(2) Synthesis of 2-C: Similar to the synthesis of 1-C, with the difference that 2-B is used to replace 1-B, and 3-bromobenzaldehyde is used to replace 2-bromobenzaldehyde, to obtain 2-C (0.32 g, 65% yield).

(3) Synthesis of 2-D: Similar to the synthesis of 1-D, with the difference that 2-C is used to replace 1-C, to obtain 2-D (0.49 g, 62% yield).

(4) Synthesis of 2-E: Similar to the synthesis of 1-E, with the difference that 2-D is used to replace 1-D, to obtain 2-E (0.38 g, 78% yield).

(5) Synthesis of Compound 2: Similar to the synthesis of Compound 1, with the difference that 2-E is used to replace 1-E, to obtain Compound 2 (0.59 g, 84% yield).

HRMS-ESI m/z [M+H]+: 702.14.

Anal. Calcd. for $C_{49}H_{27}N_5O$: C, 83.86; H, 3.88; N, 9.98. Found: C, 83.82; H, 3.89; N, 10.01.

Synthesis Example 3

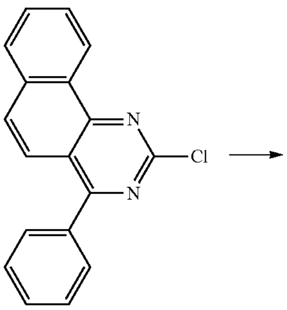

3-A

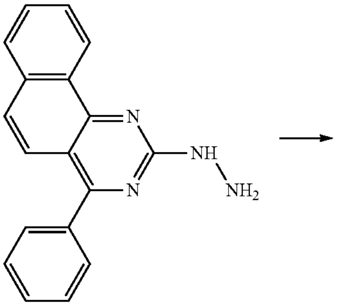

3-B

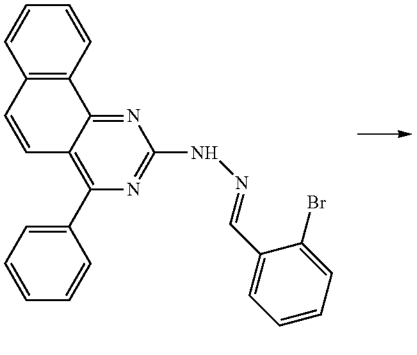

3-C

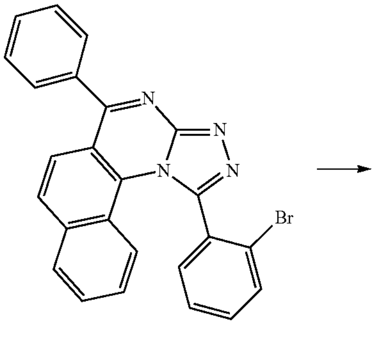

3-D

-continued

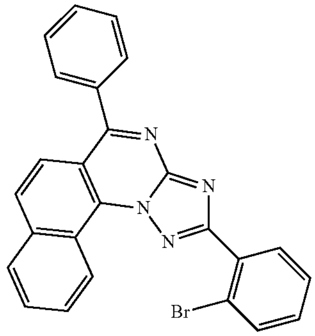

3-E

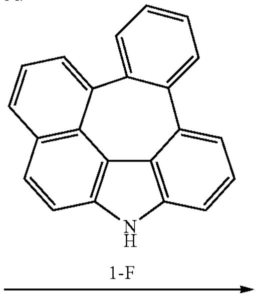

1-F

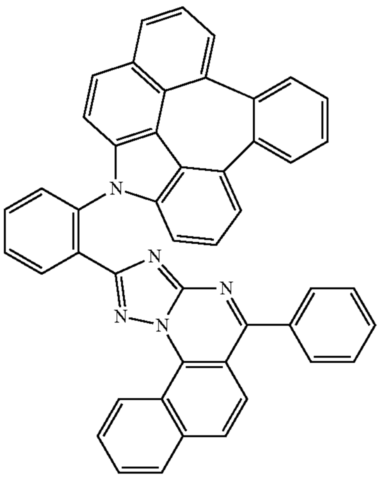

3

(1) Synthesis of 3-B: Similar to the synthesis of 1-B, with the difference that 3-A is used to replace 1-A, to obtain 3-B.

(2) Synthesis of 3-C: Similar to the synthesis of 1-C, with the difference that 3-B is used to replace 1-B, to obtain 3-C (0.30 g, 67% yield).

(3) Synthesis of 3-D: Similar to the synthesis of 1-D, with the difference that 3-C is used to replace 1-C, to obtain 3-D (0.29 g, 64% yield).

(4) Synthesis of 3-E: Similar to the synthesis of 1-E, with the difference that 3-D is used to replace 1-D, to obtain 3-E (0.37 g, 82% yield).

(5) Synthesis of Compound 3: Similar to the synthesis of Compound 1, with the difference that 3-E is used to replace 1-E, to obtain Compound 3 (0.51 g, 77% yield).

HRMS-ESI m/z [M+H]+: 662.17.

Anal. Calcd. for $C_{47}H_{27}N_5$: C, 85.30; H, 4.11; N, 10.58. Found: C, 85.31; H, 4.09; N, 10.60.

Synthesis Example 4

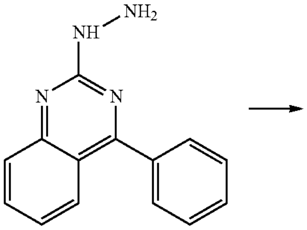

1-B

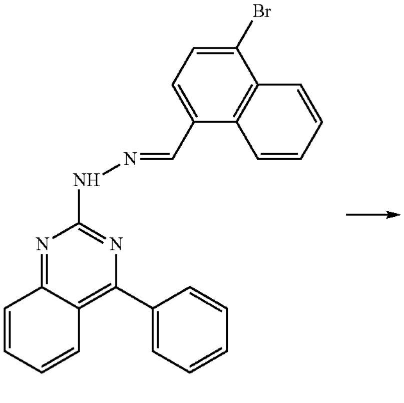

4-C

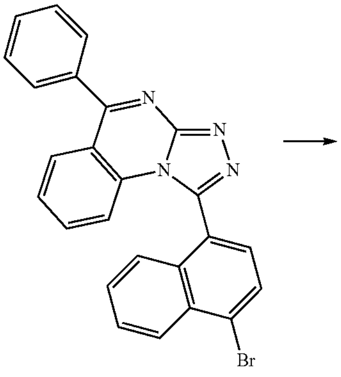

4-D

-continued

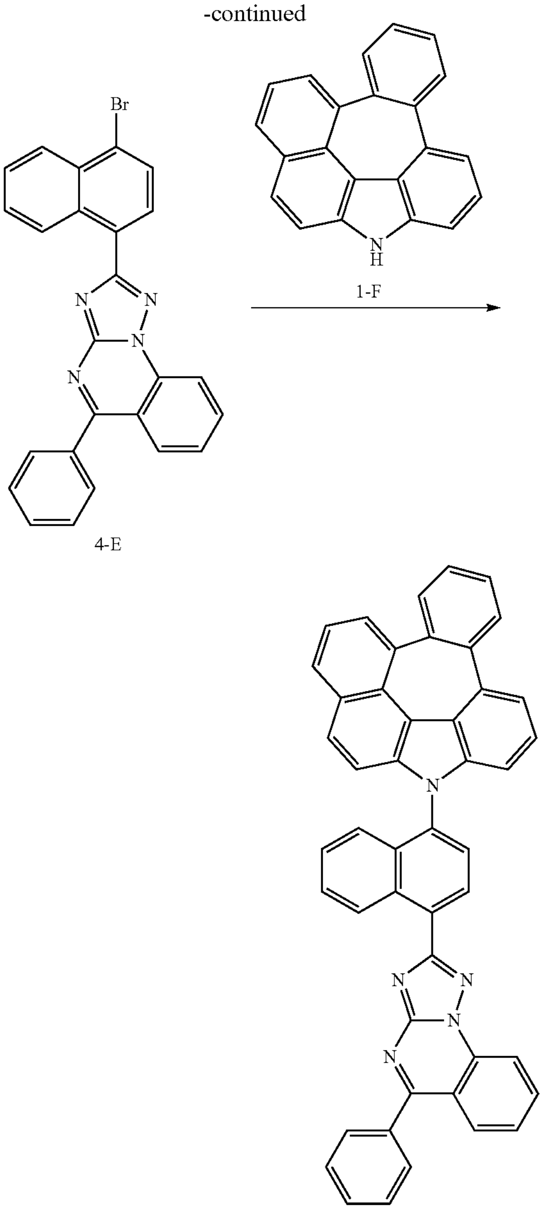

4-E

1-F

4

(1) Synthesis of 4-C: Similar to the synthesis of 1-C, with the difference that 1-bromo-4-phthaldehyde is used to replace 2-bromobenzaldehyde, to obtain 4-C (0.3 g, 67% yield).

(2) Synthesis of 4-D: Similar to the synthesis of 1-D, with the difference that 4-C is used to replace 1-C, to obtain 4-D (0.45 g, 62% yield).

(3) Synthesis of 4-E: Similar to the synthesis of 1-E, with the difference that 4-D is used to replace 1-D, to obtain 4-E (0.36 g, 80% yield).

(4) Synthesis of Compound 4: Similar to the synthesis of Compound 1, with the difference that 4-E is used to replace 1-E, to obtain Compound 4 (0.56 g, 85% yield).

HRMS-ESI m/z [M+H]+: 662.25.

Anal. Calcd. for $C_{47}H_{27}N_5$: C, 85.30; H, 4.11; N, 10.58. Found: C, 85.30; H, 4.09; N, 10.61.

Synthesis Example 5

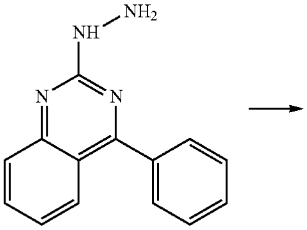

1-B

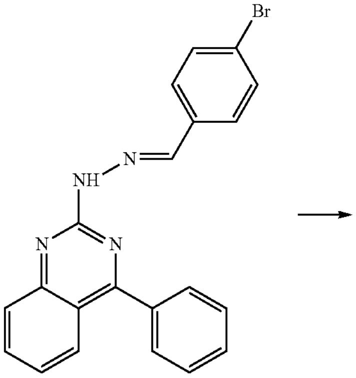

5-C

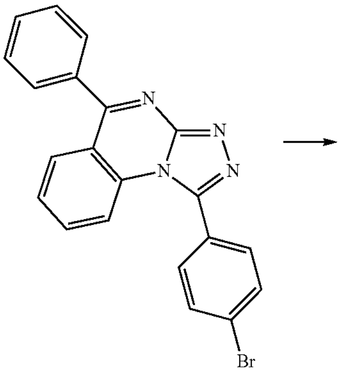

5-D

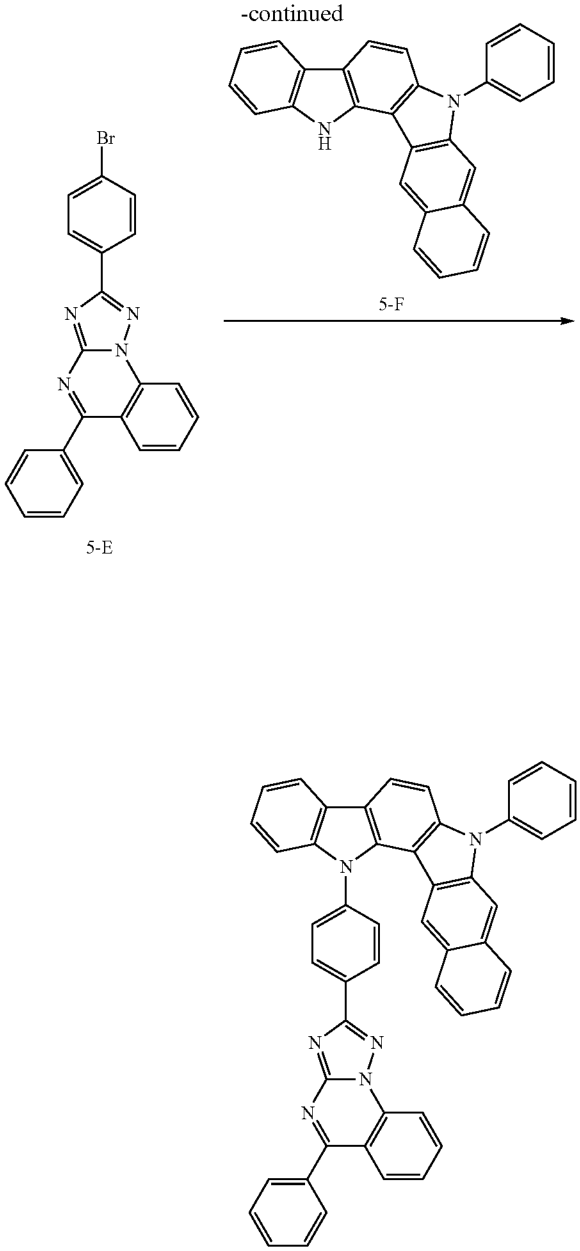

5-F

5-E

5

(1) Synthesis of 5-C: Similar to the synthesis of 1-C, with the difference that 4-bromobenzaldehyde is used to replace 2-bromobenzaldehyde, to obtain 5-C (0.28 g, 70% yield).

(2) Synthesis of 5-D: Similar to the synthesis of 1-D, with the difference that 5-C is used to replace 1-C, to obtain 5-D (0.26 g, 65% yield).

(3) Synthesis of 5-E: Similar to the synthesis of 1-E, with the difference that 5-D is used to replace 1-D, to obtain 5-E (0.32 g, 80% yield).

(4) Synthesis of Compound 5: Similar to the synthesis of Compound 1, with the difference that 5-E is used to replace 1-E, and 5-F is used to replace 1-F, to obtain Compound 5 (0.58 g, 83% yield).

HRMS-ESI m/z [M+H]+: 703.18.

Anal. Calcd. for $C_{49}H_{30}N_6$: C, 83.74; H, 4.30; N, 11.96. Found: C, 83.69; H, 4.31; N, 12.00.

Synthesis Example 6

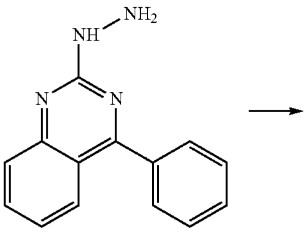

1-B

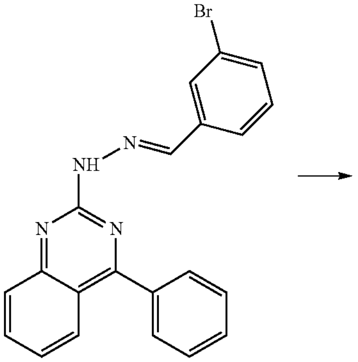

6-C

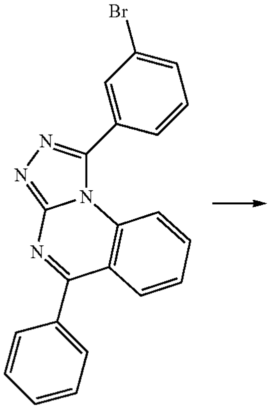

6-D

-continued

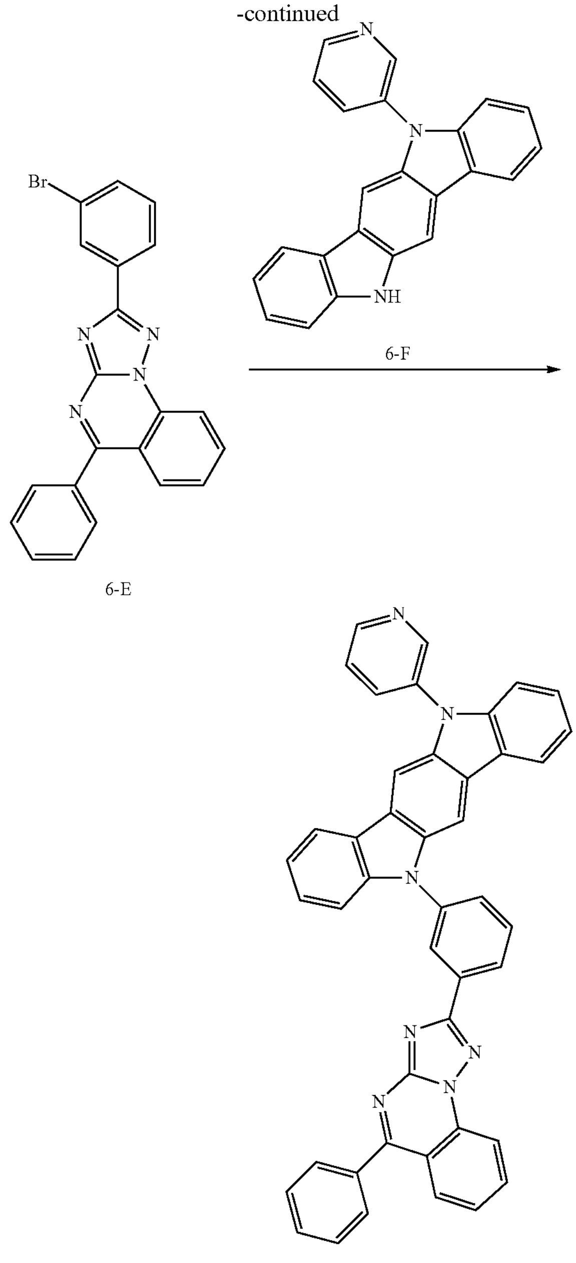

6

(1) Synthesis of 6-C: Similar to the synthesis of 1-C, with the difference that 3-bromobenzaldehyde is used to replace 2-bromobenzaldehyde, to obtain 6-C (0.26 g, 65% yield).

(2) Synthesis of 6-D: Similar to the synthesis of 1-D, with the difference that 6-C is used to replace 1-C, to obtain 6-D (0.24 g, 60% yield).

(3) Synthesis of 6-E: Similar to the synthesis of 1-E, with the difference that 6-D is used to replace 1-D, to obtain 6-E (0.31 g, 77% yield).

(4) Synthesis of Compound 6: Similar to the synthesis of Compound 1, with the difference that 6-E is used to replace 1-E, and 6-F is used to replace 1-F, to obtain Compound 6 (0.54 g, 83% yield).

HRMS-ESI m/z [M+H]+: 654.22.

Anal. Calcd. for $C_{44}H_{27}N_7$: C, 80.84; H, 4.16; N, 15.00. Found: C, 80.78; H, 4.17; N, 15.05.

Synthesis Example 7

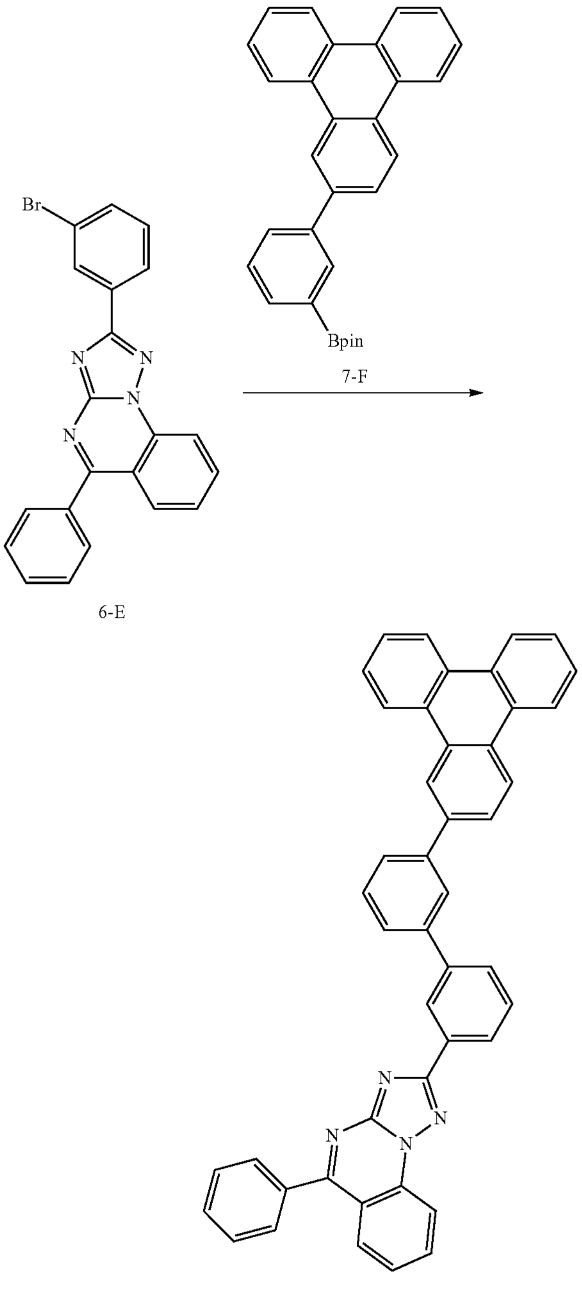

7

Synthesis of Compound 7: In a three-necked bottle of 50 mL, 6-E (1 mmol), a raw material 7-F (1 mmol), potassium carbonate (1.2 mmol), tetrakis(triphenylphosphine)palladium (0.05 mmol), toluene (10 mL) and water (3 mL) were added, to react at 60° C. for 10 h. After the reaction ended, the reaction mixture was cooled to room temperature, quenched by adding 3 mL ice-cold water, extracted by methylene dichloride (10×3 mL), and the extracted solution was dried by magnesium sulfate, filtered, and dried by rotary evaporation to give a crude product, and the crude product was purified by column chromatography (ethyl acetate/n-hexane, 1/10 (volume ratio)), to obtain Compound 7 (0.44 g, 71% yield).
HRMS-ESI m/z [M+H]+: 625.19.
Anal. Calcd. for $C_{45}H_{28}N_4$: C, 86.51; H, 4.52; N, 8.97. Found: C, 86.50; H, 4.50; N, 9.00.
Synthesis Example 8
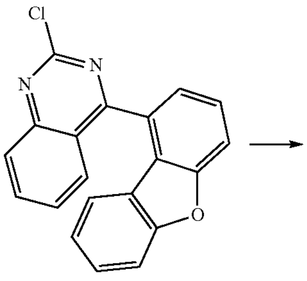
8-A
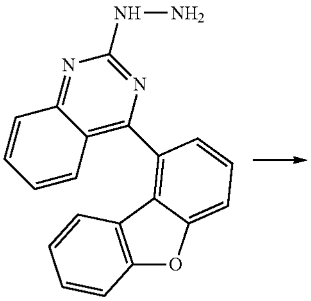
8-B
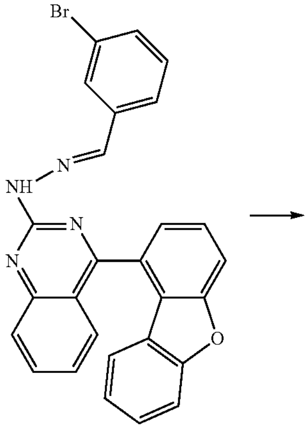
8-C
-continued
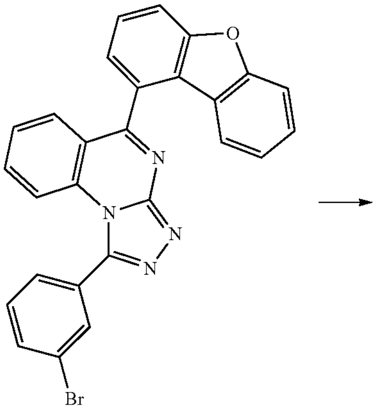
8-D
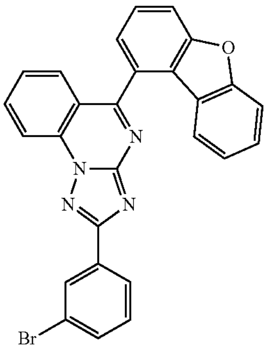
8-E
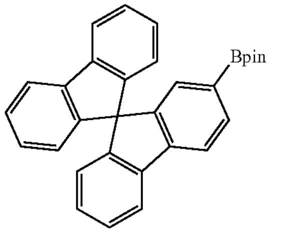
8-F
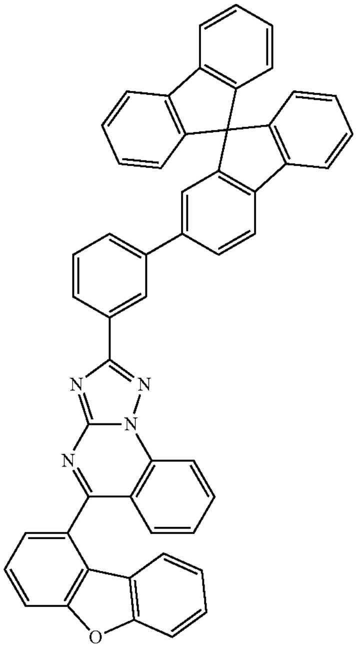
8
(1) Synthesis of 8-B: Similar to the synthesis of 1-B, with the difference that 8-A is used to replace 1-A, to obtain 8-B.

(2) Synthesis of 8-C: Similar to the synthesis of 1-C, with the difference that 8-B is used to replace 1-B, and 3-bromobenzaldehyde is used to replace 2-bromobenzaldehyde, to obtain 8-C (0.32 g, 65% yield).

(3) Synthesis of 8-D: Similar to the synthesis of 1-D, with the difference that 8-C is used to replace 1-C, to obtain 8-D (0.3 g, 61% yield).

(4) Synthesis of 8-E: Similar to the synthesis of 1-E, with the difference that 8-D is used to replace 1-D, to obtain 8-E (0.38 g, 77% yield).

(5) Synthesis of Compound 8: Similar to the synthesis of Compound 1, with the difference that 8-E is used to replace 1-E, and 8-F is used to replace 1-F, to obtain Compound 8 (0.58 g, 80% yield).

HRMS-ESI m/z [M+H]+: 727.27.

Anal. Calcd. for $C_{52}H_{30}N_4O$: C, 85.93; H, 4.16; N, 7.71. Found: C, 85.97; H, 4.14; N, 7.69.

Synthesis Example 9

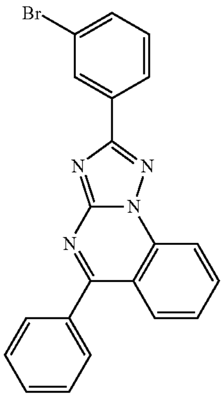

6-E

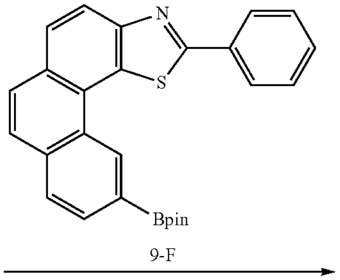

9-F

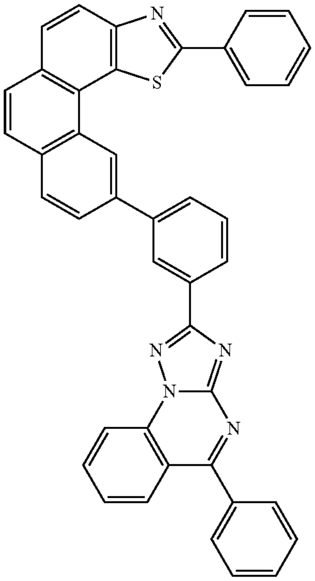

9

Synthesis of Compound 9: Similar to the synthesis of Compound 7, with the difference that 9-F is used to replace 7-F, to obtain Compound 9 (0.49 g, 78% yield).

HRMS-ESI m/z [M+H]+: 632.18.

Anal. Calcd. for $C_{45}H_{25}N_5S$: C, 79.85; H, 3.99; N, 11.09; S, 5.07. Found: C, 79.89; H, 4.00; N, 11.06; S, 5.05.

Synthesis Example 10

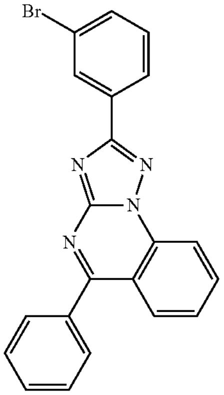

6-E

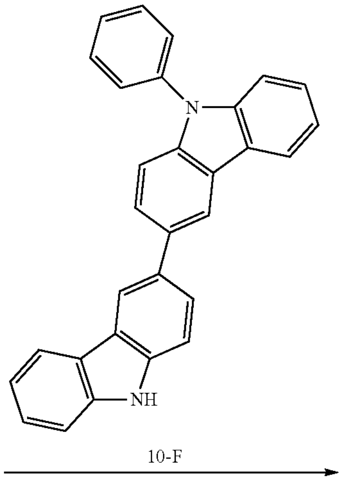

10-F

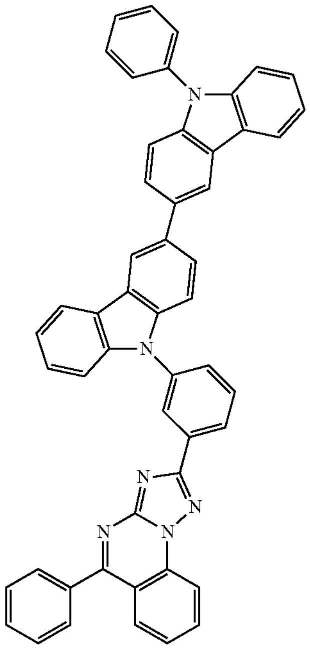

10

Synthesis of Compound 10: Similar to the synthesis of Compound 1, with the difference that 6-E is used to replace 1-E, and 10-F is used to replace 1-F, to obtain Compound 10 (0.64 g, 88% yield).
HRMS-ESI m/z [M+H]+: 729.28.
Anal. Calcd. for $C_{51}H_{32}N_6$: C, 84.04; H, 4.43; N, 11.53. Found: C, 84.00; H, 4.44; N, 11.56.
Synthesis Example 11
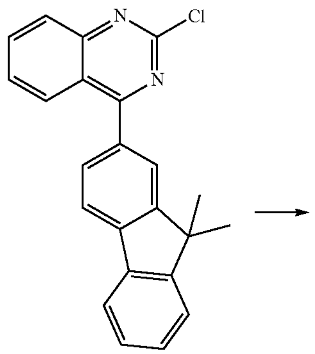
11-A
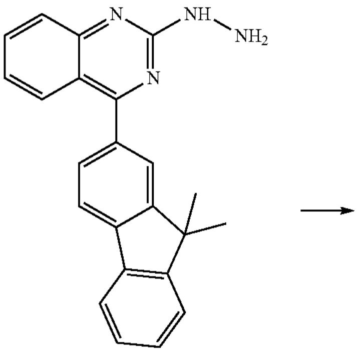
11-B
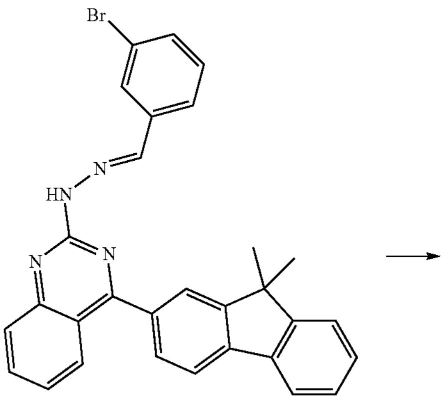
11-C
-continued
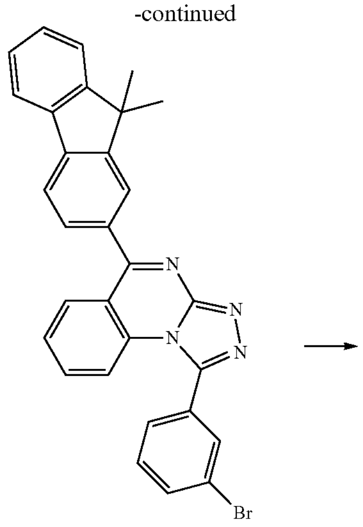
11-D
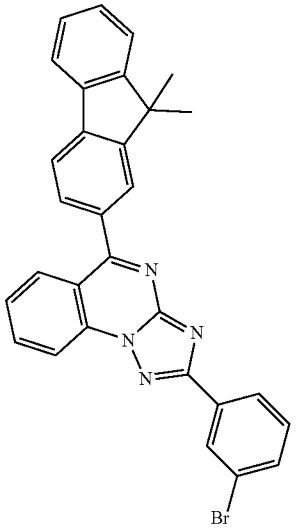
11-E
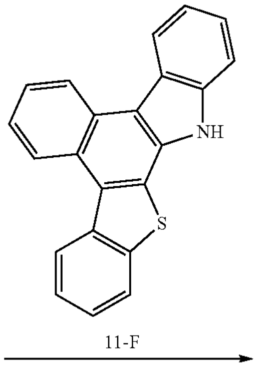
11-F -continued

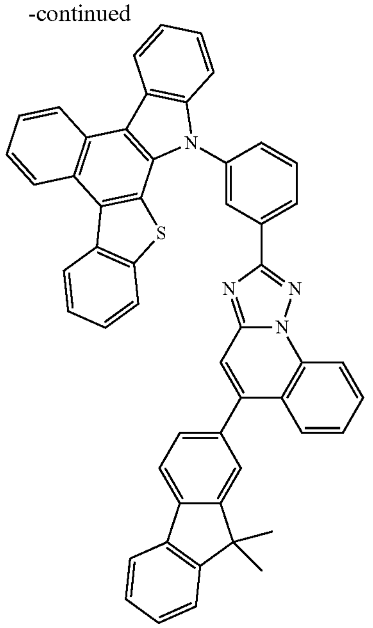

11

(1) Synthesis of 11-B: Similar to the synthesis of 1-B, with the difference that 11-A is used to replace 1-A, to obtain 11-B.

(2) Synthesis of 11-C: Similar to the synthesis of 1-C, with the difference that 11-B is used to replace 1-B, and 3-bromobenzaldehyde is used to replace 2-bromobenzaldehyde, to obtain 11-C (0.36 g, 69% yield).

(3) Synthesis of 11-D: Similar to the synthesis of 1-D, with the difference that 11-C is used to replace 1-C, to obtain 11-D (0.33 g, 64% yield).

(4) Synthesis of 11-E: Similar to the synthesis of 1-E, with the difference that 11-D is used to replace 1-D, to obtain 11-E (0.41 g, 79% yield).

(5) Synthesis of Compound 11: 11-E is used to replace 1-E, and 11-F is used to replace 1-F, to obtain Compound 11 (0.64 g, 84% yield).

HRMS-ESI m/z [M+H]+: 760.28.

Anal. Calcd. for $C_{52}H_{33}N_5S$: C, 82.19; H, 4.38; N, 9.22; S, 4.22. Found: C, 82.16; H, 4.39; N, 9.25; S, 4.20.

Element Example 1

An organic electroluminescence element comprising an anode (ITO), a hole injection layer, a hole transport layer, an emitting layer, an electron transport layer, an electron injection layer and a cathode, which were sequentially layered on a substrate, was prepared by the following method:

(1) Cleaning the substrate: a glass substrate coated with ITO (the anode) was ultrasonicated in an aqueous detergent, washed in deionized water, degreased in an acetone/ethanol mixed solvent (volume ratio=1:1) by ultrasonication, baked in a clear environment until water was completely removed, and washed by ozone under ultraviolet light;

(2) Depositing the hole injection layer: the glass substrate with an anode layer was placed in a chamber, and the chamber was vacuumized until $1\times10^{-6}$ Pascal (Pa) to $2\times10^{-4}$ Pa, and NDP-9 was deposited on the anode layer in vacuum to form a first hole injection layer, in which the deposited thickness was 5 nanometers (nm); and H was deposited on the hole injection layer to form a second hole injection layer of 10 nm;

in which the hole injection layer herein comprises the first hole injection layer and the second hole injection layer;

(3) Depositing the hole transport layer: HT was deposited on the hole injection layer to form a hole transport layer, and the deposited thickness was nm;

(4) Depositing the emitting layer: the Compound 1 of the present invention (host material) and a guest material $(piq)_2Ir(acac)$ were co-deposited on the hole transport layer in vacuum, in which the mass ratio of the host material and the guest material was 95:5, and the total deposited thickness was 30 nm;

(5) Depositing the electron transport layer: ET1 and LiQ (with a mass ratio of 1:1) were co-deposited on the emitting layer in vacuum, in which the total deposited thickness was 30 nm;

(6) Depositing the electron injection layer: LiQ was deposited on the electron transport layer in vacuum to form an electron injection layer, in which the total deposited thickness was 1 nm;

(7) Depositing the cathode: Mg:Ag (with a mass ratio of 9:1) were deposited on the electron injection layer to form a cathode, in which the deposited thickness was 20 nm; to obtain the organic electroluminescence element.

Element Examples 2 to 11, Comparative Element Example 1

An organic electroluminescence element was prepared, with the difference from the Element Example 1 that, the host material in the emitting layer was replaced with the corresponding compounds for Element Examples 2 to 11 and Comparative Element Example 1 listed in Table 1. The Compounds 1 to 11 are described above, and the Comparative Compound is shown below.

The structures of the materials involved in the above Element Examples and Comparative Element Example are shown as below:

NDP-9

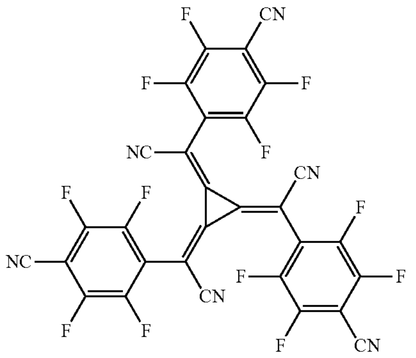

-continued

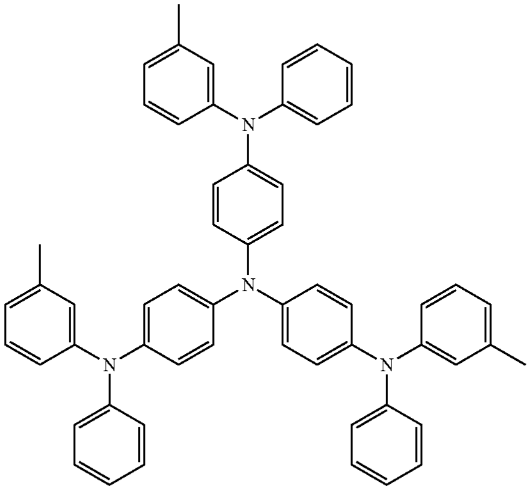

H

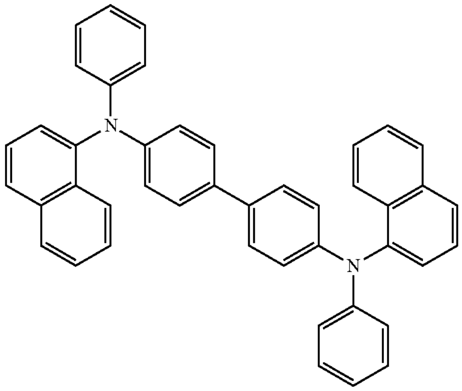

HT

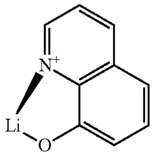

LiQ

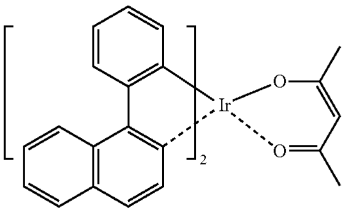

(piq)$_2$Ir(acac)

-continued

ET1

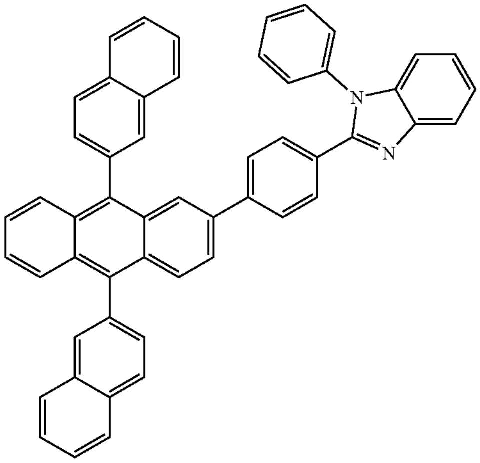

Comparative Compound

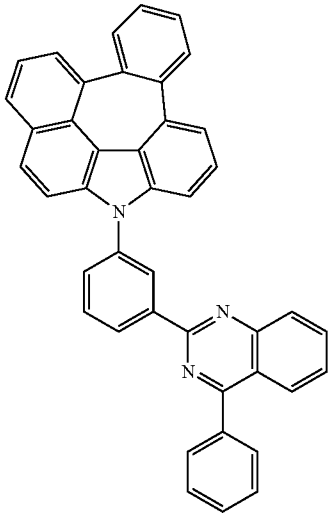

Characteristic Tests:

The characteristics such as current, voltage, luminance and the like of the organic electroluminescence elements of the above Element Examples 1 to 11 and Comparative Element Example 1 were synchronously tested by PR 650 SpectraScan Colorimeter and Keithley K 2400 SourceMeter;

Testing conditions: with a current density of 10 milliamperes/square centimeter (mA/cm$^2$) under room temperature;

Service life test: tested with a current density of 20 mA/cm$^2$ under room temperature, and the time period recorded when the luminance of the tested element was reduced to 95% of the original luminance (in hour). The test results are shown in Table 1.

TABLE 1

| | Host material in the emitting layer | Driving voltage (V) | Current efficiency (Cd/A) | Service life (h) |
|---|---|---|---|---|
| Element Example 1 | Compound 1 | 3.9 | 20 | 301 |
| Element Example 2 | Compound 2 | 3.9 | 17 | 311 |
| Element Example 3 | Compound 3 | 4.0 | 18 | 305 |

TABLE 1-continued

| | Host material in the emitting layer | Driving voltage (V) | Current efficiency (Cd/A) | Service life (h) |
|---|---|---|---|---|
| Element Example 4 | Compound 4 | 4.0 | 17 | 317 |
| Element Example 5 | Compound 5 | 3.9 | 17 | 288 |
| Element Example 6 | Compound 6 | 4.0 | 16 | 292 |
| Element Example 7 | Compound 7 | 4.1 | 16 | 281 |
| Element Example 8 | Compound 8 | 4.1 | 15 | 278 |
| Element Example 9 | Compound 9 | 4.1 | 17 | 273 |
| Element Example 10 | Compound 10 | 4.0 | 19 | 298 |
| Element Example 11 | Compound 11 | 4.0 | 18 | 291 |
| Comparative Element Example 1 | Comparative Compound | 4.2 | 15 | 216 |

From Table 1, it is clear that the compounds of the present invention make the organic electroluminescence elements have a lower driving voltage (3.8 voltages (V) to 4.1 V), a higher current efficiency (15 Candelas/Ampere (Cd/A) to 23 Cd/A or higher) and a longer service life (273 h or higher).

The applicant claims herein that even though the nitrogen-containing fused heterocyclic compound of the present invention and applications thereof are demonstrated by the above examples, the scope of the present invention is not limited by these examples. That is to say, it does not mean that the present invention has to be carried out based on the above examples. Those skilled in the art should understand that any improvement of the present invention, equivalent replacement of materials, addition of auxiliary components, selection of specific means and the like are all within the scope of protection and disclosure of the present invention.

What is claimed is:

1. A nitrogen-containing fused heterocyclic compound, wherein the nitrogen-containing fused heterocyclic compound has a structure represented by Formula (1):

Formula (1)

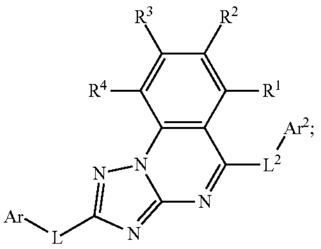

wherein,

Ar is selected from

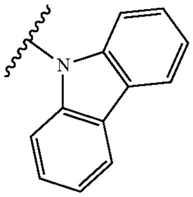

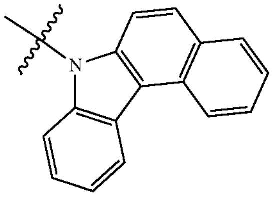

-continued

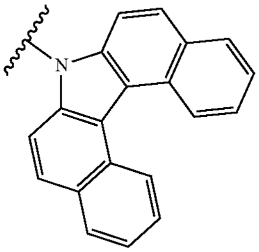

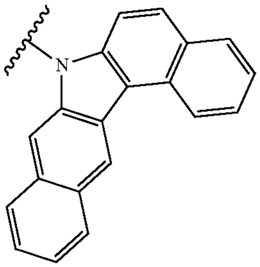

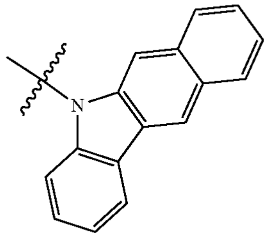

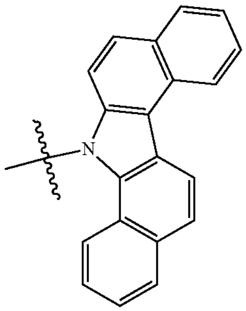

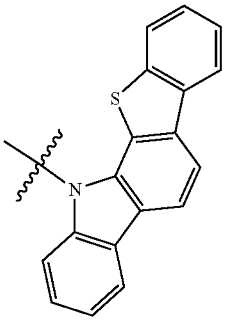

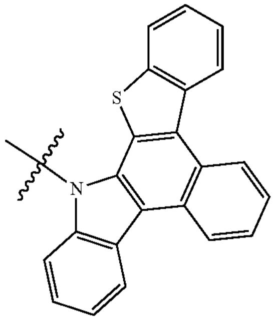

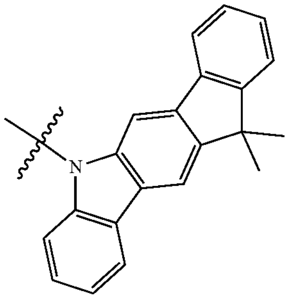

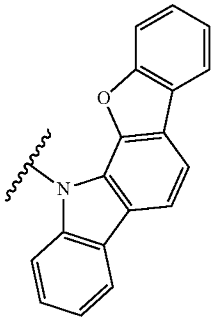

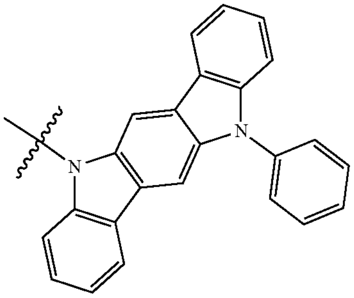

-continued
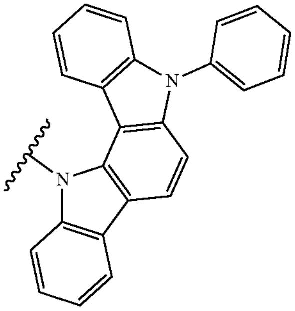
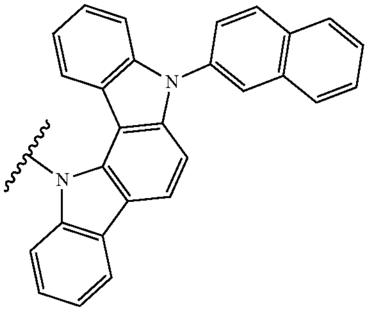
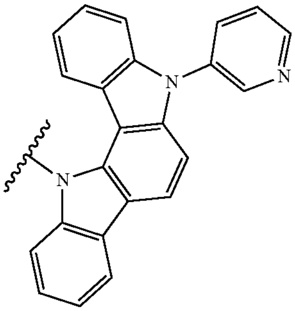
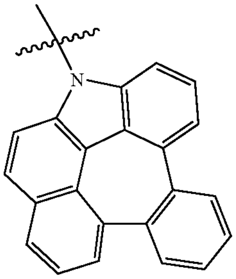
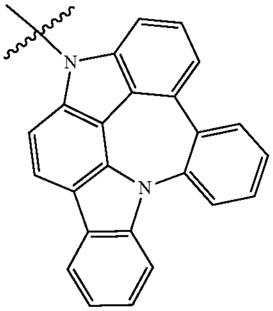
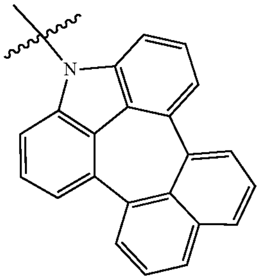
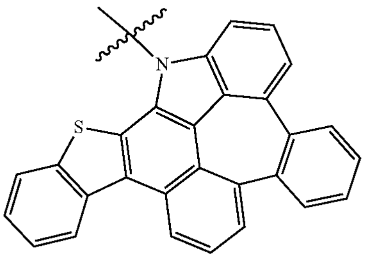
-continued
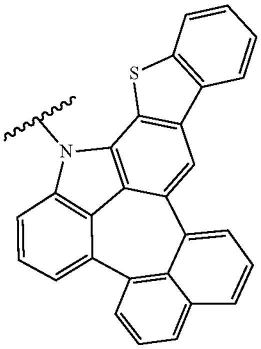
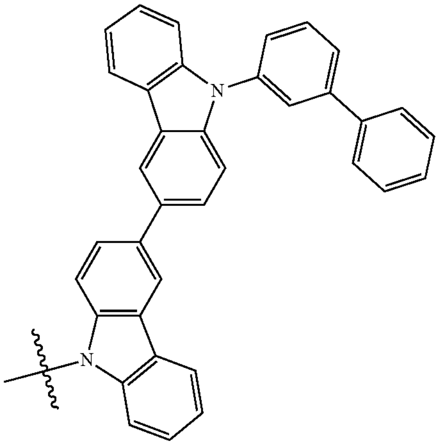
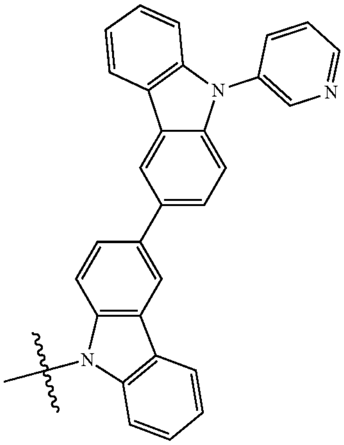
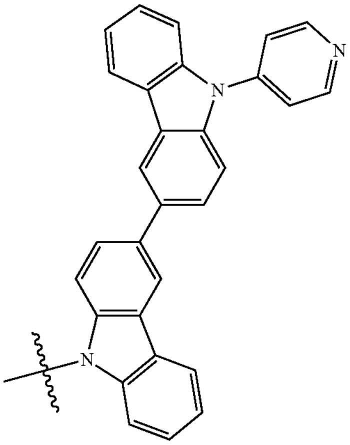

-continued
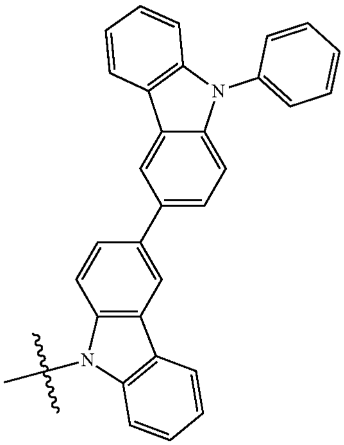
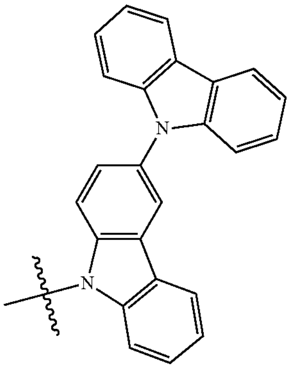
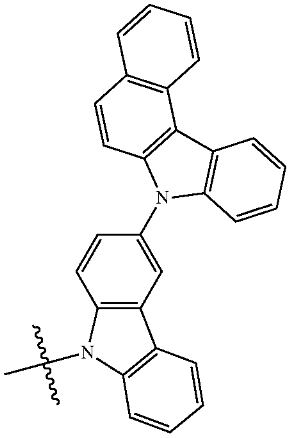
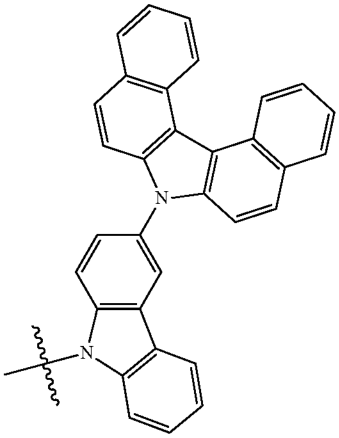
-continued
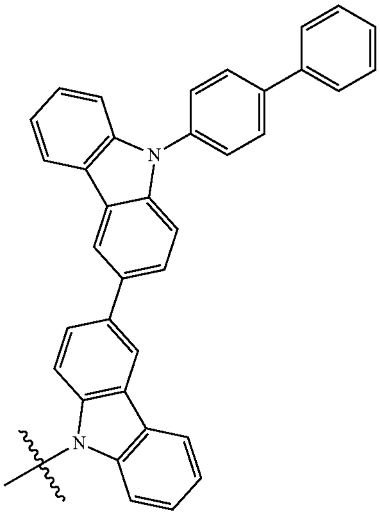
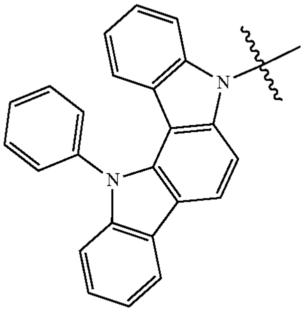
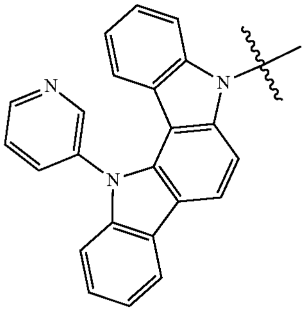
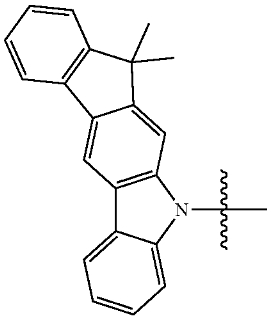
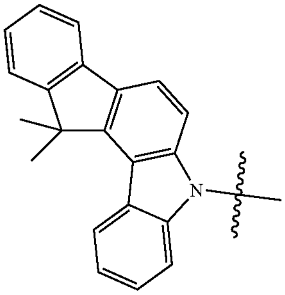

-continued
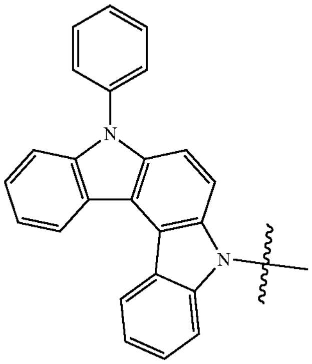
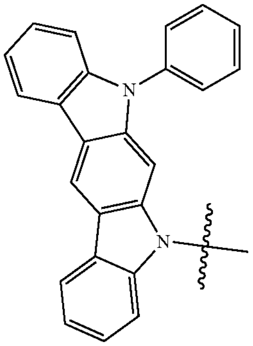
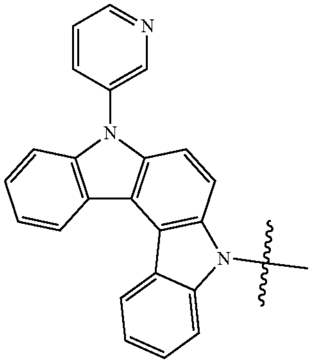
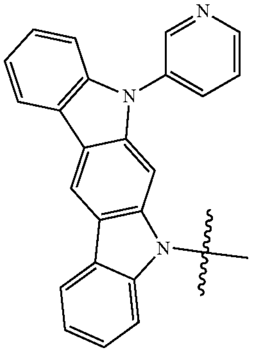
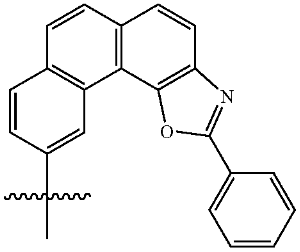
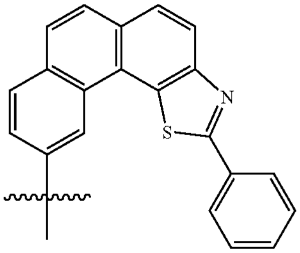
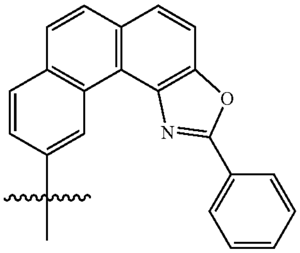
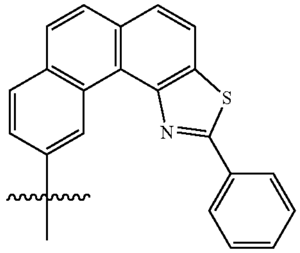
-continued
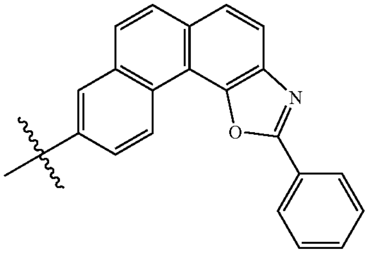
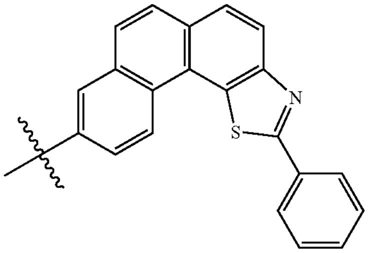
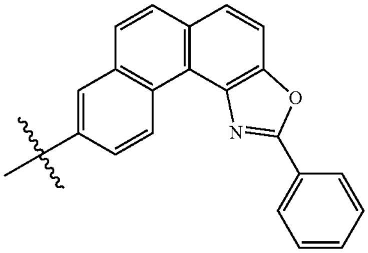
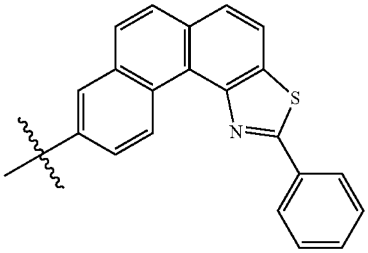
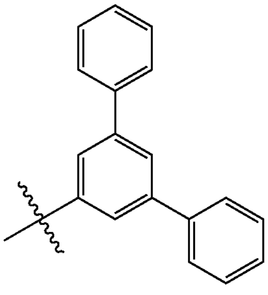
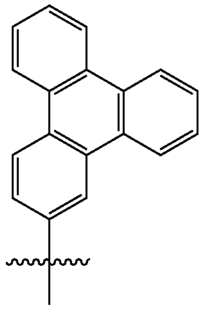
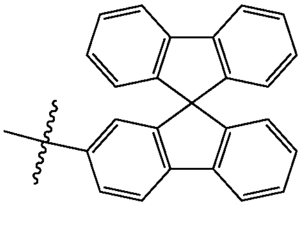
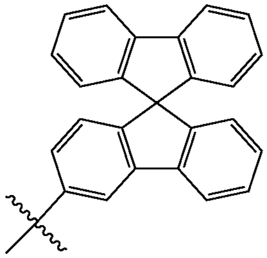

-continued
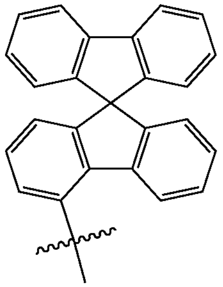
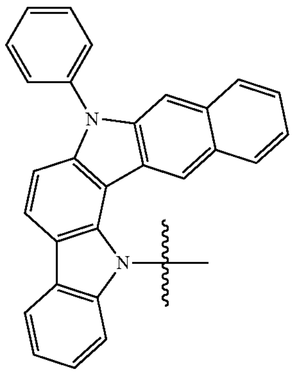
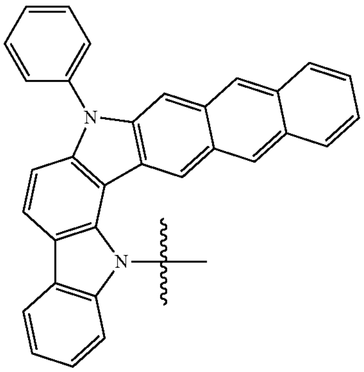
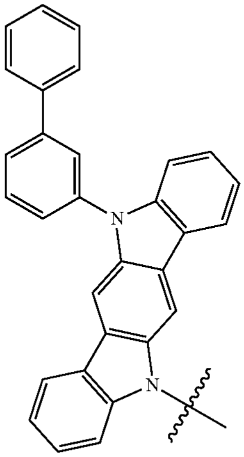
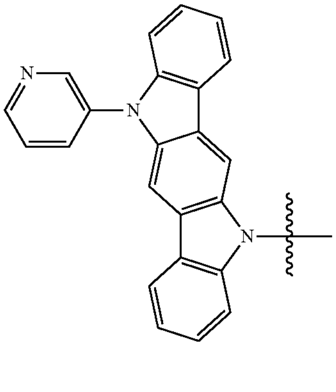
-continued
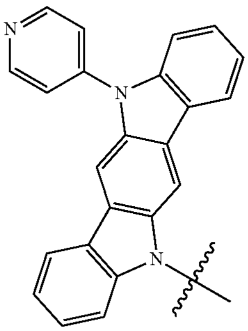
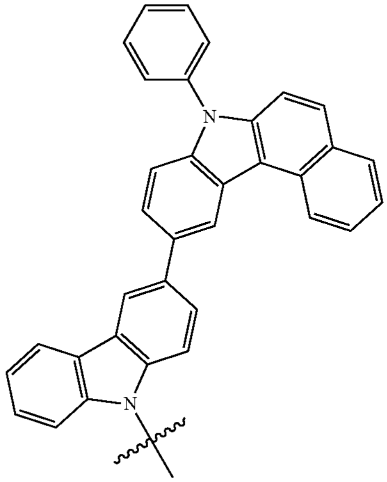
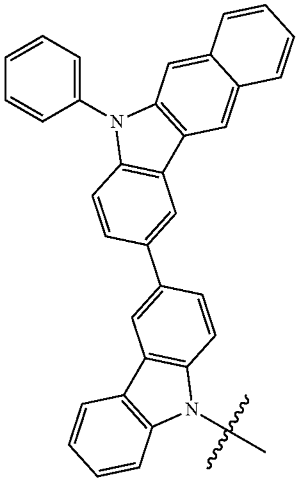
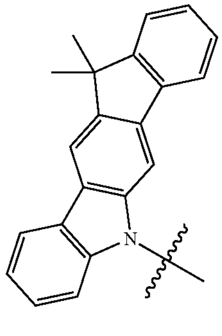
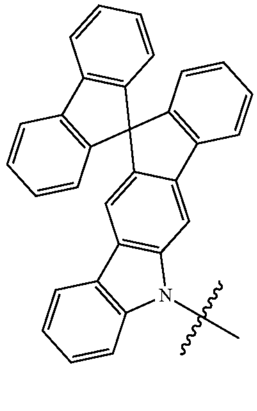
and -continued

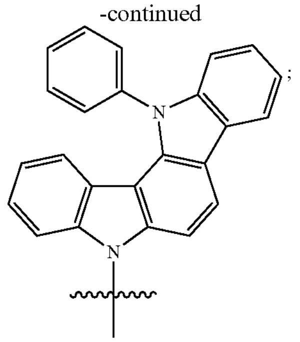

Ar$^2$ is selected from a phenyl group, a biphenylyl group, a terphenylyl group, a naphthyl group, a phenylnaphthyl group, a naphthylphenyl group, an anthryl group, a phenanthryl group, a benzophenanthryl group, a pyridyl group, a dibenzofuryl group, a dibenzothiophenyl group, a carbazolyl group, a phenylcarbazolyl group, a pyridylcarbazolyl group, a naphthylcarbazolyl group, a biphenylylcarbazolyl group, a dibenzofurylphenyl group, a dibenzothiophenylphenyl group, a dimethylfluorenyl group, a diphenylfluorenyl group, a spiro-bifluorenyl group, a benzonaphthofuryl group, a benzonaphthothiophenyl group, a benzocarbazolyl group, and a dibenzocarbazolyl group, each of which is substituted or unsubstituted;

L is selected from a phenylene group, a biphenylene group, and a naphthylene group, each of which is substituted or unsubstituted;

L$^2$ is a bond or a group selected from a phenylene group, a biphenylene group, and a naphthylene group, each of which is substituted or unsubstituted;

R$^1$ to R$^4$ are each independently hydrogen, or any adjacent two of R$^1$ to R$^4$ joined to form a ring A, and the ring A is a benzene ring.

2. The nitrogen-containing fused heterocyclic compound as claimed in claim 1, wherein the nitrogen-containing fused heterocyclic compound is any one of the following compounds:

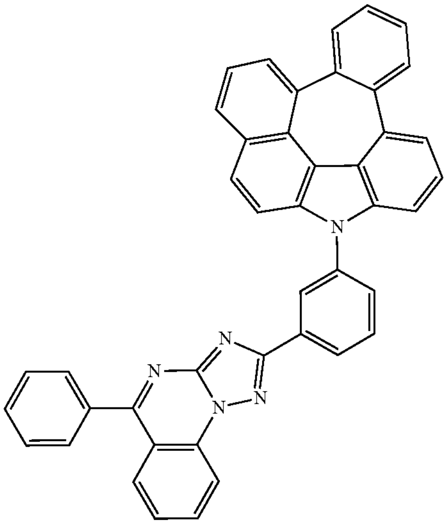

-continued

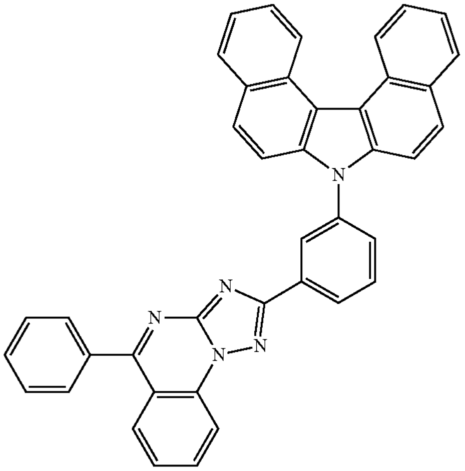

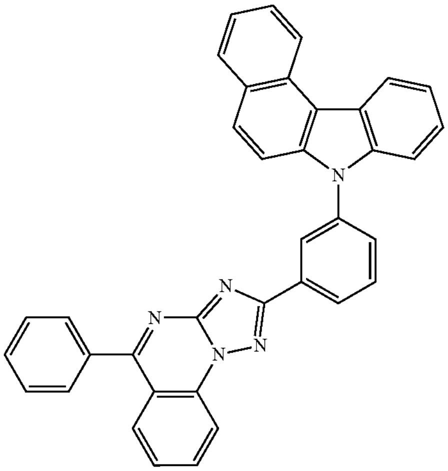

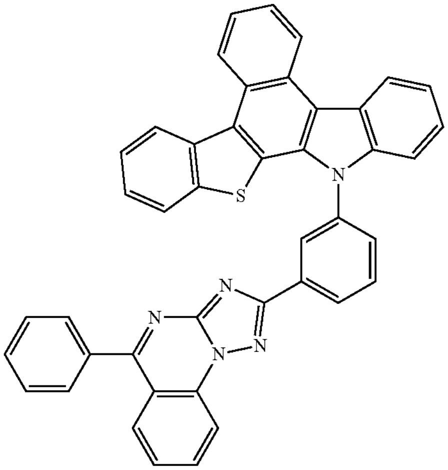

-continued
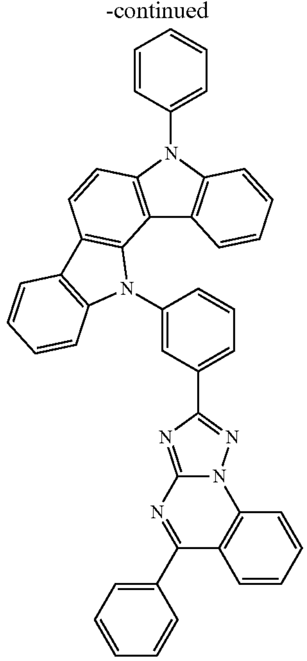
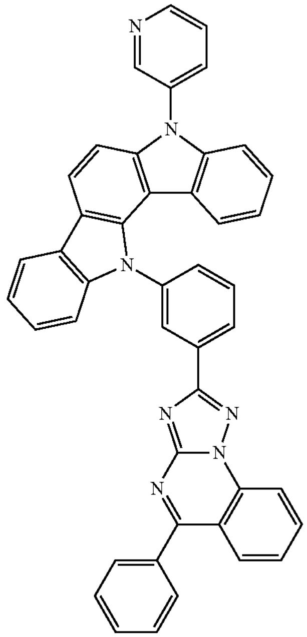
-continued
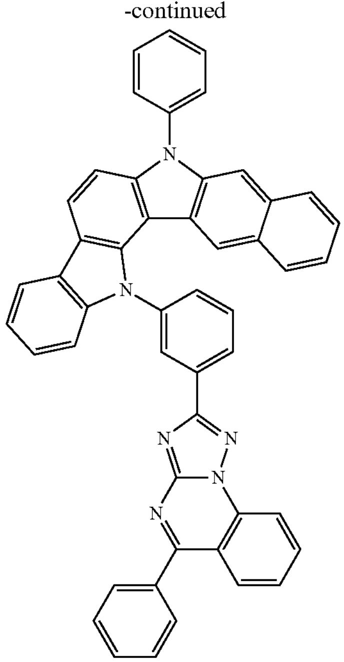
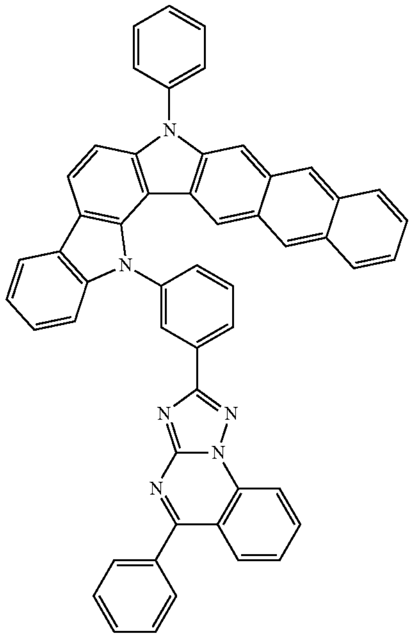

-continued
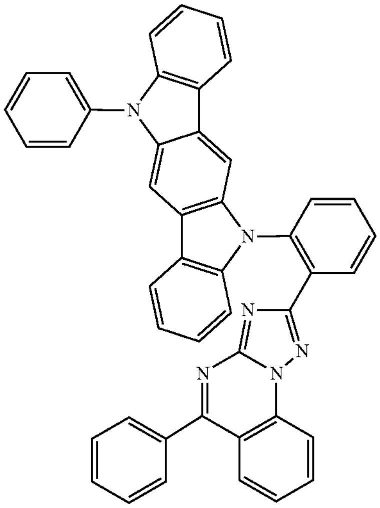
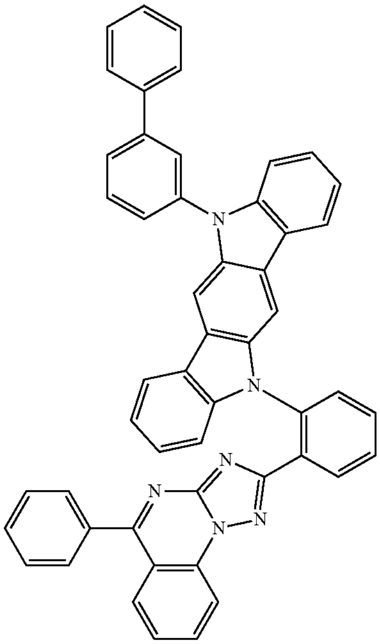
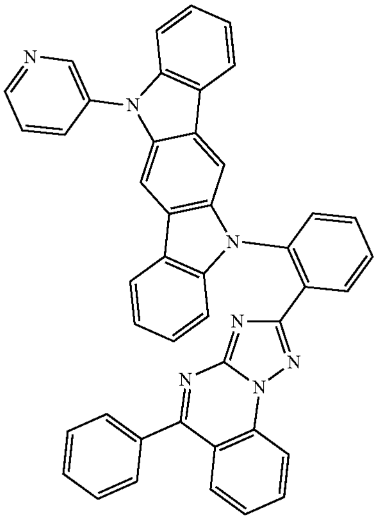
-continued
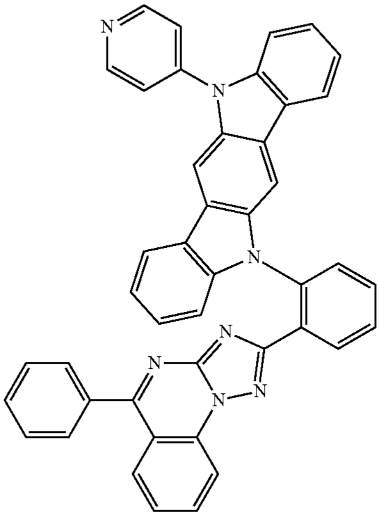
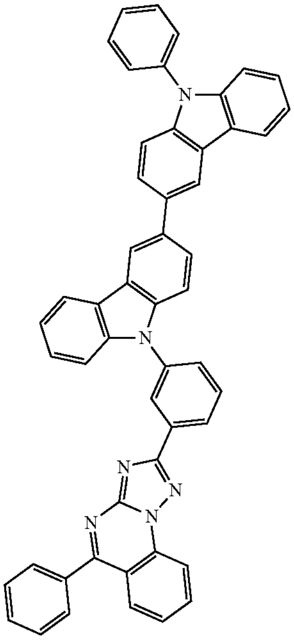
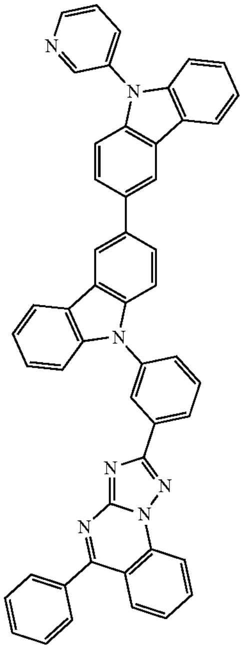

-continued
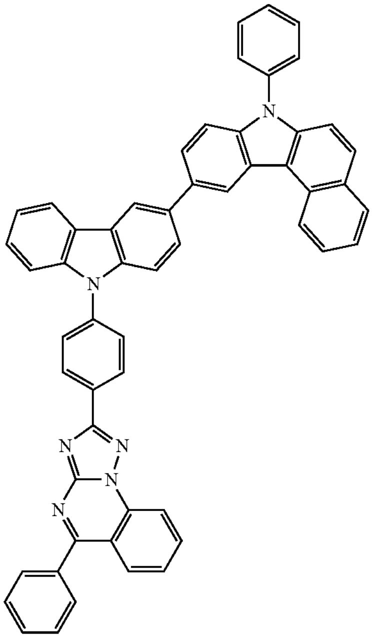
-continued
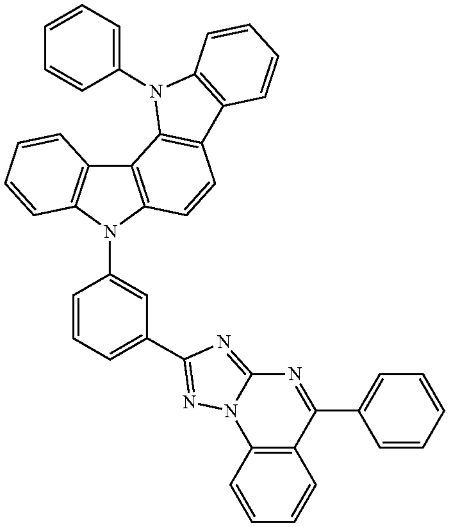
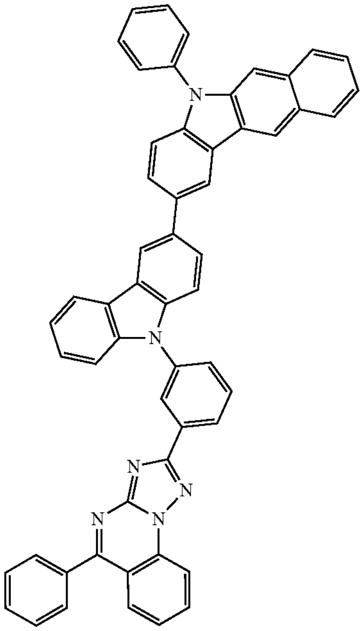
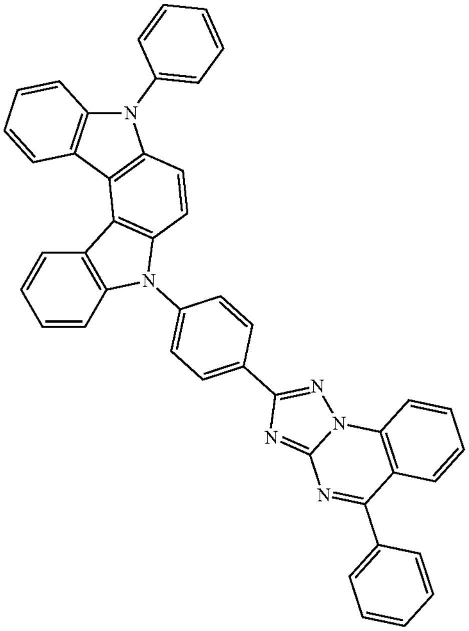

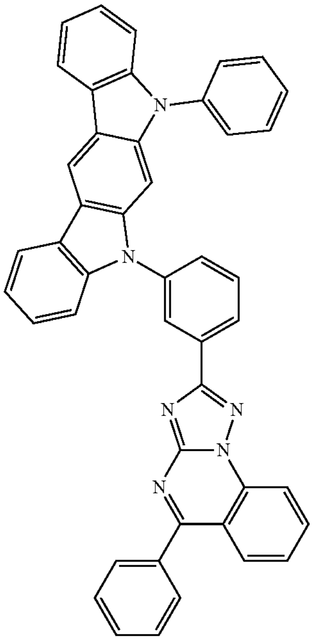
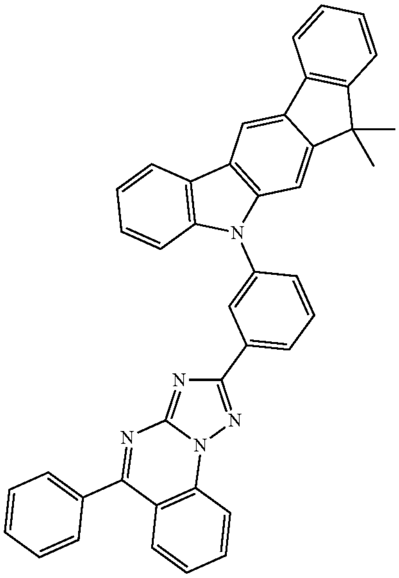
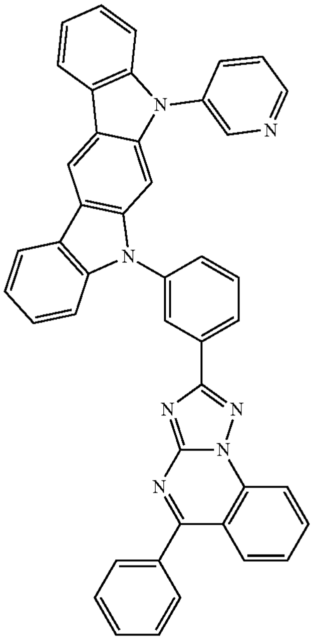
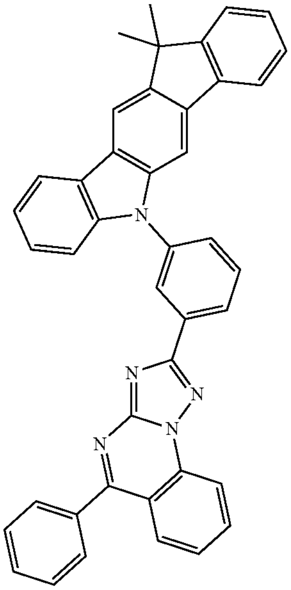

-continued
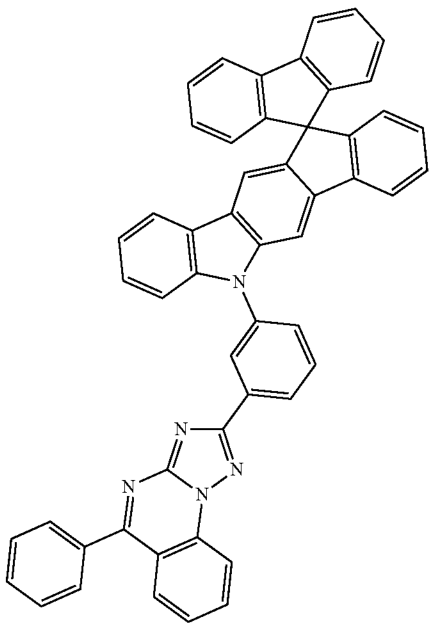
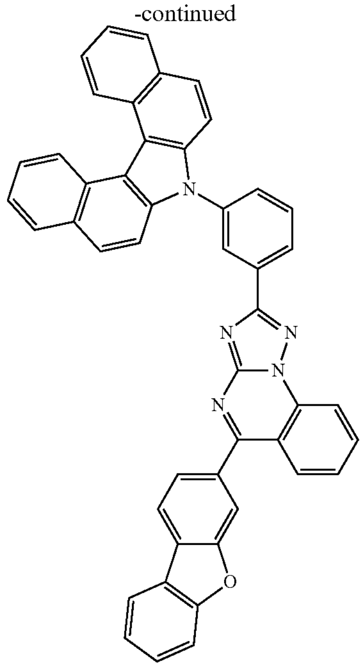
-continued
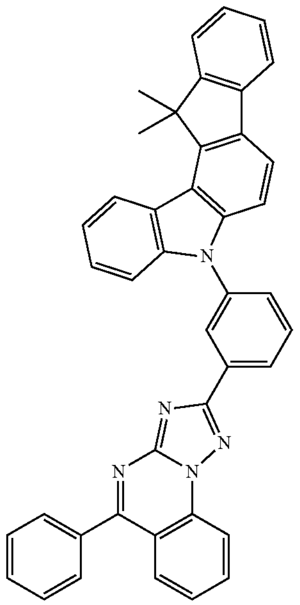
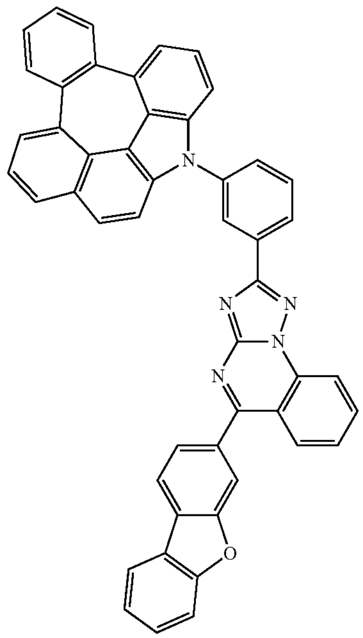

-continued
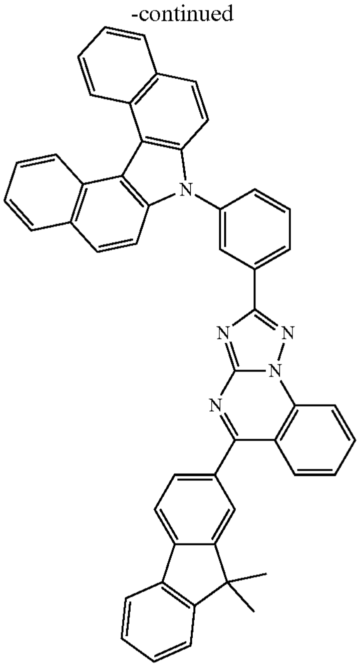
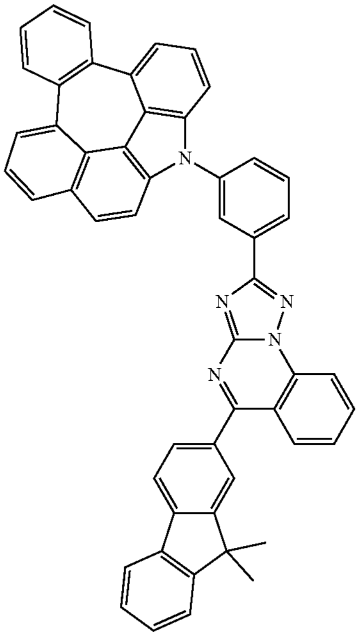
-continued
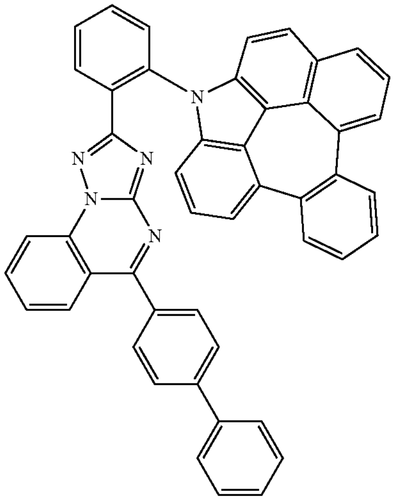
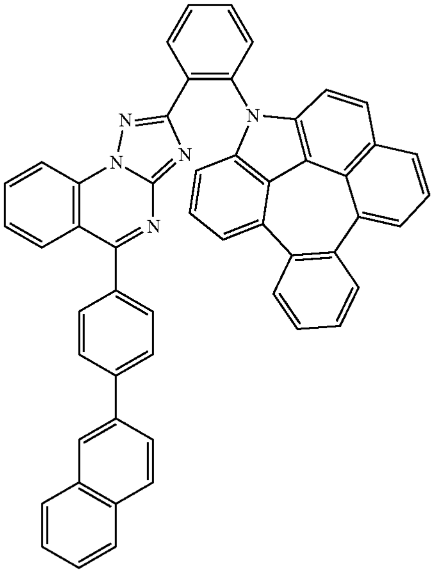
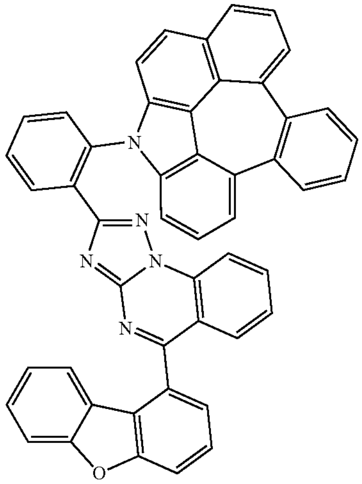

137
-continued
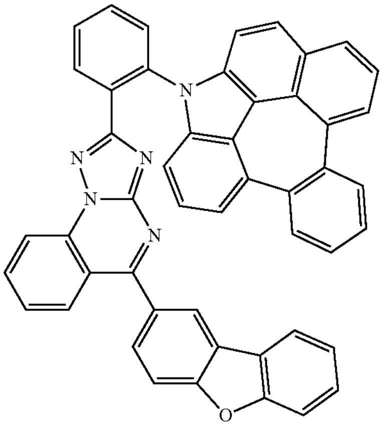
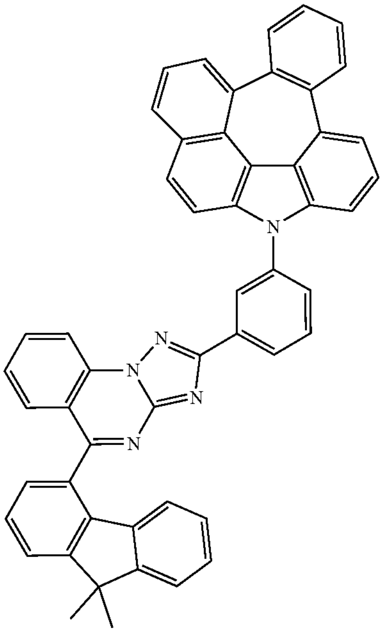
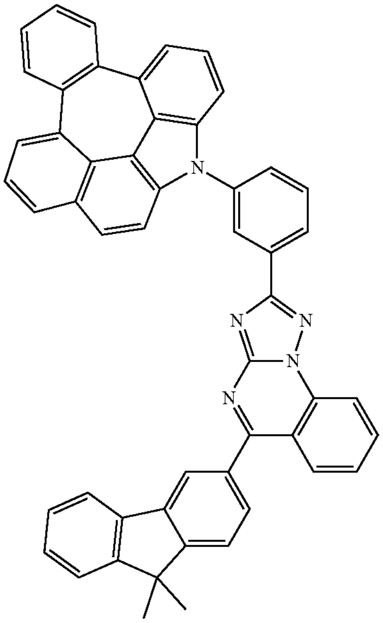
138
-continued
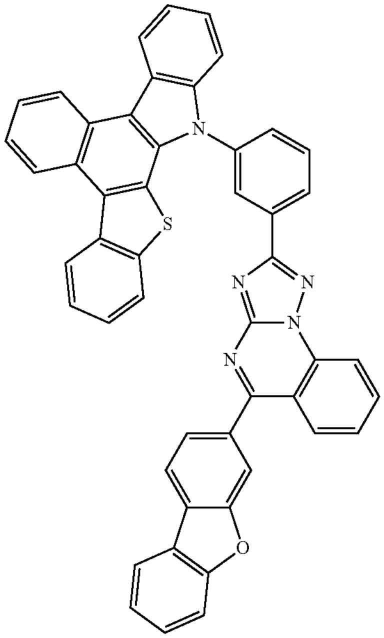
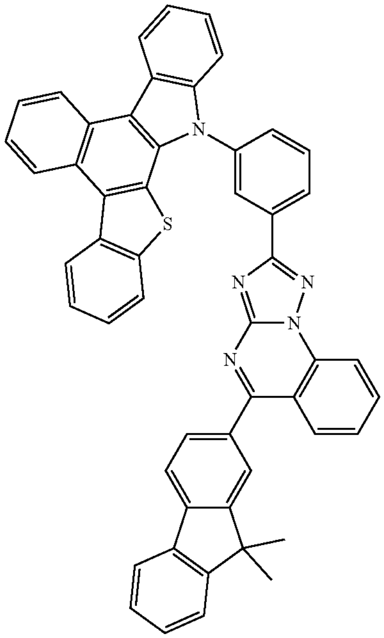

-continued
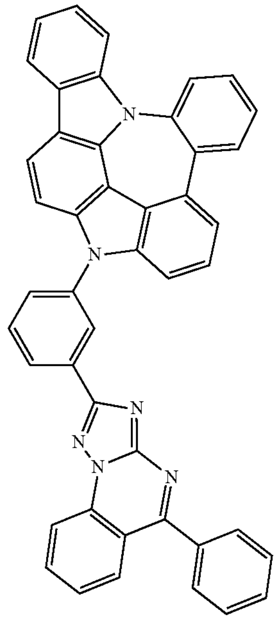
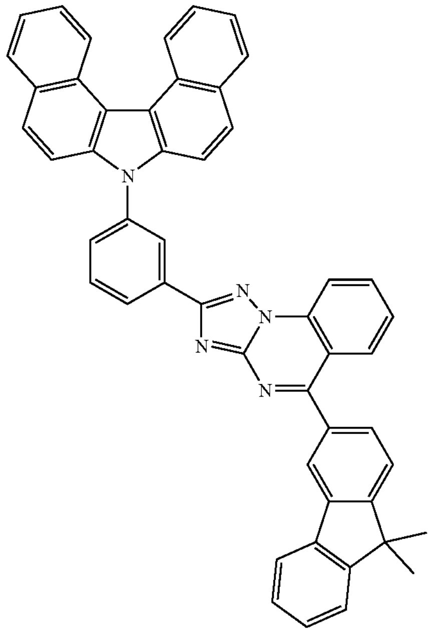
-continued
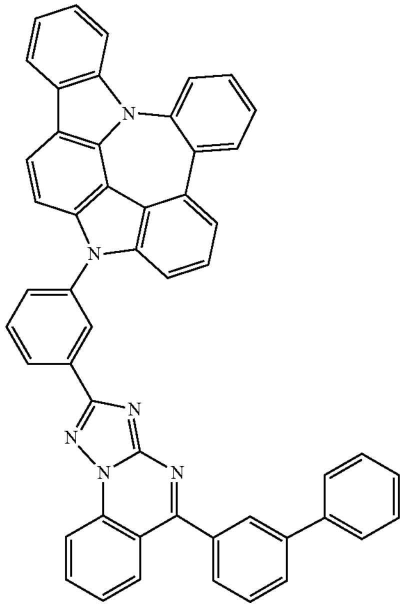
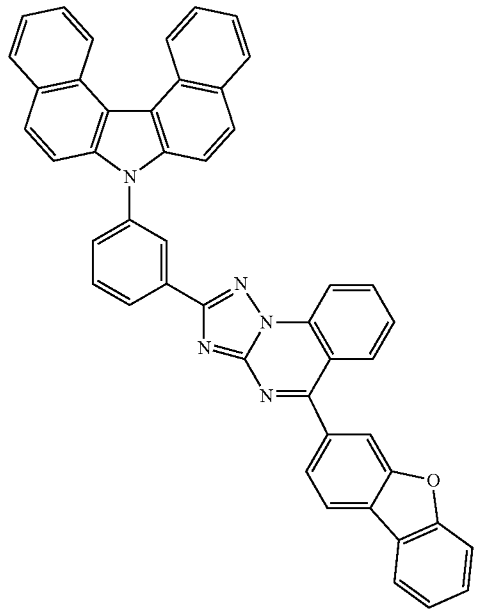

-continued
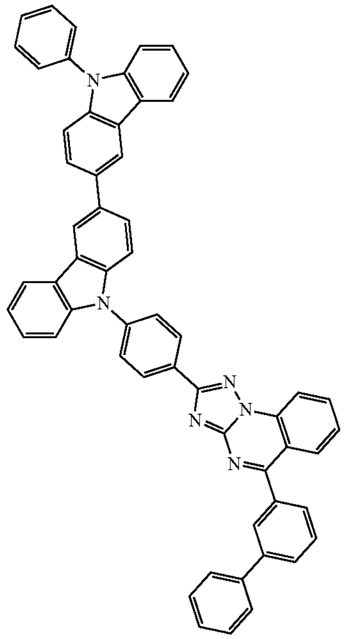
-continued
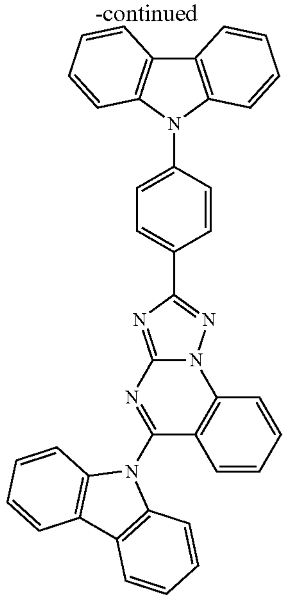
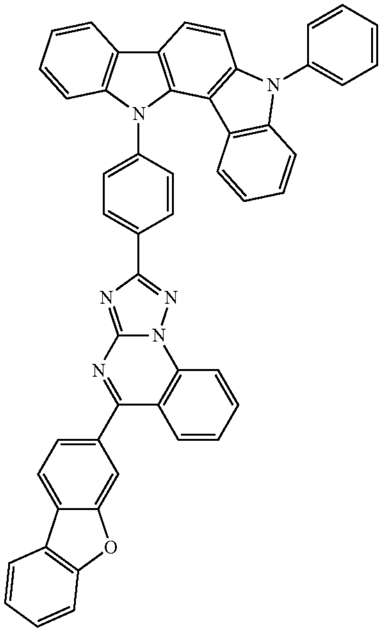
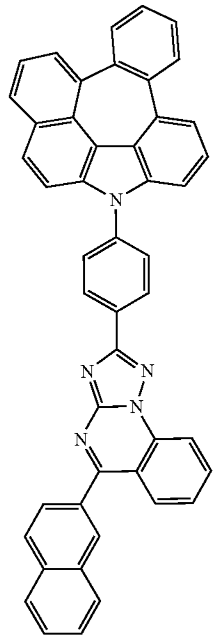

-continued
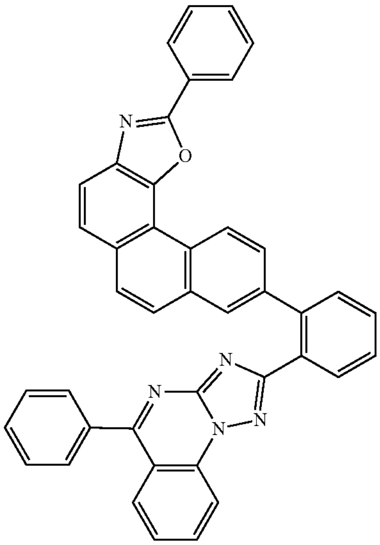
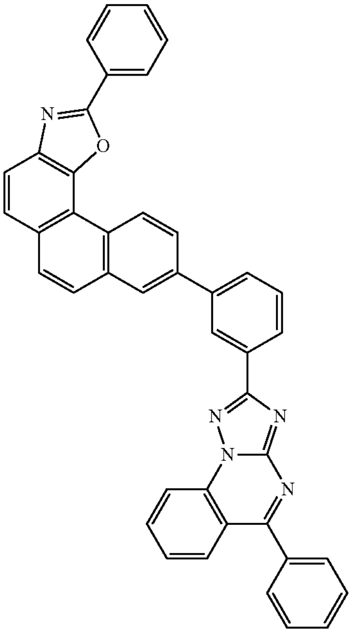
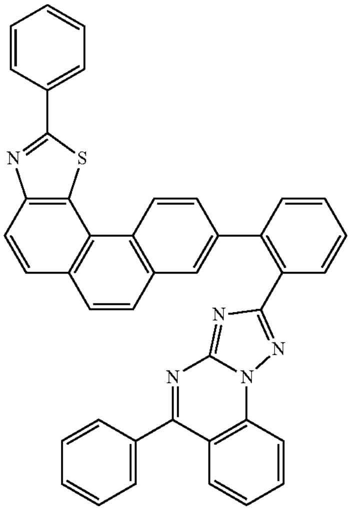
-continued
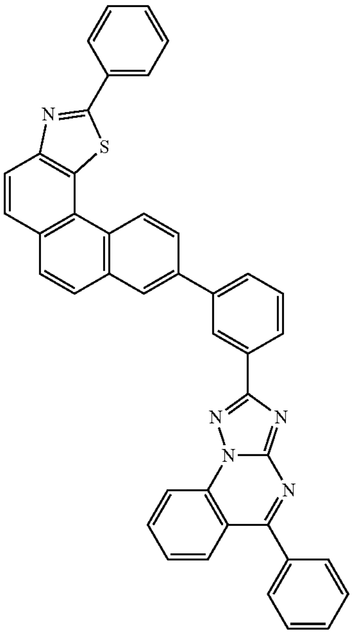
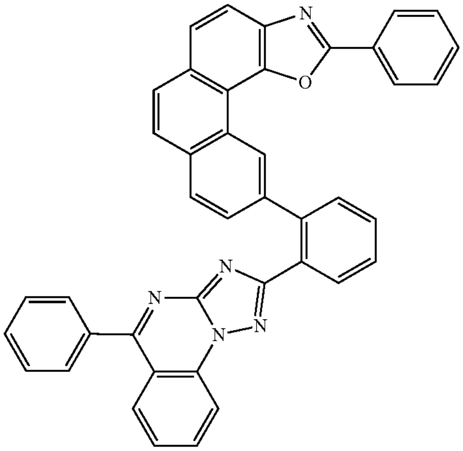
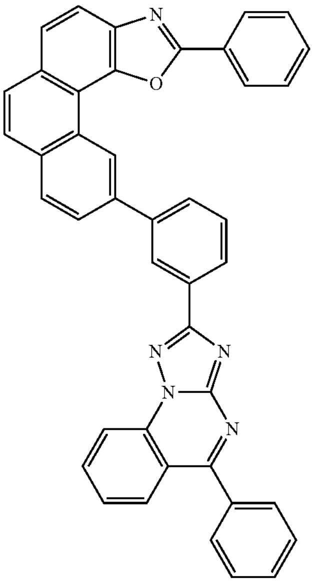

-continued
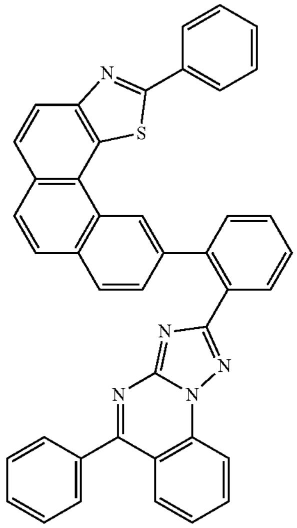
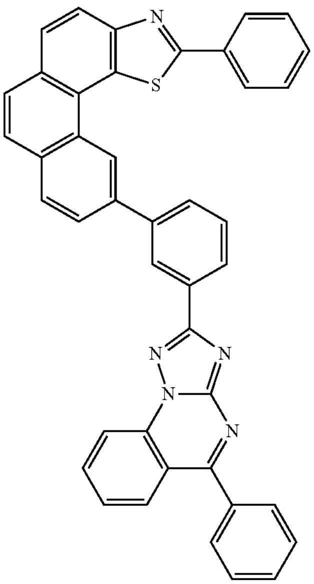
-continued
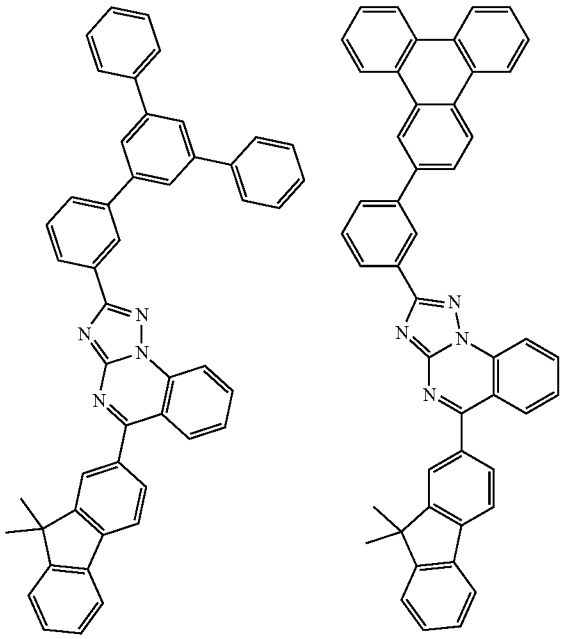
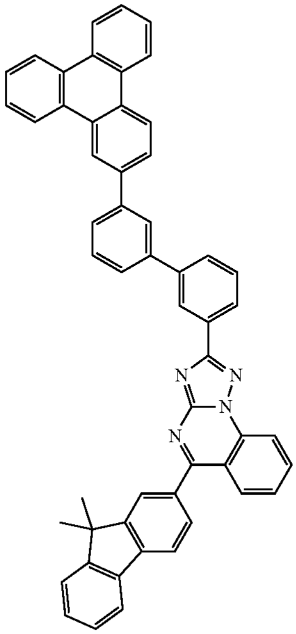

-continued
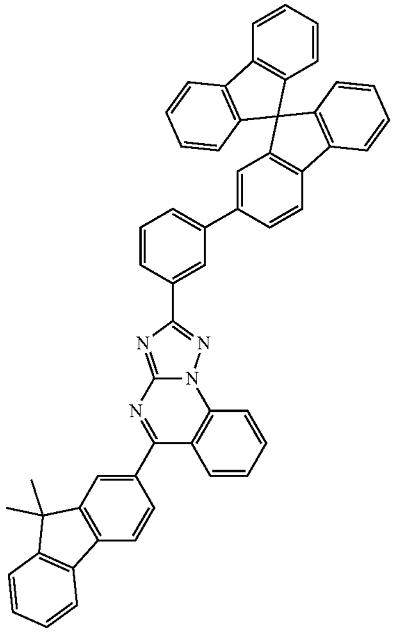
-continued
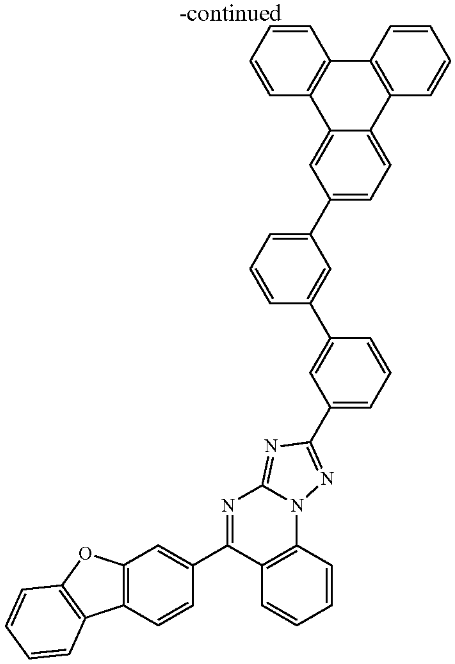
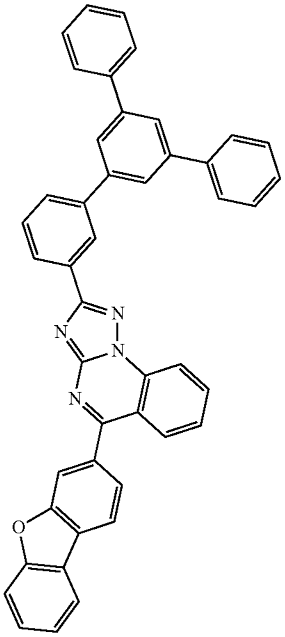
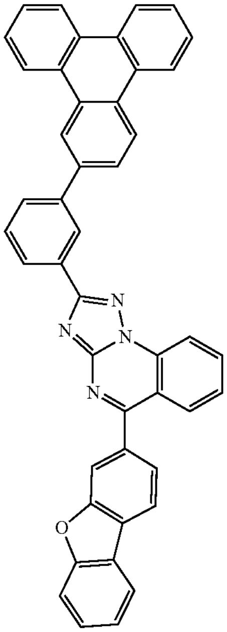
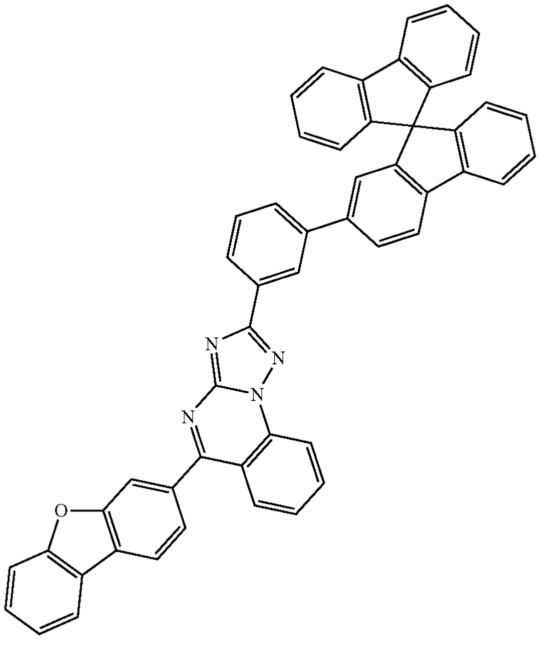

-continued
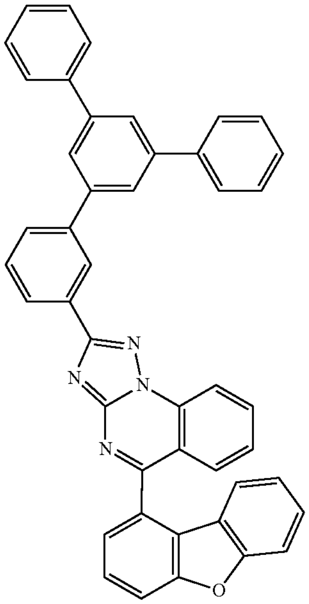
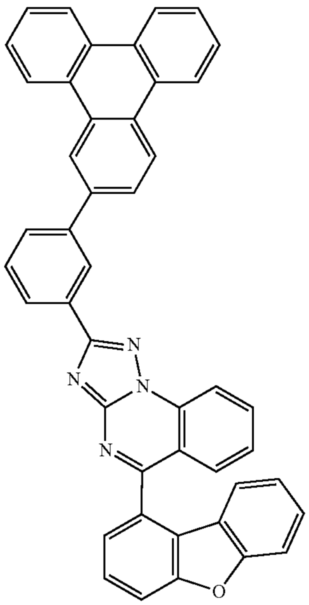
-continued
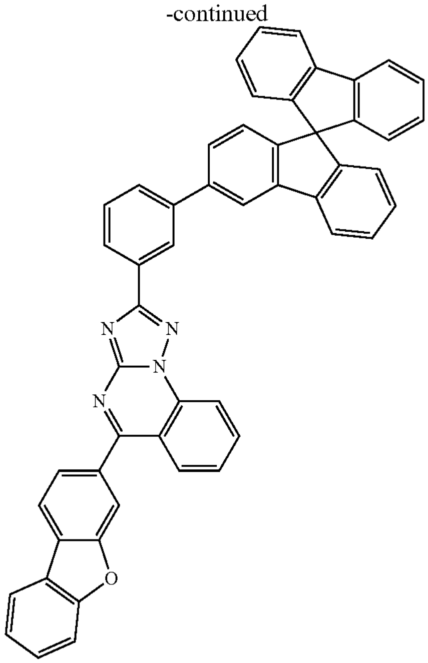
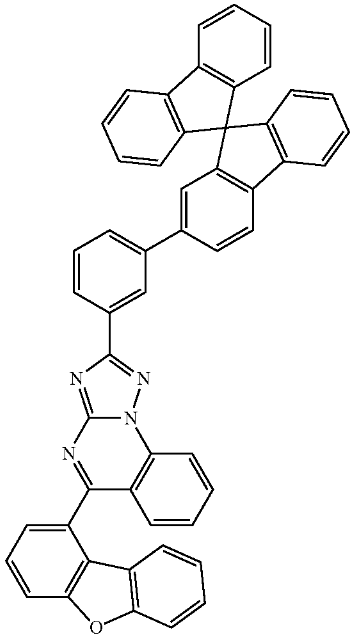

-continued
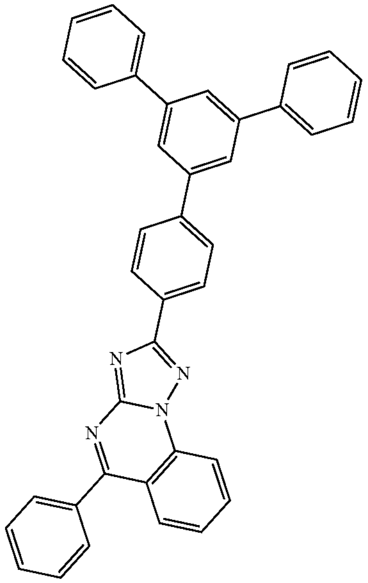
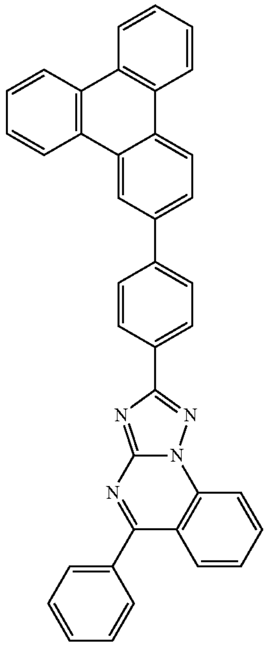
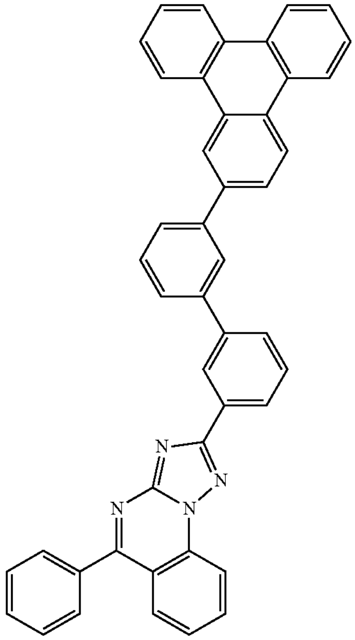
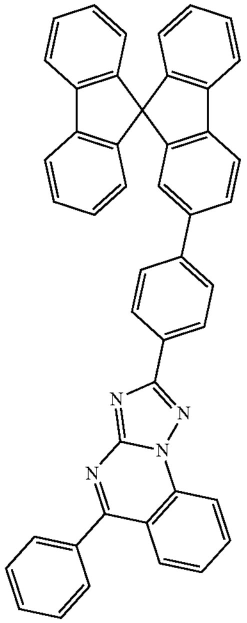
-continued

-continued
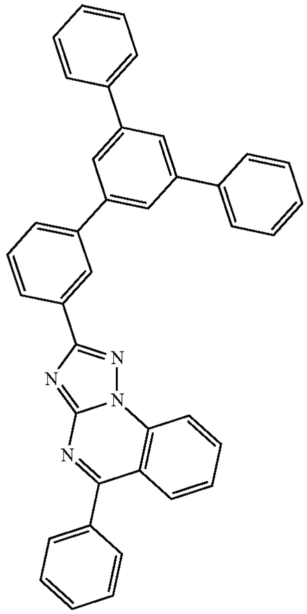
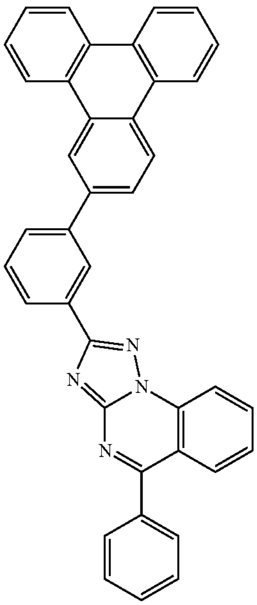
-continued
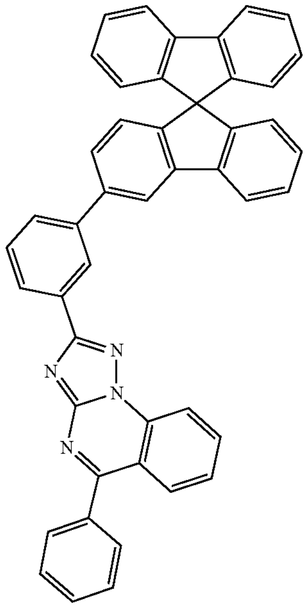
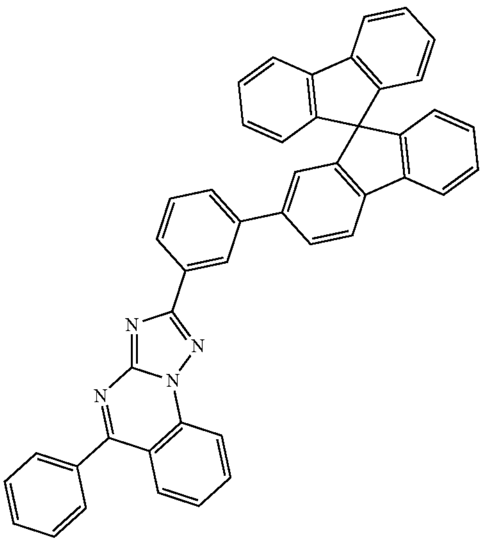
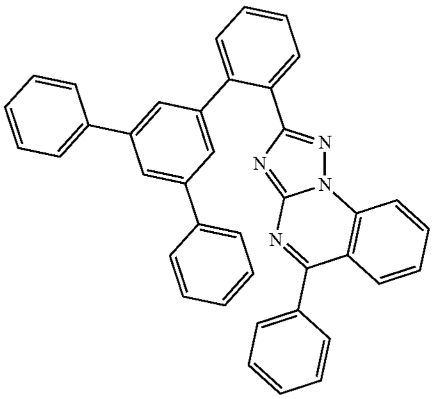

-continued
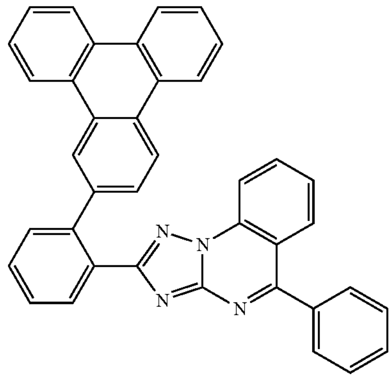
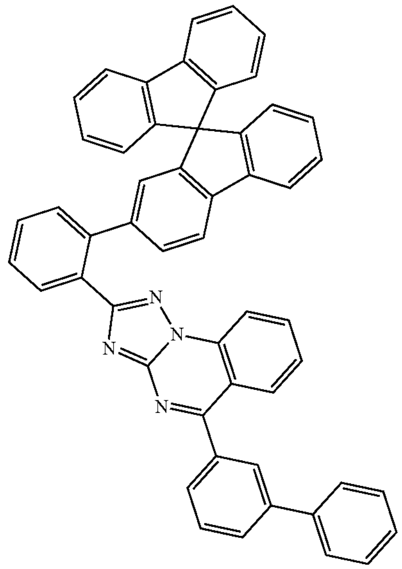
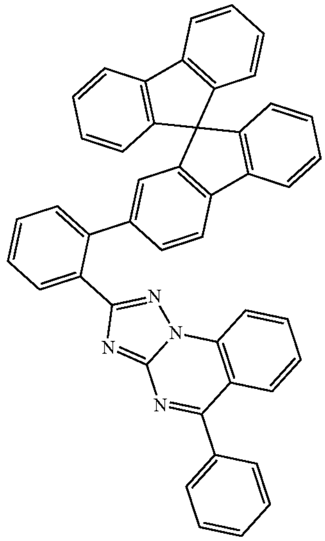
-continued
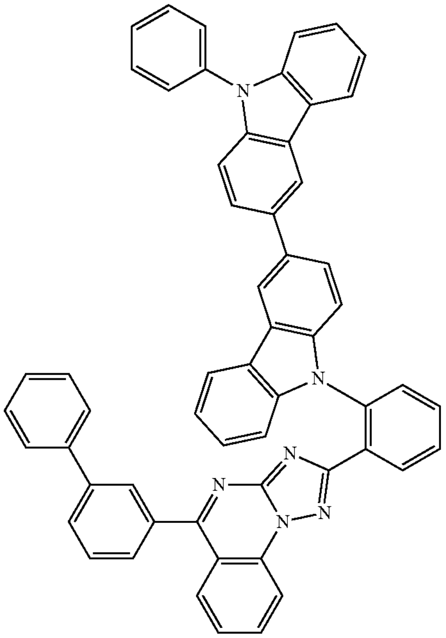
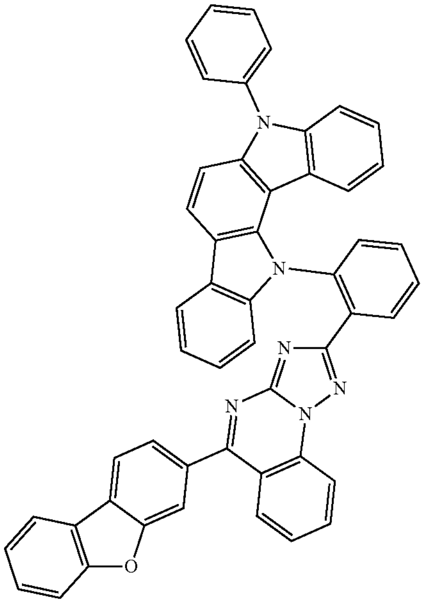
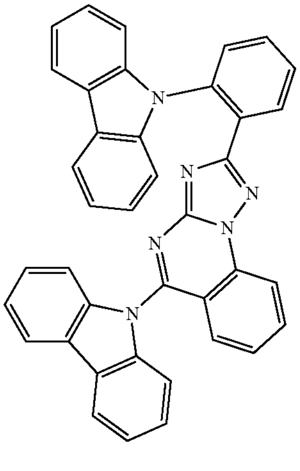

-continued
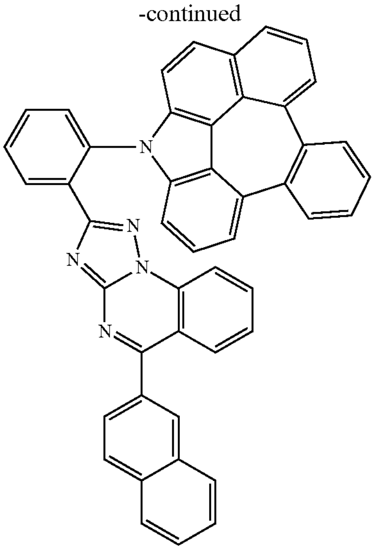
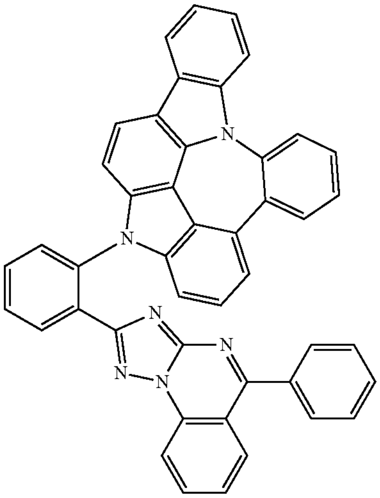
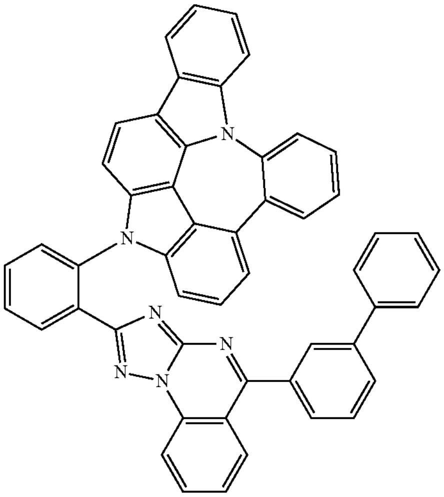
-continued
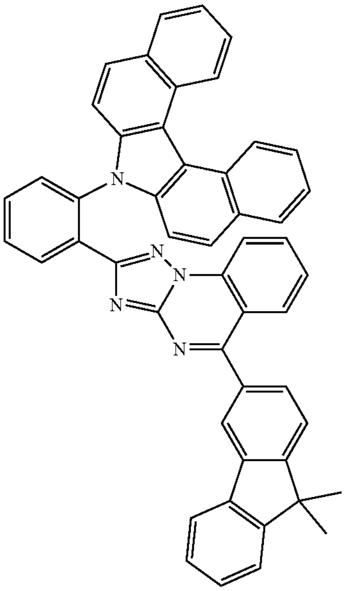
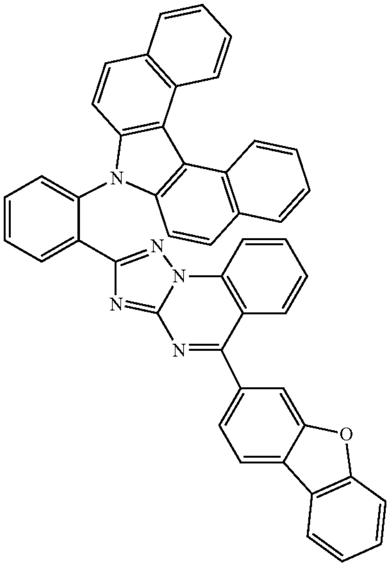
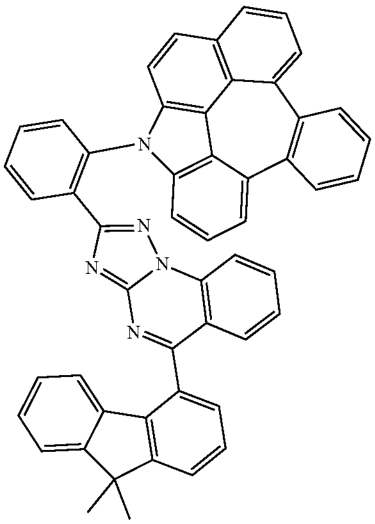

-continued
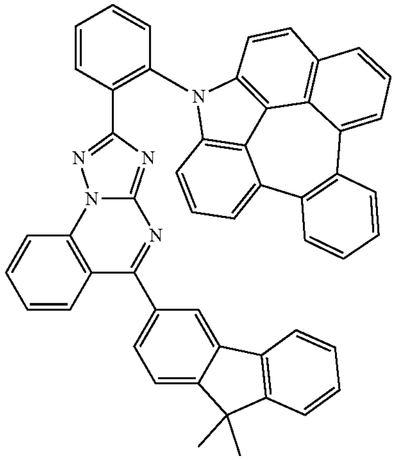
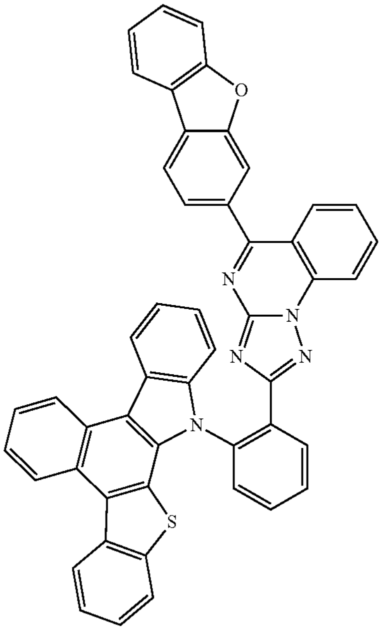
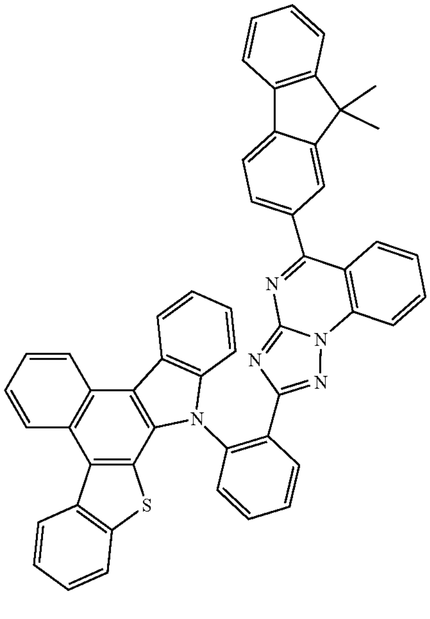
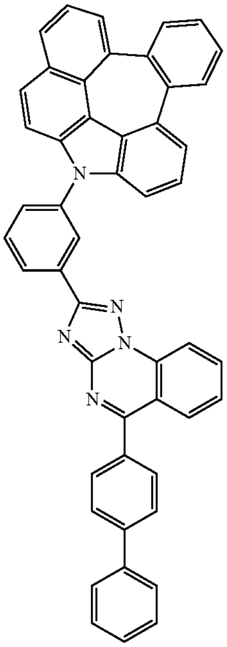
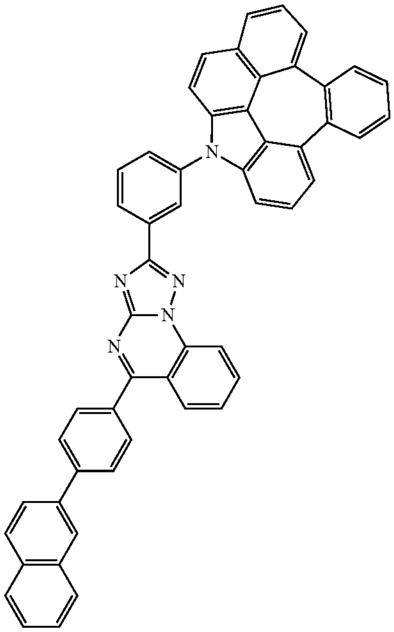

-continued
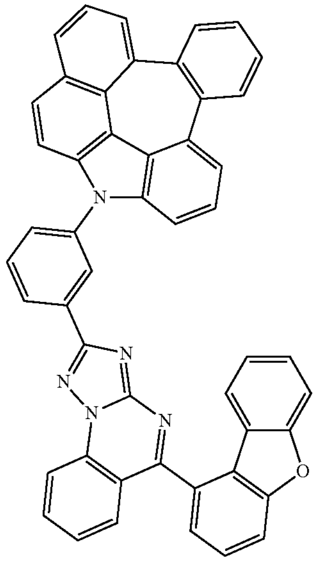
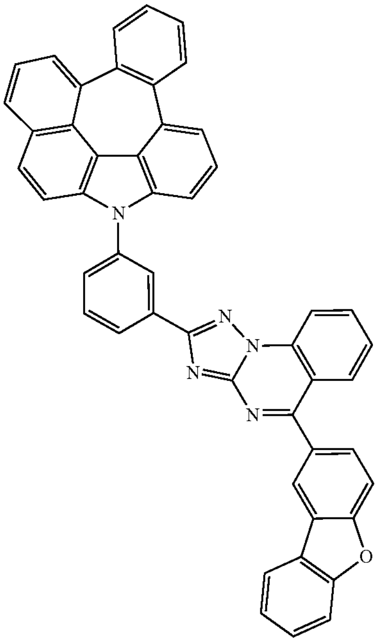
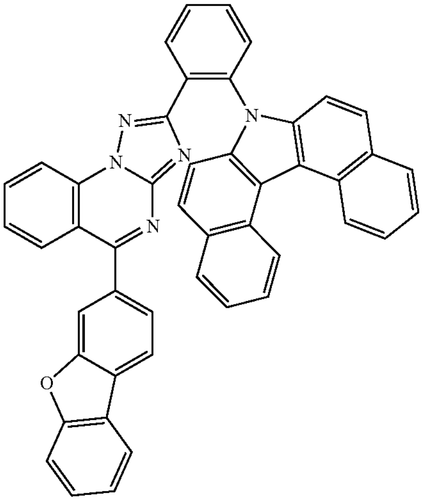
-continued
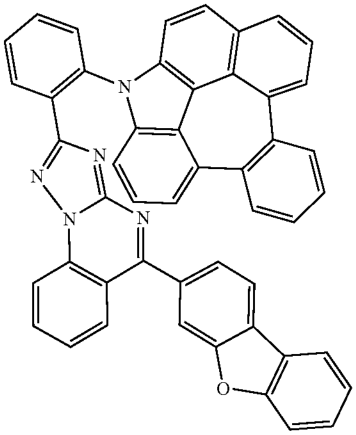
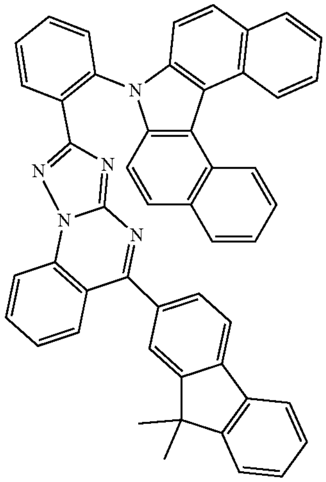
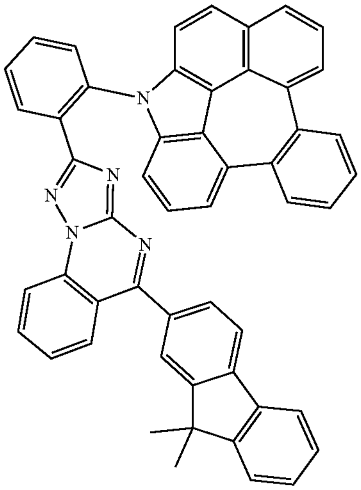

-continued
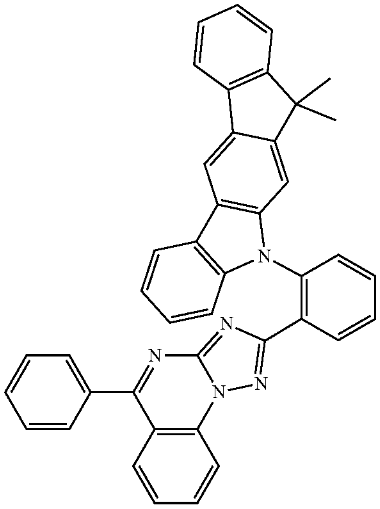
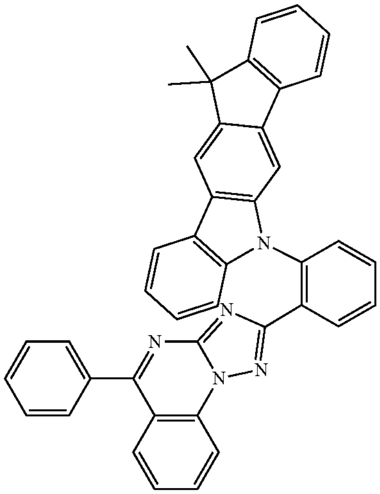
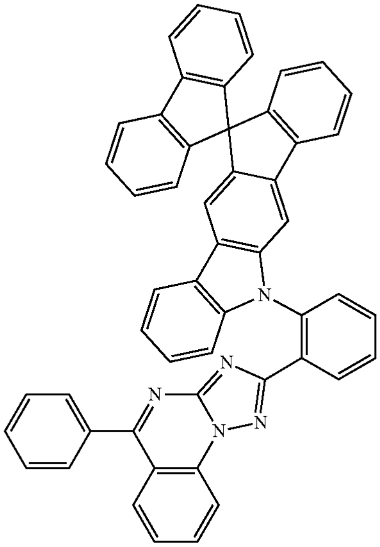
-continued
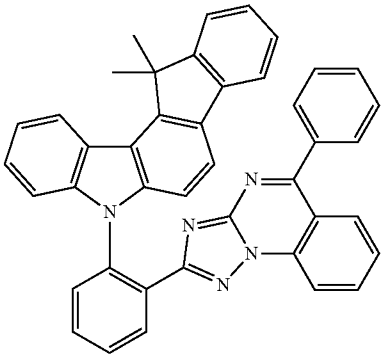
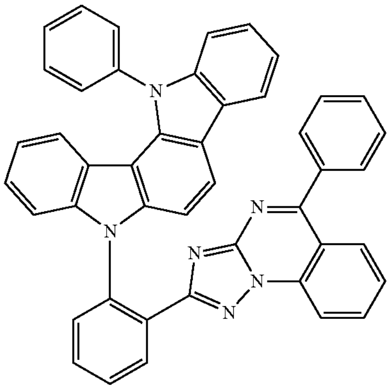
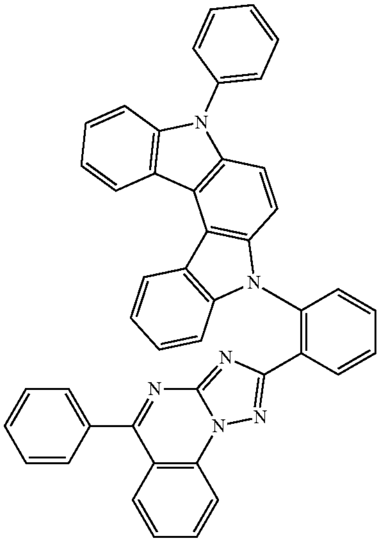

-continued
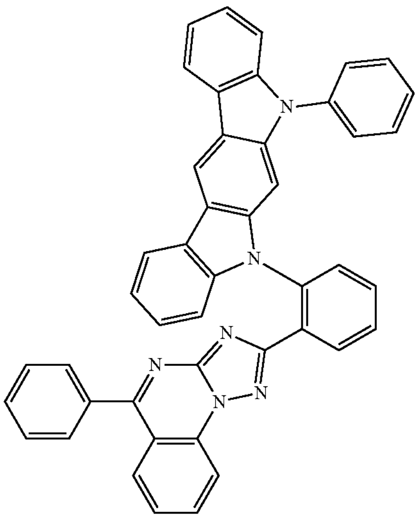
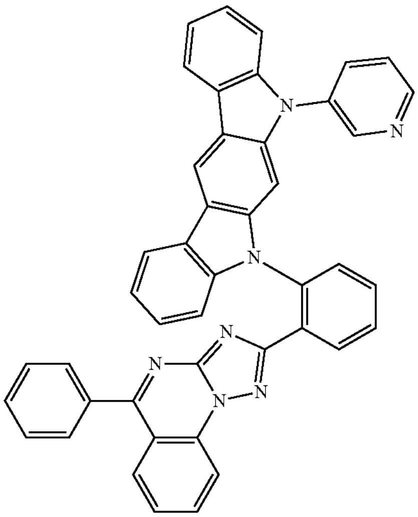
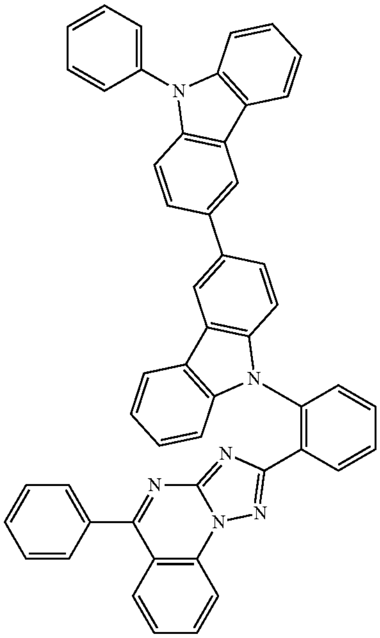
-continued
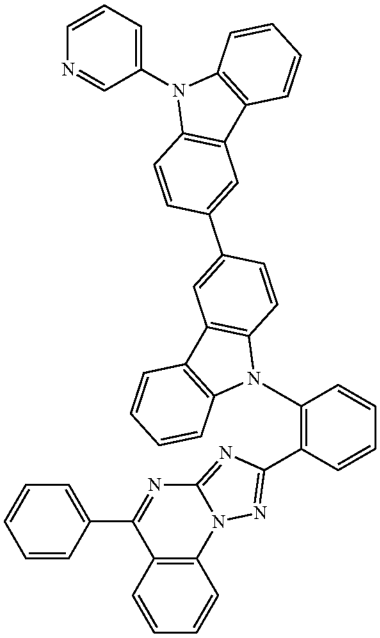
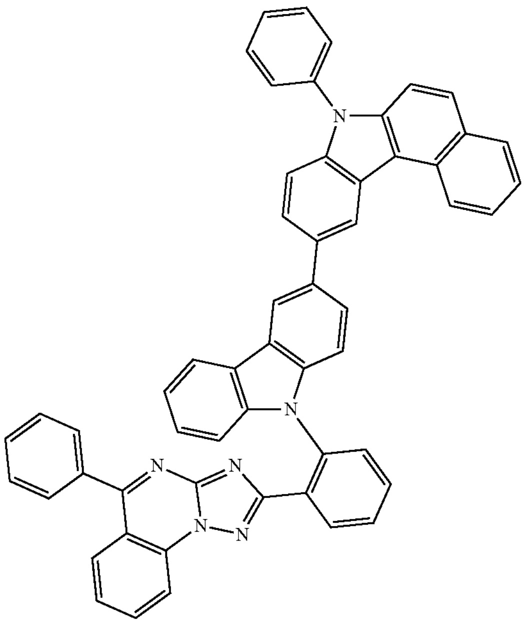

-continued
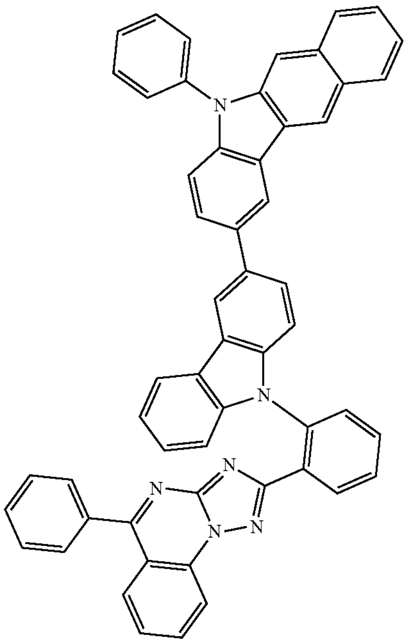
-continued
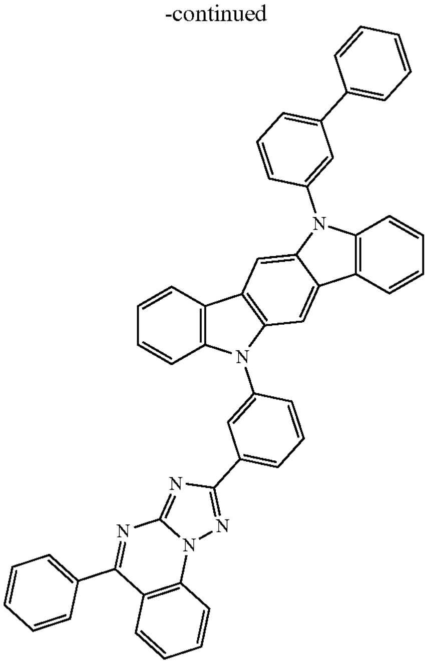
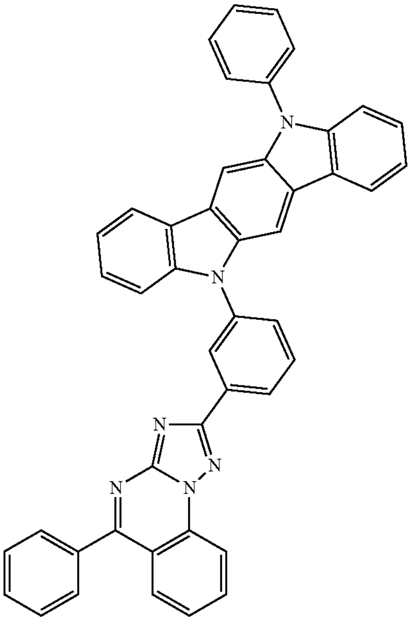
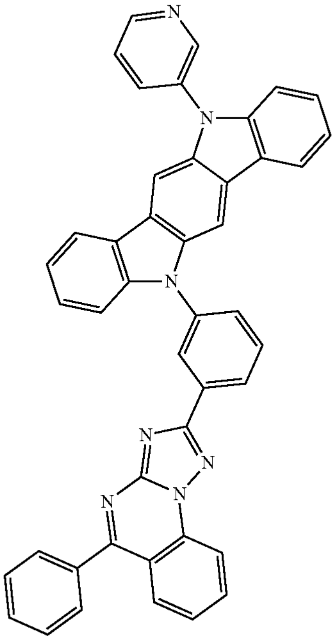

-continued
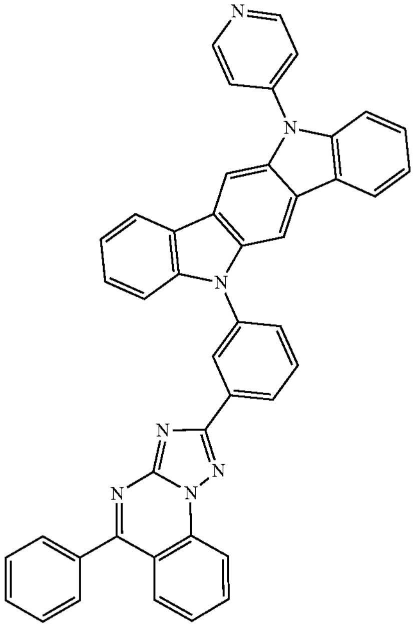
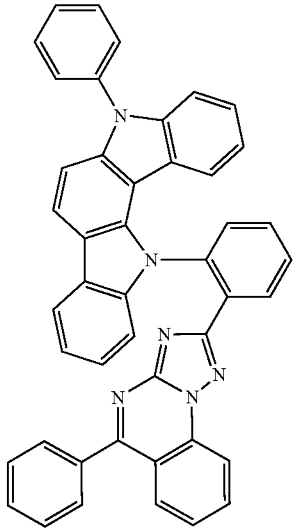
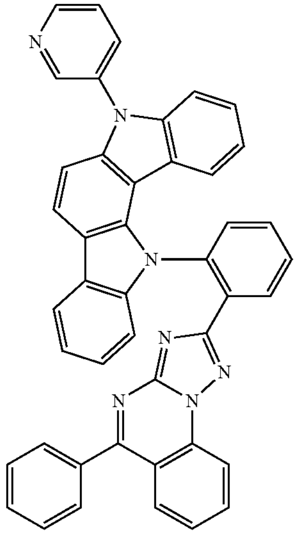
-continued
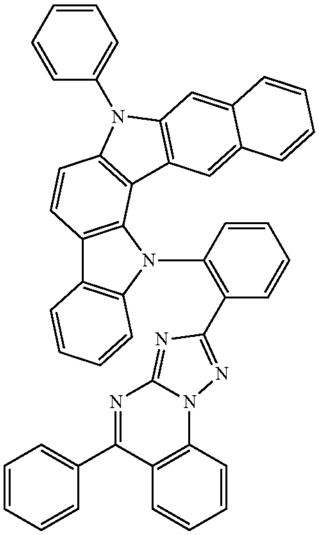
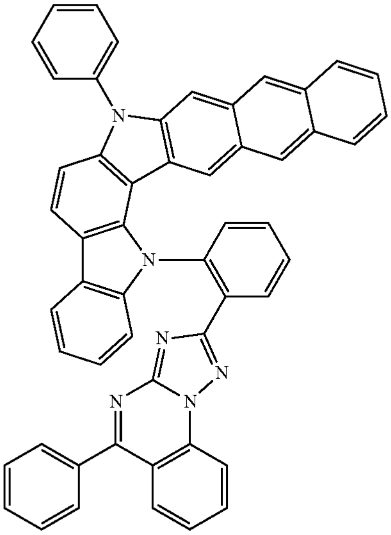
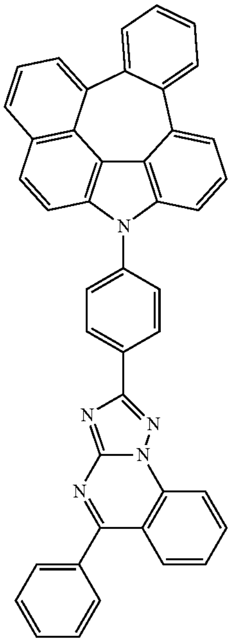

-continued
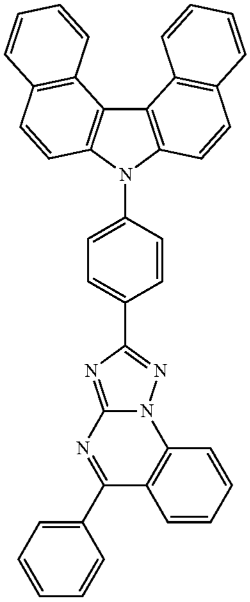
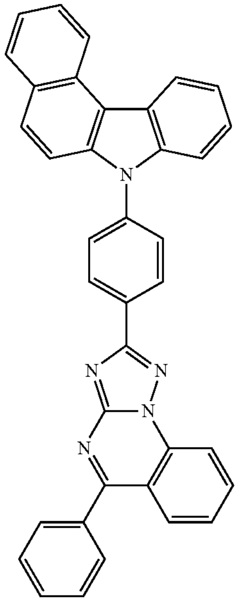
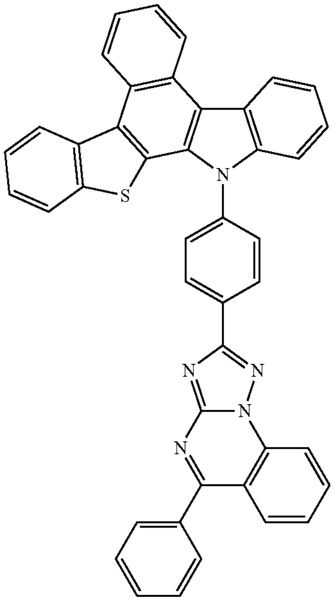
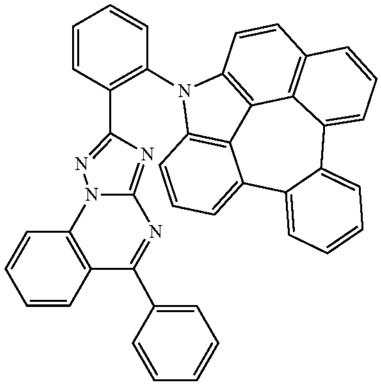
-continued
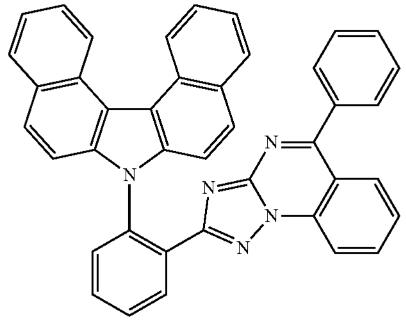
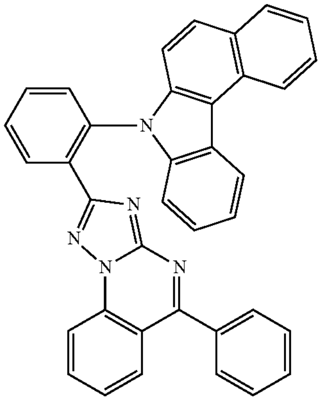
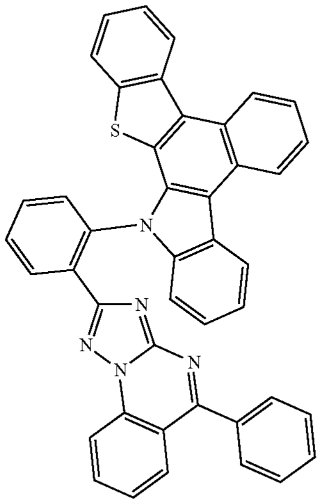

-continued
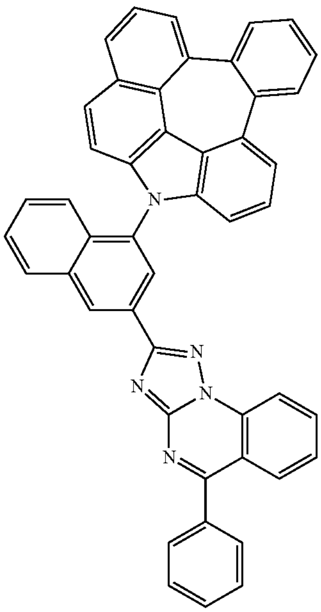
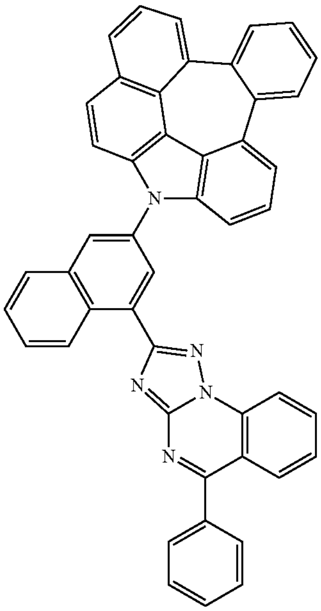
-continued
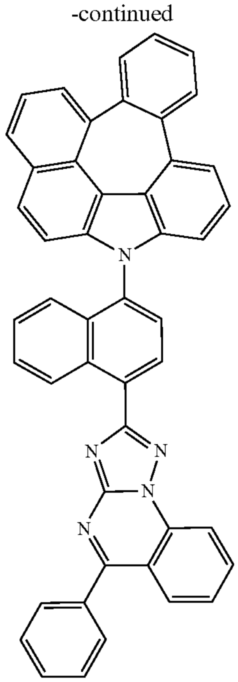
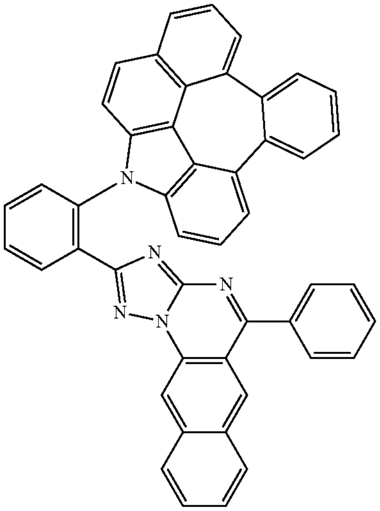
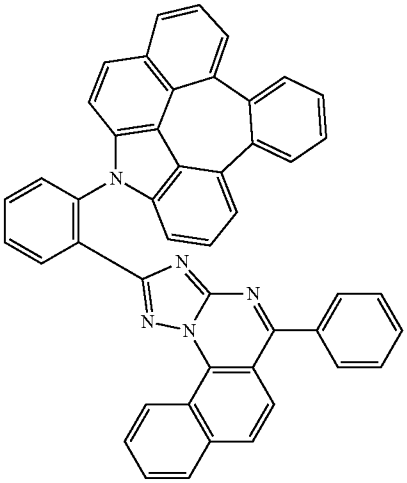

-continued
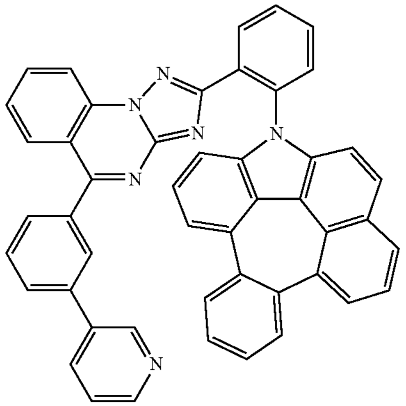
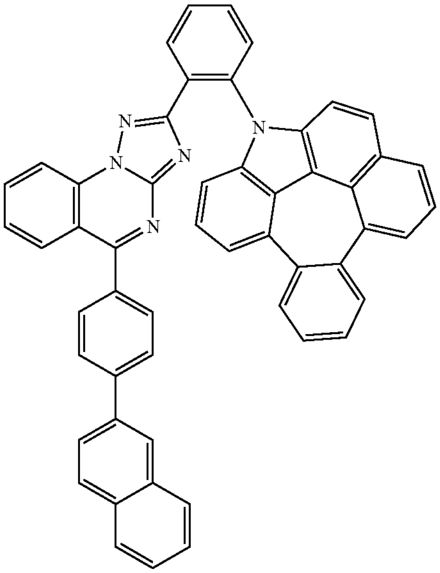
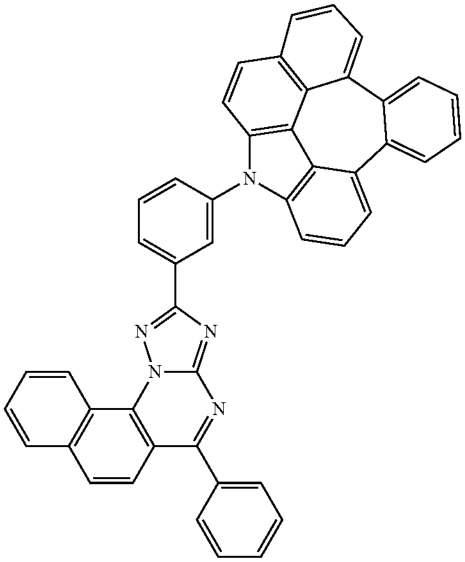
-continued
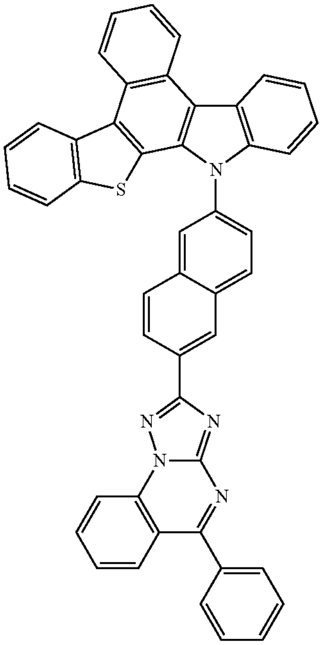
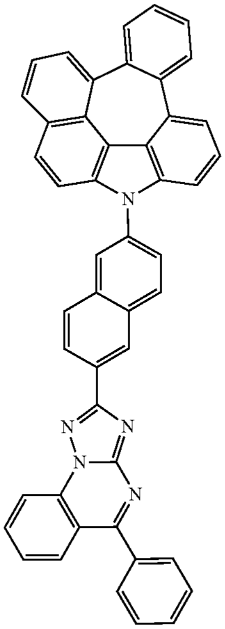

-continued
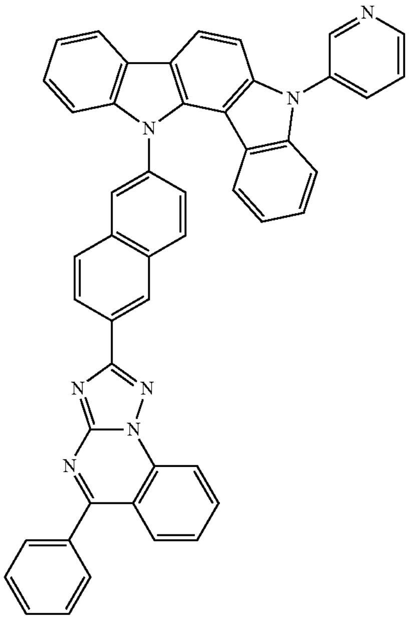
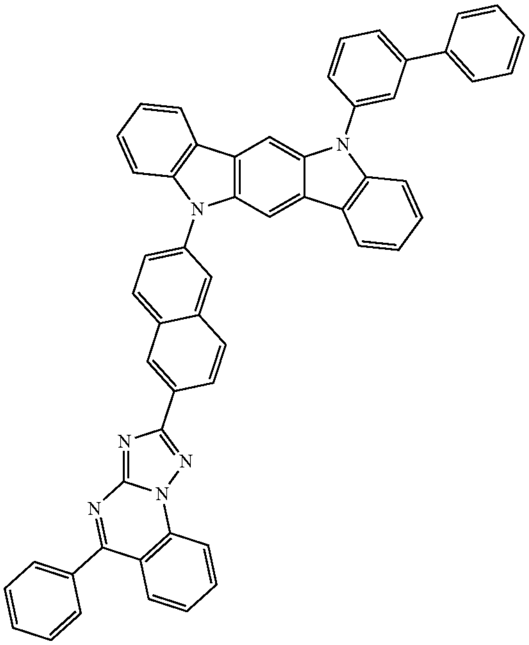
-continued
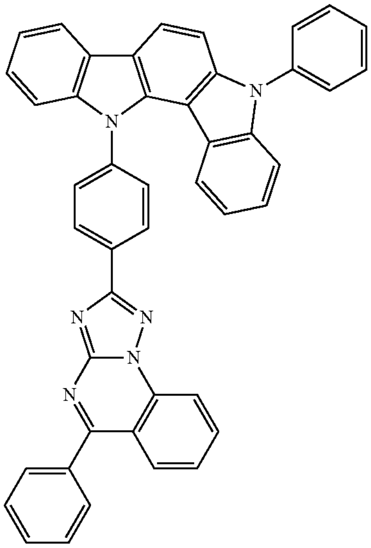
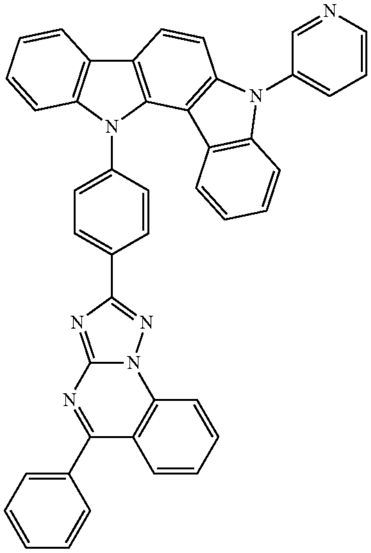
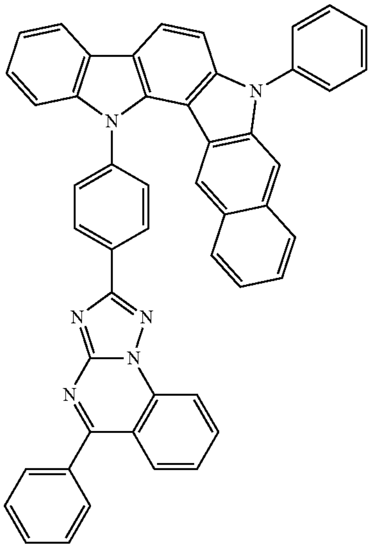

-continued
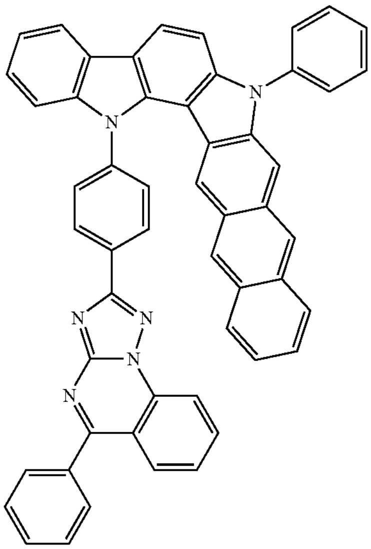
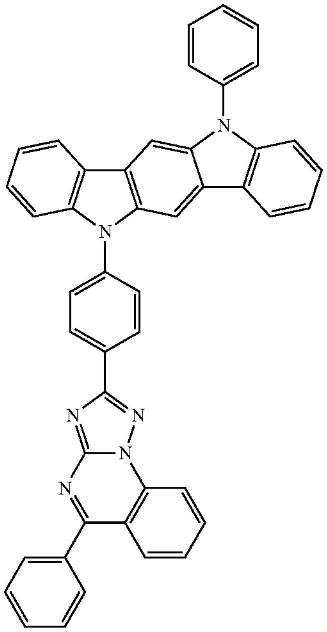
-continued
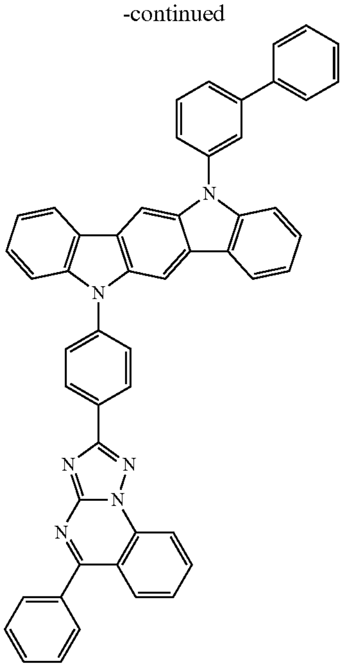
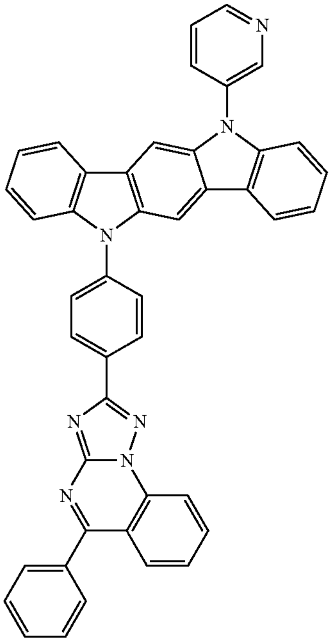

-continued
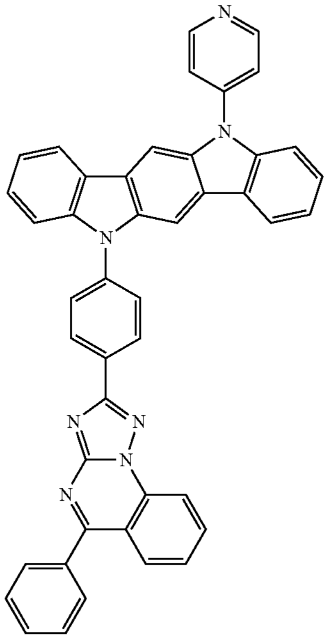
-continued
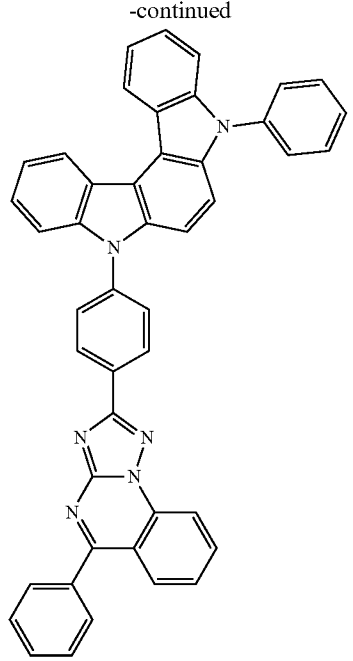
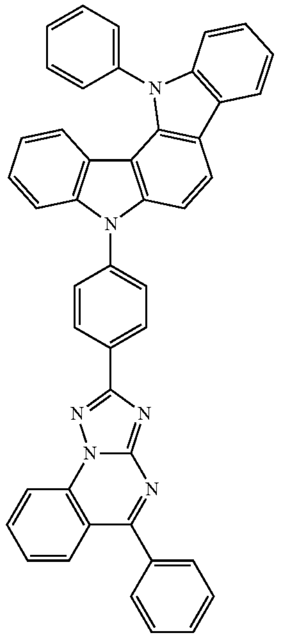
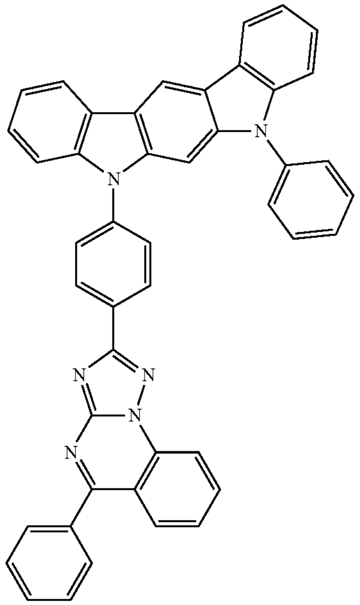

-continued
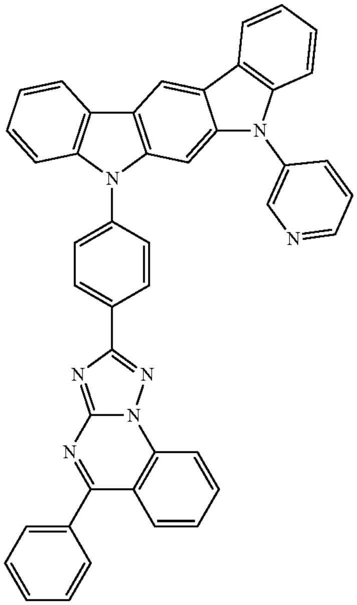
-continued
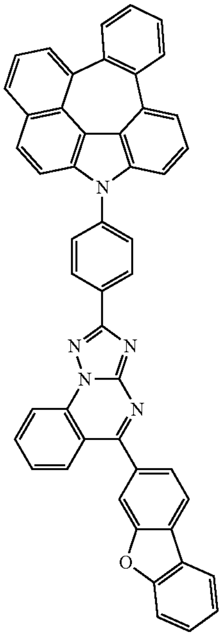
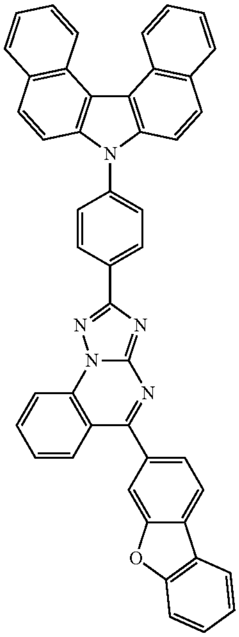
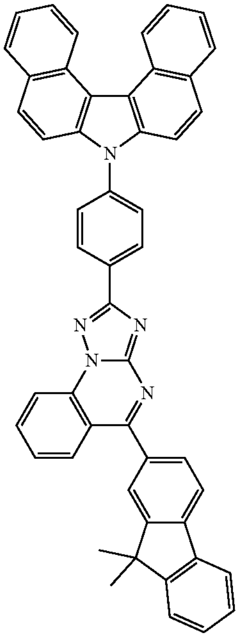

-continued
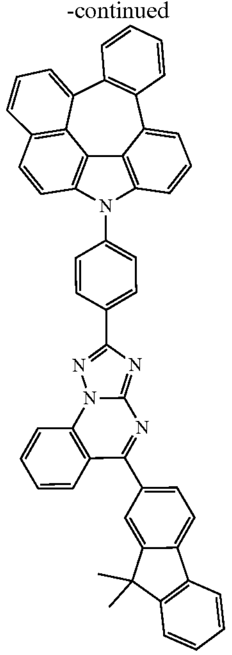
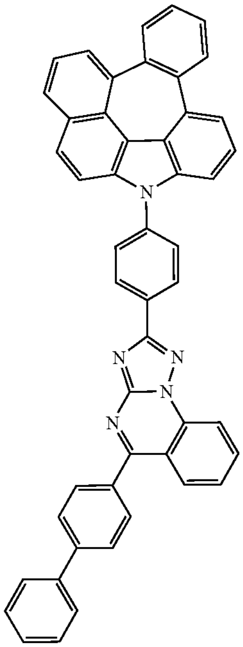
-continued
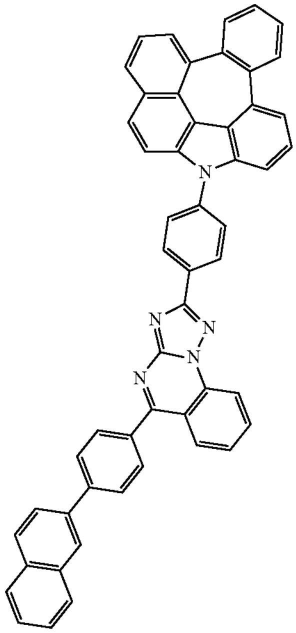
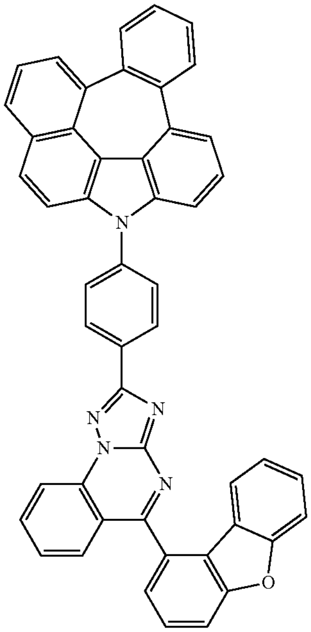

-continued
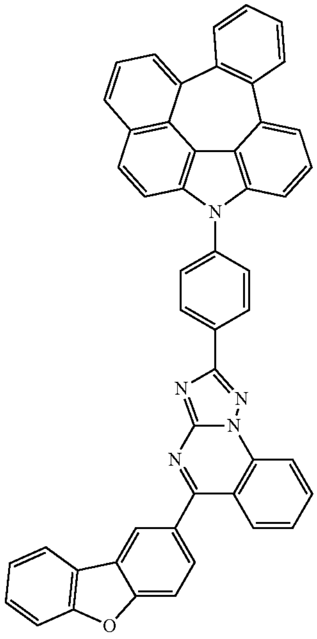
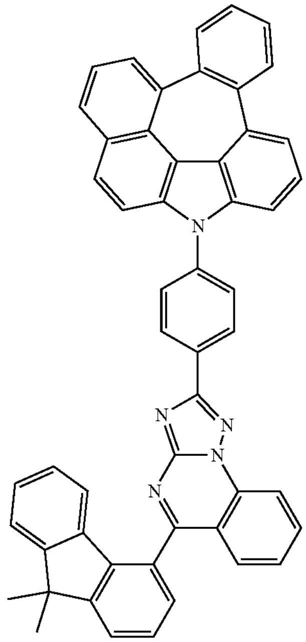
-continued
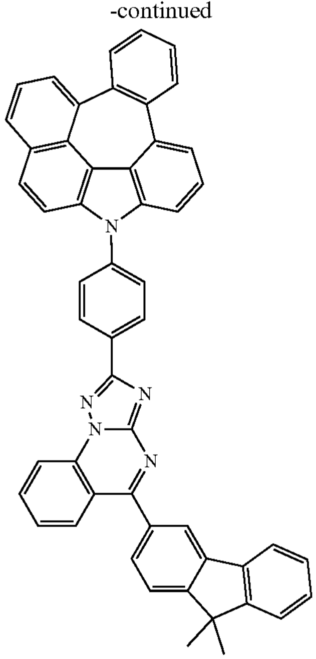
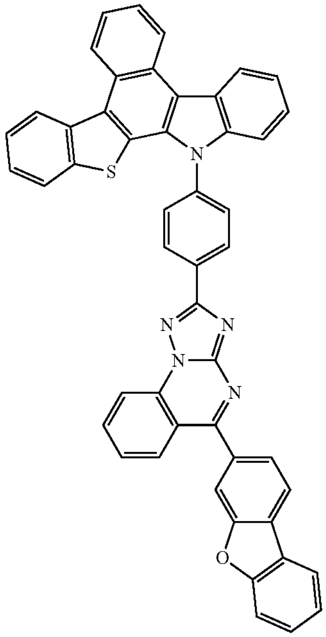

-continued
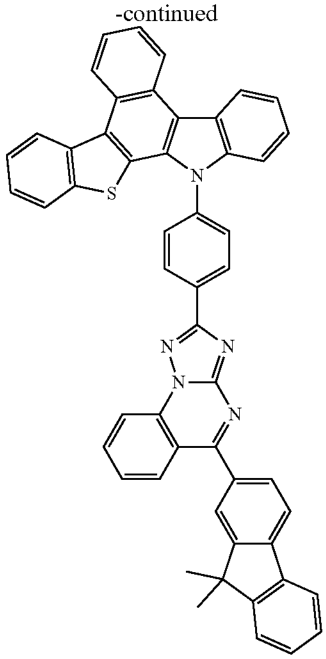
-continued
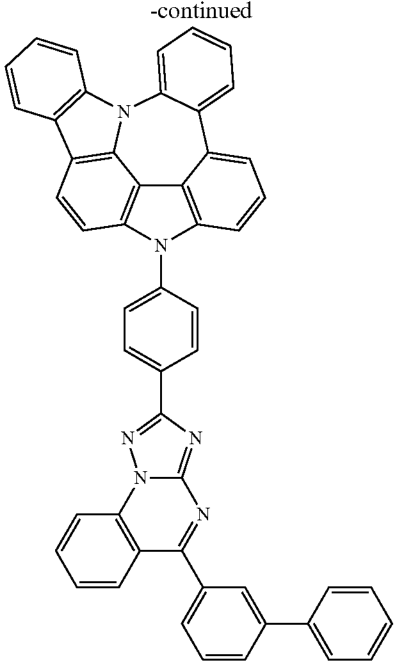
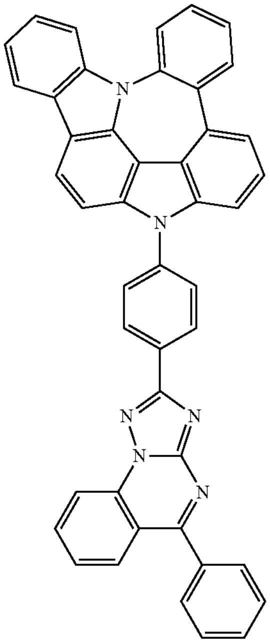
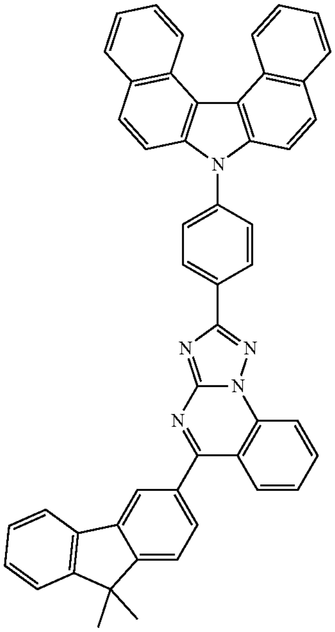

-continued
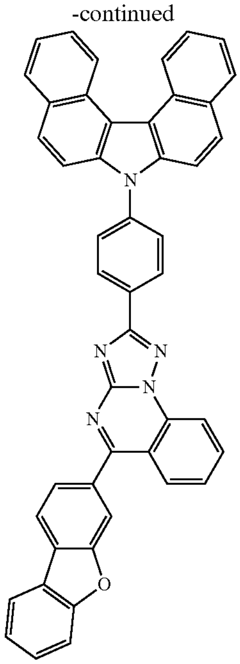
-continued
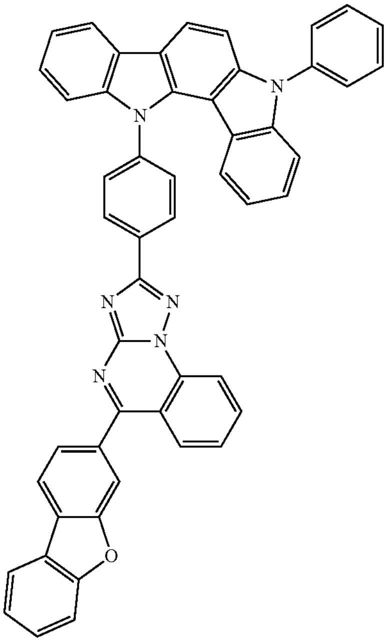
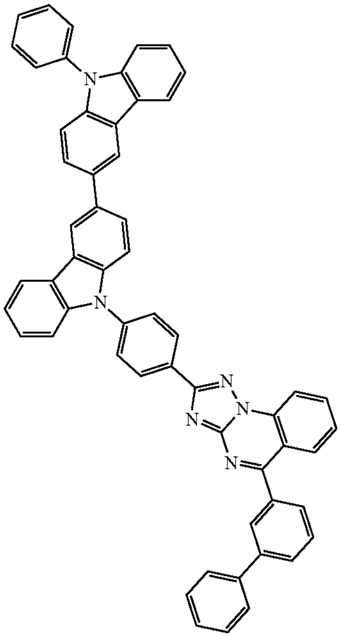
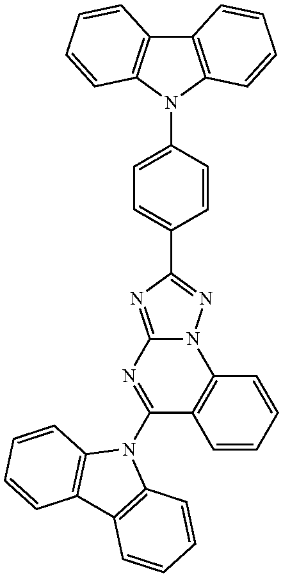
and

-continued

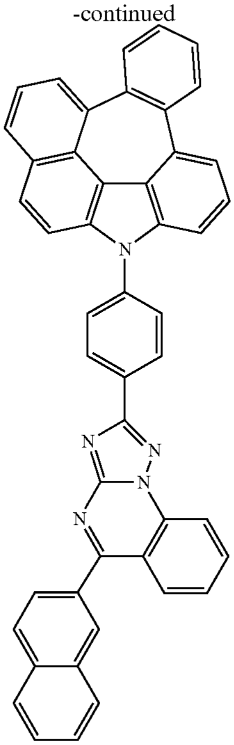

.

3. An application of the nitrogen-containing fused heterocyclic compound as claimed in claim 1 in preparation of an optical element.

4. The application as claimed in claim 3, wherein the optical element comprises any one of an organic electroluminescence element, an organic field-effect transistor, an organic thin film transistor, an organic light-emitting transistor, an organic integrated circuit, an organic solar cell, an organic field quenching element, a light-emitting electrochemical cell, an organic laser diode, and an organic photoreceptor.

5. An organic electroluminescence element, wherein the organic electroluminescence element comprises an anode, a cathode, and an organic layer disposed between the anode and the cathode, and the organic layer comprises one or more the nitrogen-containing fused heterocyclic compounds as claimed in claim 1.

6. The organic electroluminescence element as claimed in claim 5, wherein the organic layer comprises a hole injection layer, a hole transport layer, an emitting layer, an electron transport layer and an electron injection layer, which are sequentially layered from a side of the anode to a side of the cathode.

7. An organic electroluminescence device, wherein the organic electroluminescence device comprises the organic electroluminescence element as claimed in claim 5.

* * * * *